US007803382B2

(12) United States Patent
Old et al.

(10) Patent No.: US 7,803,382 B2
(45) Date of Patent: Sep. 28, 2010

(54) METHOD FOR INDUCING IMMUNE RESPONSE TO NY-CO-58

(75) Inventors: Lloyd J. Old, New York, NY (US); Sacha Gnjatic, New York, NY (US); Djordje Atanackovic, Hamburg (DE); Vincenzo Cerundolo, Oxford (GB); Khoon-Lin Ling, Oxford (GB)

(73) Assignees: Ludwig Institute for Cancer Research Ltd., New York, NY (US); Chancelors Masters and Scholars of the University of Oxford, Oxford (GB)

( * ) Notice: Subject to any disclaimer, the term of this patent is extended or adjusted under 35 U.S.C. 154(b) by 1562 days.

(21) Appl. No.: 10/938,767

(22) Filed: Sep. 9, 2004

(65) Prior Publication Data

US 2008/0226664 A1    Sep. 18, 2008

Related U.S. Application Data

(63) Continuation-in-part of application No. 09/849,602, filed on May 4, 2001, now Pat. No. 6,794,501.

(51) Int. Cl.
*A61K 39/00*    (2006.01)
(52) U.S. Cl. ............... 424/185.1; 424/184.1; 514/2
(58) Field of Classification Search ............... None
See application file for complete search history.

(56) References Cited

U.S. PATENT DOCUMENTS

| | | | |
|---|---|---|---|
| 4,816,567 A | 3/1989 | Cabilly et al. | |
| 5,225,539 A | 7/1993 | Winter | |
| 5,585,089 A | 12/1996 | Queen et al. | |
| 5,693,762 A | 12/1997 | Queen et al. | |
| 5,804,381 A | 9/1998 | Chen et al. | |
| 5,859,205 A | 1/1999 | Adair et al. | |
| 5,962,256 A | 10/1999 | Moore et al. | |
| 6,331,424 B1 * | 12/2001 | Beraud et al. | 435/196 |
| 6,544,766 B1 * | 4/2003 | Beraud et al. | 435/196 |
| 6,794,501 B2 | 9/2004 | Chen et al. | |

FOREIGN PATENT DOCUMENTS

| WO | WO 99/04265 A2 | 1/1999 |
|---|---|---|
| WO | WO 99/14326 A1 | 3/1999 |
| WO | WO 99/60986 A2 | 12/1999 |

OTHER PUBLICATIONS

Lee et al (J. Immunol., 1999, 163:6292-6300).*
Kirkin et al (1998, APMIS, 106 : 665-679).*
Chaux et al, (Int J Cancer, 1998, 77: 538-542).*
Boon (Adv Can Res, 1992, 58:177-210).*
Celis (J of Clinical Investigation, 2002, 110:1765-1768).*
Christiansen et al (Mol Cancer Ther, 2004, 3:1493-1501).*
Meibohm (Pharmacokinetics and Pharmacodynamics of Biotech Drugs, Wiley-VHC, 2006, chapter 3, p. 45-91).*
Chen, et al. (1997) Proc Natl Acad Sci USA 94:1914-1918.
Clark, et al. (1994) Nature Genetics 7(4):502-508.
Crew, et al. (1995) EMBO J. 14(10):2333-2340.
Ding, et al. (1994) Biochem Biophys Res Commun. 202(1):549-555.
Fukunaga, et al. (1997) EMBO J. 16(8):1921-1933.
Griggs et al., (2001) *Lancet Oncol.* 2:82.
Grozinger, et al. (1999) Proc. Natl. Acad Sci USA 96:4868-4873.
Harlow, et al. (1985) Molecular & Cell Biol. 5(7):1601-1610.
Hendrich, et al. (1998) Molecular & Cell Biol. 18(11):6538-6547.
Kim, et al. (1999) Molecular & Cell Biol. 19(9):6323-6332.
Kim, et al. (1997) Biochim Biophys Acta Dec 12;1359(3):181-6.
Kunkel, (1985) *Proc. Nat. Acad. Sci. U.S.A.* 82: 488-492.
MacBeath et al., (2000) "Printing Proteins as Microarrays for High-Throughput Function Determination," *Science* 289(5485):1760-1763.
Rosen, *Oncologist* 5:20, 2000.
Sahin et al. *Proc. Natl. Acad. Sci. USA* 92:11810-11813, 1995.
Scanlan, et al., *Int. J. Cancer* 76:652-658 (1998).
Scanlan, et al., *Int. J. Cancer* 83:456-64, (1999).
The Chipping Forecast, *Nature Genetics*, vol. 21, Jan. 1999.
Attwood, Science; 290:471-473, 2000.
Gerhold et al., BioEssays, 18(12): 973-981, 1996.
Lopez et al., Molecular Biology, 32: 881-891, 1999.
Russell et al., Journal of Molecular Biology, 244: 332-350, 1994.
Wells et al., Journal of Leukocyte Biology, 61(5): 545-550, 1997.

* cited by examiner

*Primary Examiner*—Laura B Goddard
(74) *Attorney, Agent, or Firm*—Wolf, Greenfield & Sacks, P.C.

(57) ABSTRACT

The invention provides methods, compositions and kits for inducing and/or enhancing an immune response in a subject. The invention in some aspects includes polypeptide and nucleic acid molecules that induce and/or enhance an immune response. In some aspects of the invention, the polypeptide and/or nucleic acid molecules of the invention are useful to induce and/or enhance an immune response in a subject who has or is suspected of having cancer.

4 Claims, 4 Drawing Sheets

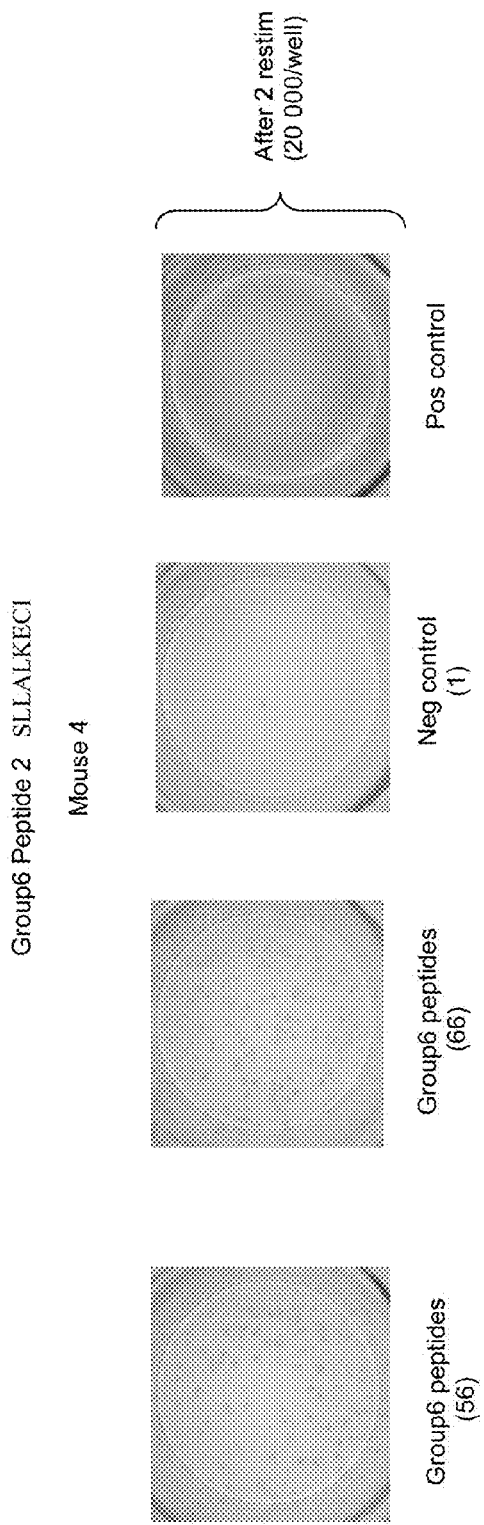
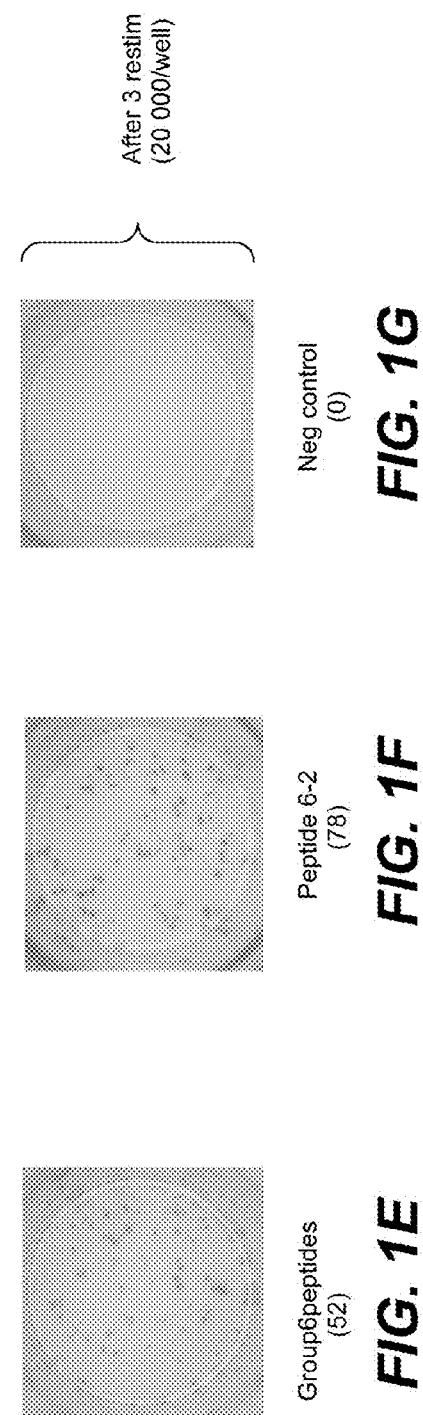

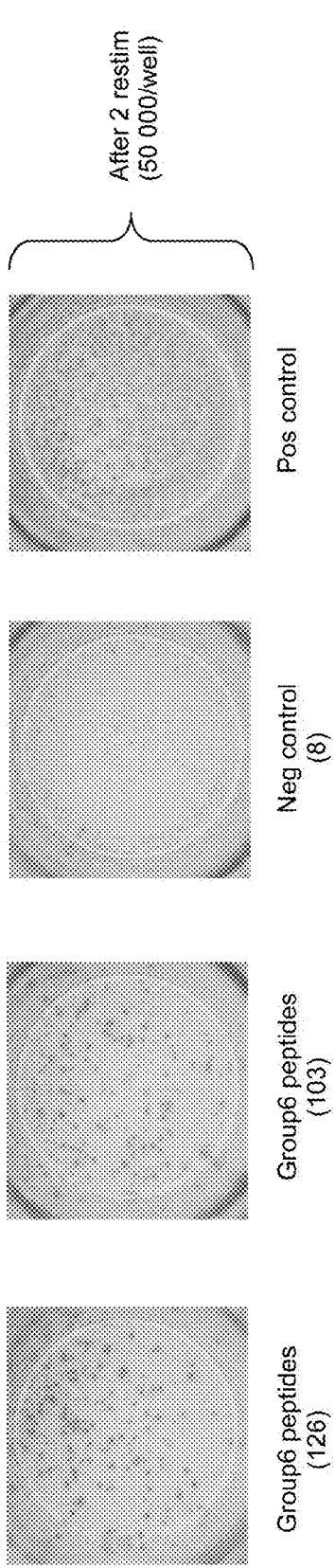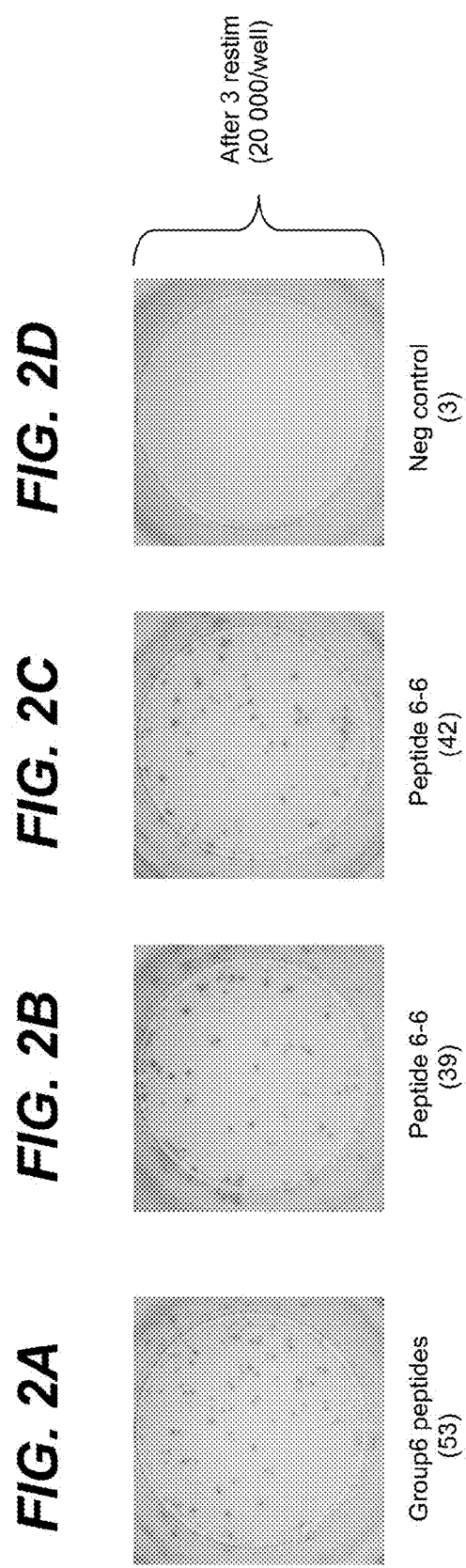

Group 1 Peptide 3 NLEKSCVSV
Mouse 1
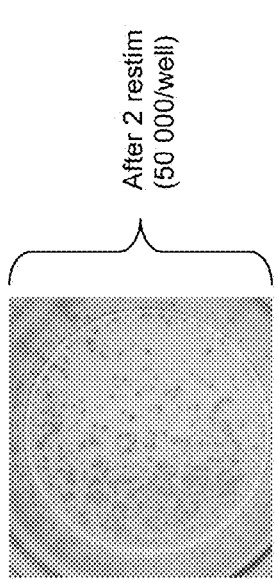
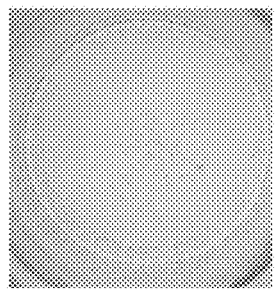
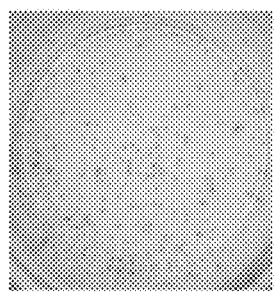
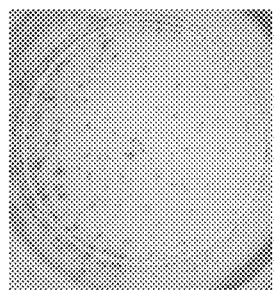
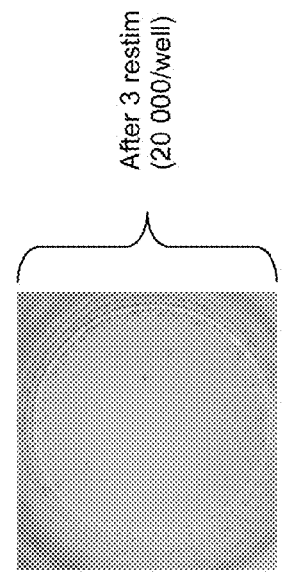
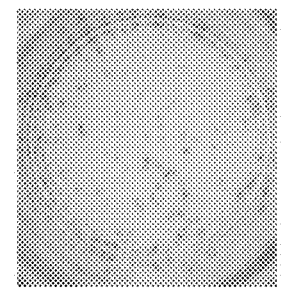
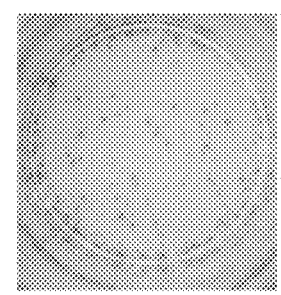
After 2 restim (50 000/well)
After 3 restim (20 000/well)
Group1 peptides (59)
*FIG. 3A*
Group1 peptides (63)
*FIG. 3B*
Neg control (2)
*FIG. 3C*
Pos control
*FIG. 3D*
Group1 peptides (20)
*FIG. 3E*
Peptide 1-3 (50)
*FIG. 3F*
Peptide 1-3 (59)
*FIG. 3G*
Neg control (3)
*FIG. 3H*

Group 3 Peptide 3 KLGLEVYVT
Mouse 1

Group3 peptides

Group3 peptides

Neg control (2)

Pos control

After 2 restim (50 000/well)

Group3 peptides (186)

Peptide 3-3 (152)

Peptide 3-3 (204)

Neg control (2)

After 3 restim (20 000/well)

SEQUENCE LISTING

<160> NUMBER OF SEQ ID NOS: 73

<210> SEQ ID NO 1
<211> LENGTH: 5901
<212> TYPE: DNA
<213> ORGANISM: Homo sapiens

<400> SEQUENCE: 1

| | | | | | | |
|---|---|---|---|---|---|---|
| ctggagttca | agatttctga | tgaggaggca | gatgatgcag | atgctgctgg | gagggattcc | 60 |
| ccctccaaca | cctcccagtc | agaacagcag | gaatctgttg | atgcagaagg | cccagtggta | 120 |
| gaaaaaatta | tgagcagtcg | ttcagtaaaa | aagcagaagg | aatctggaga | ggaggtagaa | 180 |
| attgaggaat | tctatgtgaa | atacaaaaac | ttctcttatc | ttcattgtca | gtgggcatct | 240 |
| atagaagatc | tggaaaaaga | taagagaatt | cagcaaaaaa | ttaaacgatt | taaggcaaag | 300 |
| cagggccaga | acaagttcct | ttcagagatt | gaggatgagc | tttttaatcc | agattatgtg | 360 |
| gaggttgacc | ggataatgga | ctttgcacgt | agcacagatg | accggggaga | gcctgtgact | 420 |
| cactatctgg | tgaagtggtg | ttcacttcct | tatgaagaca | gcacgtggga | gcggaggcag | 480 |
| gacatagatc | aagcaaagat | cgaggagttt | gagaaactaa | tgtccaggga | gccggaaaca | 540 |
| gagcgtgtgg | agcgacctcc | tgctgatgat | tggaagaaat | cggagagttc | agggagtat | 600 |
| aaaaacaata | acaaactcag | ggaataccag | ttggagggag | taaactggct | acttttcaat | 660 |
| tggtacaaca | tgcgaaactg | catttttagca | gatgaaatgg | gtttgggaaa | aactatccag | 720 |
| tccattacat | ttctctatga | gatatatttg | aaaggaatcc | atggccccttt | tttagtaatt | 780 |
| gccccattgt | ccacaatccc | caactgggaa | agggaattcc | gaacctggac | agagttgaac | 840 |
| gtggttgtgt | atcatgggag | tcaagctagt | cgtcggacca | ttcagttgta | tgaaatgtac | 900 |
| ttcaaagatc | cccagggtcg | agtgataaag | gggtcctata | agtttcatgc | catcatcact | 960 |
| acatttgaga | tgattttgac | tgattgtcct | gagctgcgga | atattccatg | gcgctgtgta | 1020 |
| gtcattgatg | aagcccacag | gctgaagaac | aggaactgca | agctgttgga | gggactcaag | 1080 |
| atgatggact | ggaacacaa | agtgctgctg | acgggaaccc | cactccagaa | cactgtggaa | 1140 |
| gaactcttca | gcttgcttca | tttcttggaa | ccaagtcgct | tcccttcaga | aaccacattt | 1200 |
| atgcaagaat | ttggtgatct | aaaaacagaa | gagcaggtgc | aaaaacttca | agctattcta | 1260 |
| aagccaatga | tgttgagacg | tctcaaagag | gatgtagaaa | agaacttggc | ccccaaagaa | 1320 |
| gaaactatta | ttgaagttga | gctaacaaac | attcagaaga | aatattaccg | agccatcctt | 1380 |
| gagaagaatt | tcacatttct | ttccaaaggc | ggtggtcaag | ctaacgtacc | taacctatta | 1440 |
| aacactatga | tggaattgcg | gaagtgctgc | aatcatccgt | accttatcaa | tggtgctgaa | 1500 |
| gagaaaattt | tggaagagtt | taaagaaaca | cacaatgcag | agtctccaga | ttttcagctc | 1560 |
| caggcaatga | tccaggctgc | tggcaagcta | gtgctgattg | acaagctgct | gccaaaactg | 1620 |
| aaggctggtg | gccacagggt | gcttatcttt | tcccagatgg | tgcgctgctt | ggacatactg | 1680 |
| gaagactacc | tcattcaaag | acggtaccca | tatgaaagga | tcgacggccg | agtaagaggc | 1740 |
| aacctccgcc | aggcagctat | cgacagattc | tccaaacctg | attctgatag | gtttgttttc | 1800 |
| ctcctgtgta | caagggcagg | aggtttaggc | attaacctca | ctgctgctga | tacctgcatc | 1860 |
| atctttgatt | cagactggaa | tcccaaaat | gacctccagg | ctcaggctag | atgtcataga | 1920 |
| ataggacaga | gcaaatctgt | gaaaatctac | aggctgatta | caagaaattc | ctatgaaagg | 1980 |
| gaaatgttcg | acaaggctag | tttgaaactg | ggcctggata | aagctgtgct | acagtctatg | 2040 |

-continued

```
agtggaagag aaaatgctac caatggggta caacagcttt ccaagaaaga aatagaggat    2100
cttctacgaa aagggccta tggtgcactc atggatgagg aggatgaagg gtctaaattc    2160
tgtgaagaag atattgatca gatcctccta cgtcgaaccc acaccattac cattgagtca    2220
gaagggaaag gttccacatt tgctaaggcc agttttgttg catctggaaa taggacagat    2280
atttccttgg atgatccaaa tttctggcaa aagtgggcta agaaggctga attggatatt    2340
gatgccttaa atgggaggaa caacctggtt attgatactc caagagtgag aaagcagacc    2400
aggctctaca gtgcagtgaa ggaagatgag ctgatggagt tctcagactt ggaaagtgat    2460
tctgaagaaa agccctgtgc aaagccacgg cgtccccagg ataagtcaca gggctatgca    2520
aggagtgaat gtttcagggt ggagaagaat ctgcttgtct atggttgggg acggtggaca    2580
gacattcttt cccacggacg ctataaacgc caactcactg agcaagatgt agaaaccatc    2640
tgcagaacca tcctggtgta ctgtcttaat cattacaaag gggatgagaa tatcaaaagc    2700
ttcatctggg atctgatcac acccacagcg gatggccaga ctcgagcctt ggtcaaccat    2760
tccggtttgt cagctcctgt gccaagggga aggaagggaa agaaggtgaa agcccagagc    2820
acacagccgg tggtgcagga tgccgactgg ctggccagct gcaacccaga tgccctgttc    2880
caggaggaca gctacaagaa acacctgaag catcactgta acaaggtcct gctgcgtgtc    2940
cgcatgctgt actacctaag acaagaagtg ataggagacc aggcggataa gatcttagag    3000
ggtgctgact caagtgaagc cgatgtgtgg atccctgaac cttccatgc tgaagttcct    3060
gcagattggt gggataagga agcagacaaa tccctcttaa ttggagtgtt caaacatggc    3120
tatgagaagt acaactccat gcagctgacc cccgcgctgt gctttctgga acgagtcggt    3180
atgcctgatg ccaaggccat agctgccgag caaagaggaa cagacatgct agcagatggt    3240
ggtgacgggg gagaatttga tagagaagat gaagacccag aatataaacc aaccagaaca    3300
ccgttcaaag atgaaataga tgaatttgca aattctcctt cagaggataa ggaagaatcc    3360
atggaaatac atgccacagg caagcacagt gagagtaatg ctgagttagg ccaactttac    3420
tggcctaaca cttcaacccct gactacacgt ctgcgccggc tcattactgc ctatcagcgc    3480
agctataaaa ggcaacagat gaggcaagag gccctaatga agactgaccg gcgcagacgg    3540
cggcctcgag aggaagtgag agctctggaa gcggaagggg aagctattat atctgagaag    3600
cggcaaaagt ggacaagaag agaagaggct gatttttacc gtgtggtatc cacctttggg    3660
gttattttg accctgtgaa acagcaattt gactggaacc aatttagagc cttttgccagg    3720
cttgacaaaa aatctgatga gagtttggag aaatacttca gttgttttgt ggccatgtgt    3780
aggcgagtat gtcgaatgcc cgtcaagcca gatgatgaac cgcccgacct ctcctccata    3840
attgagccga tcacagagga gcgagcctct cgaactctgt accgcattga gctgctacgg    3900
aagatccgcg agcaggttct ccatcacccc cagctgggag agaggcttaa gctctgccag    3960
ccaagcttgg atctgccaga gtggtgggag tgtggacggc atgaccgaga cttgctggtt    4020
ggtgctgcta acacgggggt cagtcggacg gattatcaca tcctcaatga ccctgagtta    4080
tccttcttgg atgcacataa aaactttgct caaaacagag gggcaggtaa tacatcttcc    4140
ttgaacccac tggcagttgg atttgtccag actcctccag tcatctcatc tgctcatatt    4200
caagatgaga gggtactgga acaagccgaa ggcaaagtgg aggagcctga aacccagct    4260
gccaaggaga aatgtgaggg caaagaagag gaagaagaaa ccgatggcag cgggaaggag    4320
agcaagcagg aatgtgaggc agaggccagc tctgtgaaaa atgaactgaa aggtgttgag    4380
```

```
gtcggcgcag acactgggtc caaatctatt tcagagaaag gttccgaaga ggatgaagag   4440
gaaaagctgg aggatgacga taagtcggaa gagtcttccc agcccgaagc aggagctgtc   4500
tctagaggga agaattttga tgaagaaagc aatgcttcca tgagcactgc tagagatgaa   4560
acccgagatg gattctacat ggaggacgga gatccttcag tagctcagct ccttcatgaa   4620
agaacatttg ccttctcgtt ttggcctaag gatagagtaa tgataaaccg cttagacaac   4680
atctgtgaag cagtgttgaa aggcaaatgg ccagtaaata ggcgccagat gtttgatttc   4740
caaggcctca tcccaggtta cacacccacc acagtggaca gcccttgca gaagaggagc    4800 tttgctgagc tctccatggt cggccaagcc agcattagtg ggagtgagga catcactacg   4860
tctcctcagt tgtcaaagga agatgccctc aacctctctg tccctcgcca gcggaggagg   4920
aggaggagaa aaatcgaaat tgaggccgaa agagctgcca agaggcgaaa tctcatggag   4980
atggttgccc agcttcgaga gtctcaggtg gtctcagaaa atggacaaga aaaagttgta   5040
gatttatcaa aggcctcaag agaggcaaca agctctacct caaatttttc atctctttct   5100
tcaaagttta tcttgcctaa tgtctcaaca ccagtgtctg atgcctttaa gactcaaatg   5160
gaactgctcc aagcaggcct ttcgcgcaca cccacaaggc atctccttaa tggctcccta   5220
gtggatggag agcctcccat gaagaggagg cggggaagga ggaaaaatgt ggagggactt   5280
gatctgcttt tcatgagcca caaacggacg tcattgagtg cagaggatgc tgaggtgacc   5340
aaagcttttg aagaagatat agagaccccca ccaacaagaa acattccttc tcccggacag   5400
ctggacccag acacacggat ccctgttatc aatcttgaag atgggactag ctggtgggg   5460 gaagatgctc ctaaaaataa ggatttagtt gaatggctga agctgcaccc tacttacact   5520
gttgatatgc caagttatgt accaaagaat gcagatgtgc tgttttcctc atttcagaaa   5580
ccgaaacaga aacgacatag atgtcgaaac cctaataaat tggatataaa cactttgaca   5640
ggagaagaaa gggtgcctgt tgtcaataaa cgaaatggga agaagatggg tggagctatg   5700
gcgcctccaa tgaaggatct acccaggtgg ctggaagaaa atcctgaatt tgcagttgct   5760
ccagactgga ctgatatagt taagcagtct ggttttgttc ctgagtcgat gtttgaccgc   5820
cttctcactg ggcctgtagt gcggggagag ggagcgagca gaagaggaag aaggcccaaa   5880
agtgagatcg ccagagcagc c                                             5901
```

<210> SEQ ID NO 2
<211> LENGTH: 485
<212> TYPE: DNA
<213> ORGANISM: Homo sapiens
<220> FEATURE:
<221> NAME/KEY: Misc_feature
<222> LOCATION: (252)..(252)
<223> OTHER INFORMATION: n = a, g, c, or t/u
<220> FEATURE:
<221> NAME/KEY: Misc_feature
<222> LOCATION: (301)..(301)
<223> OTHER INFORMATION: n = a, g, c, or t/u
<220> FEATURE:
<221> NAME/KEY: Misc_feature
<222> LOCATION: (371)..(371)
<223> OTHER INFORMATION: n = a, g, c, or t/u
<220> FEATURE:
<221> NAME/KEY: Misc_feature
<222> LOCATION: (390)..(390)
<223> OTHER INFORMATION: n = a, g, c, or t/u
<220> FEATURE:
<221> NAME/KEY: Misc_feature
<222> LOCATION: (417)..(417)
<223> OTHER INFORMATION: n = a, g, c, or t/u
<220> FEATURE:
<221> NAME/KEY: Misc_feature

```
<222> LOCATION: (434)..(434)
<223> OTHER INFORMATION: n = a, g, c, or t/u
<220> FEATURE:
<221> NAME/KEY: Misc_feature
<222> LOCATION: (437)..(437)
<223> OTHER INFORMATION: n = a, g, c, or t/u
<220> FEATURE:
<221> NAME/KEY: Misc_feature
<222> LOCATION: (442)..(442)
<223> OTHER INFORMATION: n = a, g, c, or t/u
<220> FEATURE:
<221> NAME/KEY: Misc_feature
<222> LOCATION: (449)..(449)
<223> OTHER INFORMATION: n = a, g, c, or t/u
<220> FEATURE:
<221> NAME/KEY: Misc_feature
<222> LOCATION: (452)..(452)
<223> OTHER INFORMATION: n = a, g, c, or t/u
<220> FEATURE:
<221> NAME/KEY: Misc_feature
<222> LOCATION: (460)..(460)
<223> OTHER INFORMATION: n = a, g, c, or t/u
<220> FEATURE:
<221> NAME/KEY: Misc_feature
<222> LOCATION: (461)..(461)
<223> OTHER INFORMATION: n = a, g, c, or t/u
<220> FEATURE:
<221> NAME/KEY: Misc_feature
<222> LOCATION: (476)..(476)
<223> OTHER INFORMATION: n = a, g, c, or t/u

<400> SEQUENCE: 2
ggcgcccctc gctgccccgc gcgctccccg ccgcccccca tgagcgcagc cccgcgcggc      60
ccgggtccgt aggcggcggg gcgccccca tgctgctgca gcccgcgccg tgcgcccga      120 gcgcgggctt cccgcggccc ctggccgccc ccggcgccat gcacttgttc gcagaaggac     180
accacgttca ccaagatctt cgtgggcggc ctgccgtacc acactaccga cgcctcgctc     240
aggaagtact tngagggctt cggcgacatc tgaggaggcc gtggtcatca ccgaccgcca     300
nacgggcaag tcccgcggct acggcttcgt gaccatggcc gaccgggcgg cagctgagag     360
ggcttgcaaa nacccgaacc ccatcatcgn cggccgccag ccaacgtga acctggnata     420 tttgggcgcc aagntcncgg anccttcana cnggctttgn nattggggtg caacanctgc     480
accc                                                                   485

<210> SEQ ID NO 3
<211> LENGTH: 2885
<212> TYPE: DNA
<213> ORGANISM: Homo sapiens

<400> SEQUENCE: 3
ggaattcctc ttgtcgaagt caaaggagcc cacaccaggc ggcctcaacc attccctccc      60
acagcacccc aaatgctggg gagcccacca tgcttctttg gaccagagtt cccctcccca     120
gagcggcccc cctgggacgc ctccctccta caaactgcct ttgcctgggc cctacgacag     180
tcgagacgac ttccccctcc gcaaaacagc ctctgaaccc aacttgaaag tgcgttcaag     240
gctaaaacag aaggtggctg agcggagaag cagtccctc ctgcgtcgca aggatgggac     300
tgttattagc acctttaaga agagagctgt tgagatcaca ggtgccgggc ctggggcgtc     360
gtccgtgtgt aacagcgcac ccggctccgg ccccagctct cccaacagct cccacagcac     420
catcgctgag aatggcttta ctggctcagt ccccaacatc cccactgaga tgctccctca     480
gcaccgagcc ctccctctgg acagctcccc caaccagttc agcctctaca cgtctccttc     540
tctgcccaac atctccctag ggctgcaggc cacggtcact gtcaccaact cacacctcac     600
```

-continued

```
tgcctccccg aagctgtcga cacagcagga ggccgagagg caggccctcc agtccctgcg    660
gcagggtggc acgctgaccg gcaagttcat gagcacatcc tctattcctg gctgcctgct    720
gggcgtggca ctggagggcg acgggagccc ccacgggcat gcctccctgc tgcagcatgt    780
gctgttgctg gagcaggccc ggcagcagag caccctcatt gctgtgccac tccacgggca    840
gtccccacta gtgacgggtg aacgtgtggc caccagcatg cggacggtag gcaagctccc    900
gcggcatcgg cccctgagcc gcactcagtc ctcaccgctg ccgcagagtc cccaggcect    960 gcagcagctg gtcatgcaac aacagcacca gcagttcctg gagaagcaga agcagcagca   1020
gctacagctg ggcaagatcc tcaccaagac aggggagctg cccaggcagc ccaccaccca   1080
ccctgaggag acagaggagg agctgacgga gcagcaggag gtcttgctgg gggagggagc   1140
cctgaccatg ccccgggagg gctccacaga gagtgagagc acacaggaag acctggagga   1200
ggaggacgag gaagaggatg gggaggagga ggaggattgc atccaggtta aggacgagga   1260
gggcgagagt ggtgctgagg aggggcccga cttggaggag cctggtgctg gatacaaaaa   1320
actgttctca gatgcccaac cgctgcaacc tttgcaggtg taccaagcgc ccctcagcct   1380
ggccactgtg ccccaccaag ccctgggccg tacccaatcc tcccctgctg cccctggggg   1440
catgaagaac cccccagacc aacccgtcaa gcacctcttc accacaagtg tggtctacga   1500
cacgttcatg ctaaagcacc agtgcatgtg cgggaacaca cacgtgcacc ctgagcatgc   1560
tggccggatc cagagcatct ggtcccggct gcaggagaca ggcctgctta gcaagtgcga   1620
gcggatccga ggtcgcaaag ccacgctaga tgagatccag acagtgcact ctgaatacca   1680
caccctgctc tatgggacca gtcccctcaa ccggcagaag ctagacagca agaagttgct   1740
cggtcccatc agccagaaga tgtatgctgt gctgccttgt gggggcatcg gggtggacag   1800
tgacaccgtg tggaatgaga tgcactcctc cagtgctgtg cgcatggcag tgggctgcct   1860
gctggagctg gccttcaagg tggctgcagg agagctcaag aatggatttg ccatcatccg   1920 gccccccagga caccacgccg aggaatccac agccatggga ttctgcttct tcaactctgt   1980
agccatcacc gcaaaactcc tacagcagaa gttgaacgtg ggcaaggtcc tcatcgtgga   2040
ctgggacatt caccatggca atggcaccca gcaggcgttc tacaatgacc cctctgtgct   2100
ctacatctct ctgcatcgct atgacaacgg gaacttcttt ccaggctctg ggctcctga    2160 agaggttggt ggaggaccag gcgtggggta caatgtgaac gtggcatgga caggaggtgt   2220 ggacccccc attggagacg tggagtacct tacagccttc aggacagtgg tgatgcccat   2280
tgcccacgag ttctcacctg atgtggtcct agtctccgcc gggtttgatg ctgttgaagg   2340
acatctgtct cctctggggtg ctactctgt caccgccaga tgttttggcc acttgaccag   2400
gcagctgatg accctggcag ggggccgggt ggtgctggcc ctggagggag ccatgactt    2460 gaccgccatc tgtgatgcct ctgaagcttg tgtctcggct ctgctcagtg taaagctgca   2520
gcccttggat gaggcagtct tgcagcaaaa gcccaacatc aacgcagtgg ccacgctaga   2580
gaaagtcatc gagatccaga gcaaacactg gagctgtgtg cagaagttcg ccgctggtct   2640
gggccggtcc ctgcgagggg cccaagcagg tgagaccgaa gaagccgaaa tgtgaacgcc   2700
atggccttgc tgttggtggg ggccgaacag gcccaagctg cggcagcccg ggaacacagc   2760
cccaggccgg cagaggagcc catggagcag gagcctgccc tgtgacgccc cggcccccat   2820
cccctttggg c ttcaccattg tgattttgtt tatttttctct attaaaaaca aaaagttaaa   2880
aattt                                                                2885
```

<210> SEQ ID NO 4
<211> LENGTH: 3876
<212> TYPE: DNA
<213> ORGANISM: Homo sapiens

<400> SEQUENCE: 4

| | | | | | |
|---|---|---|---|---|---|
| atgtttgatt | catggattg | tgagctgaag | ctttctgaat | cagttttccg | acagctcaac | 60 |
| acggccatcg | ccgtatccca | gatgtcctca | ggccagtgcc | gcctggcccc | cctcatccag | 120 |
| gtcatccagg | actgcagcca | cctctaccac | tacacggtca | agctcctgtt | caagctacac | 180 |
| tcttgtctcc | ctgcggacac | cctgcaaggc | cacagggacc | ggttccacga | gcagtttcac | 240 |
| agcctcagga | acttcttccg | cagagcctcc | gacatgctgt | acttcaagcg | gctcatccag | 300 |
| atccccggc | tgcccgaggg | acccctaac | ttcctgcggg | cctcagccct | ggctgagcac | 360 |
| atcaagccgg | tggtggtgat | ccccgaggag | gccccggaag | atgaggagcc | ggagaatctc | 420 |
| attgagatca | gcacagggcc | ccccgcgggg | gagccagtgg | tggtggctga | cctcttcgat | 480 |
| cagacgtttg | daccccccaa | tgggtctgtg | aaggacgaca | gggacctcca | gattgagagc | 540 |
| ttgaagagag | aggtggaaat | gctccgctct | gaactggaga | gatcaagct | ggaggcccag | 600 |
| cggtacatcg | cgcagctgaa | gagccaggtg | aatgcactgg | agggtgagct | ggaggagcag | 660 |
| cggaagcaga | agcagaaggc | cctggtggat | aatgagcagc | tccgccacga | gctggcccag | 720 |
| ctgagggctg | cccagctgga | gggcgagcgg | agccagggcc | tgcgtgagga | ggctgagagg | 780 |
| aaggccagtg | ccacggaggc | gcgctacaac | aagctgaagg | aaaagcacag | tgagctcgtc | 840 |
| catgtgcacg | cggagctgct | cagaaagaac | gcggacacag | ccaagcagct | gacggtgacg | 900 |
| cagcaaagcc | aggaggaggt | ggcgcgggtg | aaggagcagc | tggccttcca | ggtggagcag | 960 |
| gtgaagcggg | agtcggagtt | gaagctagag | gagaagagcc | accagctgga | gaagctcaag | 1020 |
| agggagctgg | aggccaaggc | cggagagctg | gcccgcgcgc | aggaggccct | gagccacaca | 1080 |
| gagcagagca | agtcggagct | gagctcacgg | ctggacacgt | gagtgcgga | gaaggatgct | 1140 |
| ctgagtggag | ctgtgcggca | gcgggaggca | gacctgctgg | cggcgcagag | cctggtgcgc | 1200 |
| gagacagagg | cggcgctgag | ccgggagcag | cagcgcagct | cccaggagca | gggcgagttg | 1260 |
| cagggccggc | tggcagagag | ggagtctcag | gagcagggggc | tgcggcagag | gctgctggac | 1320 |
| gagcagttcg | cagtgttgcg | gggcgctgct | ccgaggccg | cgggcatcct | gcaggatgcc | 1380 |
| gtgagcaagc | tggacgaccc | cctgcacctg | cgctgtacca | gctcccaga | ctacctggtg | 1440 |
| agcagggccc | aggaggcctt | ggatgccgtg | agcaccctgg | aggagggcca | cgcccagtac | 1500 |
| ctgacctcct | tggcagacgc | ctccgccctg | gtggcagctc | tgacccgctt | ctcccacctg | 1560 |
| gctgcggata | ccatcatcaa | tggcggtgcc | acctcgcacc | tggctcccac | cgaccctgcc | 1620 |
| gaccgcctca | tagacacctg | cagggagtgc | gggccccggg | ctctggagct | catggggcag | 1680 |
| ctgcaggacc | agcaggctct | gcggcacatg | caggccagcc | tggtgcggac | acccctgcag | 1740 |
| ggcatccttc | agctgggcca | ggaactgaaa | cccaagagcc | tagatgtgcg | gcaggaggag | 1800 |
| ctgggggccg | tggtcgacaa | ggagatggcg | gccacatccg | cagccattga | agatgctgtg | 1860 |
| cggaggattg | aggacatgat | gaaccaggca | cgccacgcca | gctcggggt | gaagctggag | 1920 |
| gtgaacgaga | ggatcctcaa | ctcctgcaca | gacctgatga | aggctatccg | gctcctggtg | 1980 |
| acgacatcca | ctagcctgca | gaaggagatc | gtggagagcg | gcaggggggc | agccacgcag | 2040 |
| caggaatttt | acgccaagaa | ctcgcgctgg | accgaaggcc | tcatctcggc | ctccaaggct | 2100 |
| gtgggctggg | gagccacaca | gctggtggag | gcagctgaca | aggtggtgct | tcacacgggc | 2160 |

-continued

```
aagtatgagg agctcatcgt ctgctcccac gagatcgcag ccagcacggc ccagctggtg    2220
gcggcctcca aggtgaaggc caacaagcac agcccccacc tgagccgcct gcaggaatgt    2280
tctcgcacag tcaatgagag ggctgccaat gtggtggcct ccaccaagtc aggccaggag    2340
cagattgagg acagagacac catggatttc tccggcctgt ccctcatcaa gctgaagaag    2400
caggagatgg agacgcaggt gcgtgtcctg agctggaga agacgctgga ggctgaacgc    2460
atgcggctgg gggagttgcg gaagcaacac tacgtgctgg ctggggcatc aggcagccct    2520
ggagaggagg tggccatccg gcccagcact gccccccgaa gtgtaaccac caagaaacca    2580
cccctggccc agaagcccag cgtggccccc agacaggacc accagcttga caaaaaggat    2640
ggcatctacc cagctcaact cgtgaactac taggcccccc aggggtccag cagggtggct    2700
ggtgacaggc ctgggcctct gcaactgccc tgacaggacc gagaggcctt gcccctccac    2760
ctggtgccca gcctcccgc ccaccgtct ggatcaatgt cctcaaggcc cctggcccttt    2820 actgagcctg cagggtcctg ggccatgtgg gtggtgcttc tggatgtgag tctcttattt    2880
atctgcagaa ggaactttgg ggtgcagcca ggacccggta ggcctgagcc tcaactcttc    2940
agaaaatagt gttttttaata ttcctcttca gaaaatagtg tttttaatat tccgagctag    3000
agctcttctt cctacgtttg tagtcagcac actgggaaac cgggccagcg tggggctccc    3060
tgccttctgg actcctgaag gtcgtggatg atggaaggc acacagcccg tgccggctga    3120
tgggacgagg gtcaggcatc ctgtctgtgg ccttctgggg caccgattct accaggccct    3180
ccagctgcgt ggtctccgca gaccaggctc tgtgtgggct agaggaatgt cgcccattac    3240
tcctcaggcc tggccctcgg gcctccgtga tgggagcccc caggagggg tcagatgctg    3300 gaaggggccg ctttctgggg agtgaggtga gacatagcgg cccaggcgct gccttcactc    3360
ctggagtttc catttccagc tggaatctgc agccaccccc atttcctgtt ttccattccc    3420
ccgttctggc cgcgcccac tgcccacctg aaggggtggt ttccagccct ccggagagtg    3480
ggcttggccc taggccctcc agctcagcca gaaaaagccc agaaacccag gtgctggacc    3540
agggccctca gggaggggac cctgcggcta gagtgggcta ggccctggct ttgcccgtca    3600
gatttgaacg aatgtgtgtc ccttgagccc aaggagagcg gcaggagggg tgggaccagg    3660 ctggaggac agagccagca gctgccatgc cctcctgctc cccccacccc agccctagcc    3720
ctttagcctt tcaccctgtg ctctggaaag gctaccaaat actggccaag gtcaggagga    3780
gcaaaaatga ccagcacca gcgccttggc tttgtgttag catttcctcc tgaagtgttc    3840
tgttggcaat aaaatgcact ttgactgttt gttgtc                            3876
```

<210> SEQ ID NO 5
<211> LENGTH: 2740
<212> TYPE: DNA
<213> ORGANISM: Homo sapiens

<400> SEQUENCE: 5

```
gcgaaattga ggtttcttgg tattgcgcgt ttctcttcct tgctgactct ccgaatggcc      60
atggactcgt cgcttcaggc ccgcctgttt cccggtctcg ctatcaagat ccaacgcagt     120
aatggtttaa ttcacagtgc caatgtaagg actgtgaact tggagaaatc ctgtgtttca     180
gtggaatggg cagaaggagg tgccacaaag ggcaaagaga ttgattttga tgatgtggct     240
gcaataaacc cagaactctt acagcttctt cccttacatc cgaaggacaa tctgcccttg     300
caggaaaatg taacaatcca gaaacaaaaa cggagatccg tcaactccaa aattcctgct     360
ccaaaagaaa gtcttcgaag ccgctccact cgcatgtcca ctgtctcaga gcttcgcatc     420
```

```
acggctcagg agaatgacat ggaggtggag ctgcctgcag ctgcaaactc ccgcaagcag    480 tttcagttc ctcctgcccc cactaggcct tcctgccctg cagtggctga ataccattg    540 aggatggtca gcgaggagat ggaagagcaa gtccattcca tccgtggcag ctcttctgca    600
aaccctgtga actcagttcg gaggaaatca tgtcttgtga aggaagtgga aaaatgaag    660 aacaagcgag aagagaagaa ggcccagaac tctgaaatga aatgaagag agctcaggag    720 tatgacagta gttttccaaa ctgggaattt gcccgaatga ttaaagaatt tcgggctact    780
ttggaatgtc atccacttac tatgactgat cctatcgaag agcacagaat atgtgtctgt    840
gttaggaaac gcccactgaa taagcaagaa ttggccaaga agaaattga tgtgatttcc    900 attcctagca agtgtctcct cttggtacat gaacccaagt tgaaagtgga cttaacaaag    960
tatctggaga accaagcatt ctgctttgac tttgcatttg atgaaacagc ttcgaatgaa   1020
gttgtctaca ggttcacagc aaggccactg gtacagacaa tctttgaagg tggaaaagca   1080
acttgttttg catatggcca gacaggaagt ggcaagacac atactatggg cggagacctc   1140
tctgggaaag cccagaatgc atccaaaggg atctatgcca tggcctcccg ggacgtcttc   1200
ctcctgaaga atcaaccctg ctaccggaag ttgggcctgg aagtctatgt gacattcttc   1260
gagatctaca atgggaagct gtttgacctg ctcaacaaga aggccaagct gcgcgtgctg   1320
gaggacggca agcaacaggt gcaagtggtg gggctgcagg agcatctggt taactctgct   1380
gatgatgtca tcaagatgct cgacatgggc agcgcctgca gaacctctgg gcagacattt   1440
gccaactcca attcctcccg ctcccacgcg tgcttccaaa ttattcttcg agctaaaggg   1500
agaatgcatg gcaagttctc tttggtagat ctggcaggga atgagcgagg cgcagacact   1560
tccagtgctg accggcagac ccgcatggag ggcgcagaaa tcaacaagag tctcttagcc   1620
ctgaaggagt gcatcagggc cctgggacag aacaaggctc acaccccgtt ccgtgagagc   1680
aagctgacac aggtgctgag ggactccttc attggggaga actctaggac ttgcatgatt   1740
gccacgatct caccaggcat aagctcctgt gaatatactt taaacaccct gagatatgca   1800
gacagggtca aggagctgag cccccacagt gggcccagtg agagcagtt gattcaaatg   1860 gaaacagaag agatggaagc ctgctctaac ggggcgctga ttccaggcaa tttatccaag   1920
gaagaggagg aactgtcttc ccagatgtcc agctttaacg aagccatgac tcagatcagg   1980
gagctggagg agaaggctat ggaagagctc aaggagatca tacagcaagg accagactgg   2040
cttgagctct ctgagatgac cgagcagcca gactatgacc tggagacctt tgtgaacaaa   2100
gcggaatctg ctctggccca gcaagccaag catttctcag ccctgcgaga tgtcatcaag   2160
gccttacgcc tggccatgca gctggaagag caggctagca gacaaataag cagcaagaaa   2220
cggccccagt gacgactgca aataaaaatc tgtttggttt gacacccagc ctcttccctg   2280 gccctccca gagaactttg ggtacctggt gggtctaggc agggtctgag ctgggacagg   2340
ttctggtaaa tgccaagtat gggggcatct gggcccaggg cagctgggga ggggtcaga   2400 gtgacatggg acactccttt tctgttcctc agttgtcgcc ctcacgagag aaggagctc   2460 ttagttaccc ttttgtgttg cccttctttc catcaagggg aatgttctca gcatagagct   2520
ttctccgcag catcctgcct gcgtggactg gctgctaatg gagagctccc tggggttgtc   2580
ctggctctgg ggagagagac ggagccttta gtacagctat ctgctggctc taaaccttct   2640
acgcctttgg gccgagcact gaatgtcttg tactttaaaa aaatgttctct gagacctctt   2700 tctactttac tgtctcccta gagtcctaga ggatccctac                        2740
```

```
<210> SEQ ID NO 6
<211> LENGTH: 2569
<212> TYPE: DNA
<213> ORGANISM: Homo sapiens
<220> FEATURE:
<221> NAME/KEY: Misc_feature
<222> LOCATION: (2237)..(2237)
<223> OTHER INFORMATION: n = a, c, g,  or t/u
<220> FEATURE:
<221> NAME/KEY: Misc_feature
<222> LOCATION: (2260)..(2260)
<223> OTHER INFORMATION: n = a, c, g,  or t/u
<220> FEATURE:
<221> NAME/KEY: Misc_feature
<222> LOCATION: (2305)..(2305)
<223> OTHER INFORMATION: n = a, c, g,  or t/u
<220> FEATURE:
<221> NAME/KEY: Misc_feature
<222> LOCATION: (2315)..(2315)
<223> OTHER INFORMATION: n = a, c, g,  or t/u
<220> FEATURE:
<221> NAME/KEY: Misc_feature
<222> LOCATION: (2355)..(2355)
<223> OTHER INFORMATION: n = a, c, g,  or t/u
<220> FEATURE:
<221> NAME/KEY: Misc_feature
<222> LOCATION: (2420)..(2420)
<223> OTHER INFORMATION: n = a, c, g,  or t/u
<220> FEATURE:
<221> NAME/KEY: Misc_feature
<222> LOCATION: (2421)..(2421)
<223> OTHER INFORMATION: n = a, c, g,  or t/u
<220> FEATURE:
<221> NAME/KEY: Misc_feature
<222> LOCATION: (2423)..(2423)
<223> OTHER INFORMATION: n = a, c, g,  or t/u
<220> FEATURE:
<221> NAME/KEY: Misc_feature
<222> LOCATION: (2490)..(2490)
<223> OTHER INFORMATION: n = a, c, g,  or t/u
<220> FEATURE:
<221> NAME/KEY: Misc_feature
<222> LOCATION: (2523)..(2523)
<223> OTHER INFORMATION: n = a, c, g,  or t/u

<400> SEQUENCE: 6
aagagtaaaa gctactcttt cagagagaaa aataggagat tcatgtgaca aagatttgcc      60
tctgaaattt tgtgagttcc cacagaagac tataatgcct ggatttaaaa caactgtata     120
tgtttctcat ataaatgacc tttcagactt ttatgttcaa ctaatagaag atgaagctga     180
aattagtcat ctttcagaga gattaaacag tgttaaaaca aggcccgaat attatgtagg     240
tccacctttg caaagaggag atatgatatg tgctgttttc ccagaagata atttatggta     300
tcgtgctgtg atcaaggagc aacaacccaa tgaccttctc tctgtgcagt ttatagatta     360
tggcaatgtt tctgtggttc atactaacaa aataggtagg cttgaccttg ttaatgcaat     420
attgccgggg ttgtgcattc attgctcctt gcagggattt gaggttcctg acaataaaaa     480
ttctaagaaa atgatgcatt actttttccca acgaccagc gaggctgcaa taagatgtga     540
atttgttaaa tttcaagaca gatgggaagt tattcttgct gatgaacatg ggatcatagc     600
agatgatatg attagcaggt atgctctcag tgaaaaatct caagtagaac tttctaccca     660
agtaattaaa agtgccagtt caaagtctgt taacaaatca gacattgaca cttcagtatt     720
tcttaactgg tataatccag aaaaaaaaat gataagagct tatgccactg tgatagatgg     780
acctgagtac ttttggtgtc agtttgctga tacggagaaa cttcagtgtt tagaagtaga     840
agtacagact gctggagaac aggtagcaga caggagaaat tgtatcccat gtccttatat     900
tggagatcct tgtatagtaa gatacagaga agatggacat tattataggg cacttatcac     960
```

```
taatatttgt gaagattatc ttgtatctgt caggcttgtg gactttggaa acattgaaga    1020
ctgtgtggac ccaaaagcac tctgggccat tccttctgaa cttctgtcgg ttcccatgca    1080
agcctttcca tgttgcctct cagggtttaa catttcagaa ggattatgtt ctcaagaggg    1140
aaatgactat ttctatgaaa taataacaga agatgtgttg gaaataacaa tactagaaat    1200
cagaagggat gtttgtgata tcccttagc aattgttgac ttgaaaagca aggtaaaag     1260 tattaatgag aaaatggaga aatattctaa gactggtatt aaaagtgctc ttccctatga    1320
aaatattgac tcagagataa agcagactct tgggtcctac aatcttgatg taggacttaa    1380
gaaattaagt aataaagctg tacaaaataa aatatatatg gaacaacaga cagatgagct    1440
tgctgaaata actgaaaaag atgtaaacat tattggaacc aaaccaagta acttccgtga    1500
ccctaaaact gataacattt gtgaagggtt tgaaaacccc tgcaaagata aaattgatac    1560
tgaggaactg gaaggtgaat tagagtgcca tctggttgac aaagcagagt ttgatgataa    1620 ataacctgatt acaggattta acacattact accacatgct aatgaaacaa aggagatact    1680
agaactgaat tcacttgagg tgccgctttc tcctgatgat gaatcaaaag aattcttaga    1740
actggaatct attgagttac agaattctct ggtggtggat gaagaaaaag gggagctaag    1800
cccggtgcca ccgaatgtgc cactctccca agagtgtgtc acaaaaggcg ccatggagct    1860
atttacactg cagcttcctc tcagctgtga agctgagaaa cagccagaac tagaactacc    1920
tacagcccag ctgcctttag atgacaagat ggatcctttg tctttaggag ttagtcagaa    1980
agcacaggaa tccatgtgta ctgaggacat gagaaagtca agttgtgtag aatcttttga    2040
tgaccagcgc aggatgtcat tgcatctaca tggagcagat tgtgatccta aaacacagaa    2100
tgaaatgaat atatgtgaag aagaatttgt agagtataaa acagggatg ccatttcggc     2160 attgatgcct ttttctctga ggaagaaagc agtgatggaa gcaagcacaa taatggttta    2220
ccagatcata tttcagntca attacagaac acctacactn tgaaagcctt tactgttgga    2280
tctaaatgtg ttgtgtggtc aagtntaaga aacanatggt ctaaatgtga gattttagaa    2340
acagctgaag aaggnacaag ggttttgaac ctttcaaatg gtatggagga gatagtgaac    2400
cctgagaatg tctggaatgn nanacccaaa ttggataaga gtccacctga gaaagggggt    2460
ttggaggtga tggagattta accgtggatn tatagctgtg gccaatcagt cagaagctgc    2520
ccntgaacaa gtggcatctt acgcagacca acagagtatt tgagaaaat               2569
```

<210> SEQ ID NO 7
<211> LENGTH: 1997
<212> TYPE: DNA
<213> ORGANISM: Homo sapiens
<220> FEATURE:
<221> NAME/KEY: Misc_feature
<222> LOCATION: (105)..(105)
<223> OTHER INFORMATION: n = a, g, c, or t/u
<220> FEATURE:
<221> NAME/KEY: Misc_feature
<222> LOCATION: (132)..(132)
<223> OTHER INFORMATION: n = a, g, c, or t/u
<220> FEATURE:
<221> NAME/KEY: Misc_feature
<222> LOCATION: (151)..(151)
<223> OTHER INFORMATION: n = a, g, c, or t/u
<220> FEATURE:
<221> NAME/KEY: Misc_feature
<222> LOCATION: (209)..(209)
<223> OTHER INFORMATION: n = a, g, c, or t/u
<220> FEATURE:
<221> NAME/KEY: Misc_feature
<222> LOCATION: (221)..(221)

```
<223> OTHER INFORMATION: n = a, g, c, or t/u
<220> FEATURE:
<221> NAME/KEY: Misc_feature
<222> LOCATION: (462)..(462)
<223> OTHER INFORMATION: n = a, g, c, or t/u
<220> FEATURE:
<221> NAME/KEY: Misc_feature
<222> LOCATION: (542)..(542)
<223> OTHER INFORMATION: n = a, g, c, or t/u
<220> FEATURE:
<221> NAME/KEY: Misc_feature
<222> LOCATION: (625)..(625)
<223> OTHER INFORMATION: n = a, g, c, or t/u
<220> FEATURE:
<221> NAME/KEY: Misc_feature
<222> LOCATION: (642)..(642)
<223> OTHER INFORMATION: n = a, g, c, or t/u
<220> FEATURE:
<221> NAME/KEY: Misc_feature
<222> LOCATION: (659)..(659)
<223> OTHER INFORMATION: n = a, g, c, or t/u
<220> FEATURE:
<221> NAME/KEY: Misc_feature
<222> LOCATION: (663)..(663)
<223> OTHER INFORMATION: n = a, g, c, or t/u
<220> FEATURE:
<221> NAME/KEY: Misc_feature
<222> LOCATION: (666)..(666)
<223> OTHER INFORMATION: n = a, g, c, or t/u
<220> FEATURE:
<221> NAME/KEY: Misc_feature
<222> LOCATION: (672)..(672)
<223> OTHER INFORMATION: n = a, g, c, or t/u
<220> FEATURE:
<221> NAME/KEY: Misc_feature
<222> LOCATION: (675)..(675)
<223> OTHER INFORMATION: n = a, g, c, or t/u
<220> FEATURE:
<221> NAME/KEY: Misc_feature
<222> LOCATION: (686)..(686)
<223> OTHER INFORMATION: n = a, g, c, or t/u
<220> FEATURE:
<221> NAME/KEY: Misc_feature
<222> LOCATION: (693)..(693)
<223> OTHER INFORMATION: n = a, g, c, or t/u
<220> FEATURE:
<221> NAME/KEY: Misc_feature
<222> LOCATION: (695)..(695)
<223> OTHER INFORMATION: n = a, g, c, or t/u
<220> FEATURE:
<221> NAME/KEY: Misc_feature
<222> LOCATION: (724)..(724)
<223> OTHER INFORMATION: n = a, g, c, or t/u
<220> FEATURE:
<221> NAME/KEY: Misc_feature
<222> LOCATION: (778)..(778)
<223> OTHER INFORMATION: n = a, g, c, or t/u
<220> FEATURE:
<221> NAME/KEY: Misc_feature
<222> LOCATION: (872)..(872)
<223> OTHER INFORMATION: n = a, g, c, or t/u
<220> FEATURE:
<221> NAME/KEY: Misc_feature
<222> LOCATION: (979)..(979)
<223> OTHER INFORMATION: n = a, g, c, or t/u
<220> FEATURE:
<221> NAME/KEY: Misc_feature
<222> LOCATION: (1146)..(1146)
<223> OTHER INFORMATION: n = a, g, c, or t/u
<220> FEATURE:
<221> NAME/KEY: Misc_feature
<222> LOCATION: (1609)..(1609)
<223> OTHER INFORMATION: n = a, g, c, or t/u
<220> FEATURE:
<221> NAME/KEY: Misc_feature
<222> LOCATION: (1875)..(1875)
<223> OTHER INFORMATION: n = a, g, c, or t/u

<400> SEQUENCE: 7
```

-continued

```
gggctgggga agatggcggt ggctggggcg gtgtccgggg agccgctggt gcactggtgc      60
acccagcagt tgcggaagac tttcggcctg gatgtcagcg agganatcat tcagtacgtt     120
ttgtcaattg anagtgctga agagatacga naatatgtta ctgatctcct ccaggggaaa     180
tgaaggcaaa aaaggtcaat tcatacaana acttataacc naatggcaaa agaatgatca     240
ggagttgatt tcggatcctt tgcagcagtg cttcaaaaaa gatgaaattt tagatgggca     300
gaaatcaggc gaccatctaa agcggggtat gaagaaaggg agaaacagac aggaagttcc     360
tgcatttact gaacctgaca cgactgcaga ggttaaaaca cttttgattg gccaaggcac     420
aagagaacag caactccgta aagaagaaga caaagtttgt cnatttatac acaagagagg     480
gacaggacag gcttgcagtc ctgctccctg gtcgtcaccc ttgtgattgc ctgggccaga     540
ancacaagct catcaataac tgtctgatct gtgggcgcat tgtctgtgaa caagaaggct     600
caggcccttg cttattctgt ggcantctgg tgtgtactct tnaggaacaa gatattttnc     660
agngtnactc anacnaaagc cagaanctgc tananaaact catgtcagga gtggacaatt     720
ctgnaaatgt ggacatctct accaaggacc ttcttcctca tcaagaattg cgaattangt     780
ctggtctgga gaaggctatc aagcataaag acaaactgtt agagtttgac agaactagta     840
ttcgaaggac ccaagtcatt gatgatgagt cngattactt tgccagtgat tctaaccaat     900
ggttgtccaa acttgagcgg gaaaccttgc agaagcgaga ggaggagctg agagaacttc     960
gacacgcctc tcgactttnt aagaagttca ccattgactt tgcaggaagg aagatcctgg    1020
aagaagaaaa ttcactagca gagtatcata gcagactaga tgagacaata caggccattg    1080
ccaatggaac cttgaaccag ccactgacca aattggatag atcttctgaa gagcctttgg    1140
gagttntggt aaatcccaac atgtaccagt cccctcccca gtgggttgac cacacaggtg    1200
cagcctcaca gaagaaggct ttccgttctt caggatttgg actagagttc aactcatttc    1260
agcaccagct gcgaatccag gatcaagaat ttcaggaagg ctttgatggt ggctggtgcc    1320
tctctgtaca tcagccctgg gcttctctgc ttgtcagagg gattaaaagg gtggagggca    1380
gatcctggta caccccccac agaggacgac tttggatagc agccacagct aaaaaaccct    1440
cccctcaaga gtctcagaa ctccaggcta catatcgtct tcttcgtggg aaagatgtgg     1500
aatttcctaa tgactatccg tcaggttgtc ttctgggctg tgtggaccta attgactgct    1560
tgtcccagaa gcaatttaag gagcagtttc cagacatcag tcaagaatnt gattctccat    1620 ttgtttcat ctgcaaaaat cctcaggaaa tggttgtgaa gtttcctatt aaaggaaatc    1680 caaaatctg gaaattggat tccaagatcc atcaaggagc aaagaagggg ttaatgaagc    1740
agaataaagc tgtctgaccc aggagaaaag gaactataca gcatagtgga gttttgtgta    1800
ctaaaattgc tatctactgg tcctttggaa ttgaagtagt agaaacctaa aggcttggcg    1860
tcaggcttga atatntcaga acttaaactc ttaccaaaat ctgtatattt tcttaagga     1920 gtgggattcc tactttatgt aatgggtcg aaatctttga acacattatt tataaaaacc     1980
tgtttaaaaa ttctaaa                                                    1997
```

<210> SEQ ID NO 8
<211> LENGTH: 1087
<212> TYPE: DNA
<213> ORGANISM: Homo sapiens

<400> SEQUENCE: 8

```
aagatgatgc ctagtaaatt acagaagaac aaacagagac tgcgaaacga tcctctcaat      60
```

```
caaaataagg gtaaaccaga cttgaataca acattgccaa ttagacaaac agcatcaatt      120
ttcaaacaac cggtaaccaa agtcacaaat catcctagta ataaagtgaa atcagaccca      180
caacgaatga atgaacagcc acgtcagctt ttctgggaga agaggctaca aggacttagt      240
gcatcagatg taacagaaca aattataaaa accatggaac tacccaaagg tcttcaagga      300
gttggtccag gtagcaatga tgagaccctt ttatctgctg ttgccagtgc tttgcacaca      360
agctctgcgc caatcacagg gcaagtctcc gctgctgtgg aaaagaaccc tgctgtttgg      420
cttaacacat ctcaacccct ctgcaaagct tttattgtca cagatgaaga catcaggaaa      480
caggaagagc gagtacagca agtacgcaag aaattggaag aagcactgat ggcagacatc      540
ttgtcgcgag ctgctgatac agaagagatg atattgaaa tggacagtgg agatgaagcc       600
taagaatatg atcaggtaac tttcgaccga ctttccccaa gagaaaattc ctagaaattg      660
aacaaaaatg tttccactgg cttttgcctg taagaaaaaa aatgtacccg agcacataga      720
gctttttaat agcactaacc aatgcctttt tagatgtatt tttgatgtat atatctatta      780
ttcaaaaaat catgtttatt ttgagtccta ggacttaaaa ttagtctttt gtaatatcaa      840
gcaggaccct aagatgaagc tgagcttttg atgccaggtg caatttactg gaaatgtagc      900
acttacgtaa aacatttgtt tcccccacag ttttaataag aacagatcag gaattctaaa      960
taaatttccc agttaaagat tattgtgact tcactgtata taaacatatt tttatacttt     1020
attgaaaggg gacacctgta cattcttcca tcgtcactgt aaagacaaat aaatgattat     1080
attcaca                                                               1087

<210> SEQ ID NO 9
<211> LENGTH: 1760
<212> TYPE: DNA
<213> ORGANISM: Homo sapiens

<400> SEQUENCE: 9 gtcgacccctt tccaccctg gaagatggaa ataaacctgc gtgtgggtgg agtgttagga      60
caaaaaaaaa aaaaaaaaag tctagagcca ccgtccaggg agcaggtagc tgctgggctc      120
cggggacact ttgcgttcgg gctgggagcg tgctttccac gacggtgaca cgcttccctg      180
gattggcagc cagactgcct tccgggtcac tgccatggag gagccgcagt cagatcctag      240
cgtcgagccc cctctgagtc aggaaacatt ttcagaccta tggaaactac ttcctgaaaa      300
caacgttctg tccccttgc cgtcccaagc aatggatgat tgatgctgt ccccggacga       360 tattgaacaa tggttcactg aagacccagg tccagatgaa gctcccagaa tgccagaggc      420 tgctccccc gtggcccctg caccagcagc tcctacaccg gcggcccctg caccagcccc      480
ctcctggccc ctgtcatctt ctgtcccttc ccagaaaacc taccagggca gctacggttt      540
ccgtctgggc ttcttgcatt ctgggacagc caagtctgtg acttgcacgt actcccctgc      600
cctcaacaag atgttttgcc aactggccaa gacctgccct gtgcagctgt gggttgattc      660
cacacccccg cccggcaccc gcgtccgcgc catggccatc tacaagcagt cacagcacat      720
gacggaggtt gtgaggcgct gcccccacca tgagcgctgc tcagatagcg atggtctggc      780
ccctcctcag catcttatcc gagtggaagg aaatttgcgt gtggagtatt tggatgacag      840
aaacactttt cgacatagtg tggtggtgcc ctgtgagccg cctgaggttg gctctgactg      900
taccaccatc cactacaact acatgtgtaa cagttcctgc atgggcggca tgaaccggag      960
gcccatcctc accatcatca cactggaaga ctccagtggt aatctactgg gacgaacag      1020 ctttgaggtg catgtttgtg cctgtcctgg gagagaccgg cgcacagagg aagagaatct     1080
```

| ccgcaagaaa | gggagcctc | accacgagct | gccccaggg | agcactaagc | gagcactgcc | 1140 |
| caacaacacc | agctcctctc | cccagccaaa | gaagaaacca | ctggatggag | aatatttcac | 1200 |
| ccttcagatc | cgtgggcgtg | agcgcttcga | gatgttccga | gagctgaatg | aggccttgga | 1260 |
| actcaaggat | gcccaggctg | ggaaggagcc | aggggggagc | agggctcact | ccagccacct | 1320 |
| gaagtccaaa | aagggtcagt | ctacctcccg | ccataaaaaa | ctcatgttca | agacagaagg | 1380 |
| gcctgactca | gactgacatt | ctccacttct | tgttccccac | tgacagcctc | ccaccccat | 1440 |
| ctctccctcc | cctgccattt | tgggttttgg | gtctttgaac | ccttgcttgc | aataggtgtg | 1500 |
| cgtcagaagc | acccaggact | tccatttgct | ttgtcccggg | gctccactga | acaagttggc | 1560 |
| ctgcactggt | gttttgttgt | ggggaggagg | atggggagta | ggacatacca | gcttagattt | 1620 |
| taaggttttt | actgtgaggg | atgtttggga | gatgtaagaa | atgttcttgc | agttaagggt | 1680 |
| tagtttacaa | tcagccacat | tctaggtagg | gacccacttc | accgtactaa | ccagggaagc | 1740 |
| tgtccctcac | tgttgaattc | | | | | 1760 |

<210> SEQ ID NO 10
<211> LENGTH: 1953
<212> TYPE: DNA
<213> ORGANISM: Homo sapiens

<400> SEQUENCE: 10

| acgcctgcca | ggagcaagcc | gaagagccag | ccggccggcg | cactccgact | ccgagcagtc | 60 |
| tctgtccttc | gacccgagcc | ccgcgccctt | tccgggaccc | ctgccccgcg | ggcagcgctg | 120 |
| ccaacctgcc | ggccatggag | accccgtccc | agcggcgcgc | cacccgcagc | ggggcgcagg | 180 |
| ccagctccac | tccgctgtcg | cccacccgca | tcacccggct | gcaggagaag | gaggacctgc | 240 |
| aggagctcaa | tgatcgcttg | gcggtctaca | tcgaccgtgt | gcgctcgctg | gaaacggaga | 300 |
| acgcagggct | gcgccttcgc | atcaccgagt | ctgaagaggg | ggtcagccgc | gaggtgtccg | 360 |
| gcatcaaggc | cgcctacgag | gccgagctcg | gggatgcccg | caagacccct | gactcagtag | 420 |
| ccaaggagcg | cgcccgcctg | cagctggagc | tgagcaaagt | gcgtgaggag | tttaaggagc | 480 |
| tgaaagcgcg | caataccaag | aaggagggtg | acctgatagc | tgctcaggct | cggctgaagg | 540 |
| acctggaggc | tctgctgaac | tccaaggagg | ccgcactgag | cactgctctc | agtgagaagc | 600 |
| gcacgctgga | gggcgagctg | catgatctgc | ggggccaggt | ggccaagctt | gaggcagccc | 660 |
| taggtgaggc | caagaagcaa | cttcaggatg | agatgctgcg | gcgggtggat | gctgagaaca | 720 |
| ggctgcagac | catgaaggag | gaactggact | tccagaagaa | catctacagt | gaggagctgc | 780 |
| gtgagaccaa | gcgccgtcat | gagacccgac | tggtggagat | tgacaatggg | aagcagcgtg | 840 |
| agtttgagag | ccggctggcg | gatgcgctgc | aggaactgcg | ggcccagcat | gaggaccagg | 900 |
| tggagcagta | taagaaggag | ctggagaaga | cttattctgc | caagctggac | aatgccaggc | 960 |
| agtctgctga | gaggaacagc | aacctggtgg | gggctgccca | cgaggagctg | cagcagtcgc | 1020 |
| gcatccgcat | cgacagcctc | tctgcccagc | tcagccagct | ccagaagcag | ctggcagcca | 1080 |
| aggaggcgaa | gcttcgagac | ctggaggact | cactggcccg | tgagcgggac | accagccggc | 1140 |
| ggctgctggc | ggaaaaggag | cgggagatgg | ccgagatgcg | ggcaaggatg | cagcagcagc | 1200 |
| tggacgagta | ccaggagctt | ctggacatca | agctggccct | ggacatggag | atccacgcct | 1260 |
| accgcaagct | cttggagggc | gaggaggaga | ggctacgcct | gtcccccagc | cctacctcgc | 1320 |
| agcgcagccg | tggccgtgct | tcctctcact | catcccagac | acagggtggg | ggcagcgtca | 1380 |

-continued

| | |
|---|---|
| ccaaaaagcg caaactggag tccactgaga gccgcagcag cttctcacag cacgcacgca | 1440 |
| ctagcgggcg cgtggccgtg gaggaggtgg atgaggaggg caagtttgtc cggctgcgca | 1500 |
| acaagtccaa tgaggaccag tccatgggca attggcagat caagcgccag aatggagatg | 1560 |
| atcccttgct gacttaccgg ttcccaccaa agttcaccct gaaggctggg caggtggtga | 1620 |
| cgatctgggc tgcaggagct ggggccaccc acagccccc taccgacctg gtgtggaagg | 1680 |
| cacagaacac ctggggctgc gggaacagcc tgcgtacggc tctcatcaac tccactgggg | 1740 |
| aagaagtggc catgcgcaag ctggtgcgct cagtgactgt ggttgaggac gacgaggatg | 1800 |
| aggatggaga tgacctgctc catcaccacc acgtgagtgg tagccgccgc tgaggccgag | 1860 |
| cctgcactgg ggccaccagc caggcctggg ggcagcctct ccccagcctc cccgtgccaa | 1920 |
| aaatctttc attaaagaat gttttggaac ttt | 1953 |

<210> SEQ ID NO 11
<211> LENGTH: 6018
<212> TYPE: DNA
<213> ORGANISM: Homo sapiens

<400> SEQUENCE: 11

| | |
|---|---|
| gctgcctccg ccgccgcggg gcagccgggg ggcagggagc ccagcgaggg gcgcgcgtgg | 60 |
| gcgcggccat gggactgcgc cggatccggt gacagcaggg agccaagcgg cccgggccct | 120 |
| gagcgcgtct tctccggggg gcctcgccct cctgctcgcg gggccggggc tcctgctccg | 180 |
| gttgctggcg ctgttgctgg ctgtggcggc ggccaggatc atgtcgggtc gccgctgcgc | 240 |
| cggcggggga gcggcctgcg cgagcgccgc ggccgaggcc gtggagccgg ccgcccgaga | 300 |
| gctgttcgag gcgtgccgca acggggacgt ggaacgagtc aagaggctgg tgacgcctga | 360 |
| gaaggtgaac agccgcgaca cggcgggcag gaaatccacc ccgctgcact cgccgcagg | 420 |
| ttttgggcgg aaagacgtag ttgaatattt gcttcagaat ggtgcaaatg tccaagcacg | 480 |
| tgatgatggg ggccttattc ctcttcataa tgcatgctct tttggtcatg ctgaagtagt | 540 |
| caatctcctt ttgcgacatg gtgcagaccc caatgctcga gataattgga attatactcc | 600 |
| tctccatgaa gctgcaatta aggaaagat tgatgtttgc attgtgctgt tacagcatgg | 660 |
| agctgagcca accatccgaa atacagatgg aaggacagca ttggatttag cagatccatc | 720 |
| tgccaaagca gtgcttactg gtgaatataa gaaagatgaa ctcttagaaa gtgccaggag | 780 |
| tggcaatgaa gaaaaaatga tggctctact cacaccatta aatgtcaact gccacgcaag | 840 |
| tgatggcaga aagtcaactc cattacattt ggcagcagga tataacagag taaagattgt | 900 |
| acagctgtta ctgcaacatg gagctgatgt ccatgctaaa gataaaggtg atctggtacc | 960 |
| attacacaat gcctgttctt atggtcatta tgaagtaact gaacttttgg tcaagcatgg | 1020 |
| tgcctgtgta aatgcaatgg acttgtggca attcactcct cttcatgagg cagcttctaa | 1080 |
| gaacagggtt gaagtatgtt ctcttctctt aagttatggt gcagacccaa cactgctcaa | 1140 |
| ttgtcacaat aaaagtgcta tagacttggc tcccacacca cagttaaaag aaagattagc | 1200 |
| atatgaattt aaaggccact cgttgctgca agctgcacga gaagctgatg ttactcgaat | 1260 |
| caaaaaacat ctctctctgg aaatggtgaa tttcaagcat cctcaaacac atgaaacagc | 1320 |
| attgcattgt gctgctgcat ctccatatcc caaagaaag caaatatgtg aactgttgct | 1380 |
| aagaaaagga gcaaacatca atgaaaagac taaagaattc ttgactcctc tgcacgtggc | 1440 |
| atctgagaaa gctcataatg atgttgttga agtagtggtg aaacatgaag caaaggttaa | 1500 |
| tgctctggat aatcttggtc agacttctct acacagagct gcatattgtg gtcatctaca | 1560 |

-continued

```
aacctgccgc ctactcctga gctatgggtg tgatcctaac attatatccc ttcagggctt      1620
tactgcttta cagatgggaa atgaaaatgt acagcaactc ctccaagagg gtatctcatt      1680
aggtaattca gaggcagaca gacaattgct ggaagctgca aaggctggag atgtcgaaac      1740
tgtaaaaaaa ctgtgtactg ttcagagtgt caactgcaga gacattgaag ggcgtcagtc      1800
tacaccactt cattttgcag ctgggtataa cagagtgtcc gtggtggaat atctgctaca      1860
gcatggagct gatgtgcatg ctaaagataa aggaggcctt gtacctttgc acaatgcatg      1920
ttcttatgga cattatgaag ttgcagaact tcttgttaaa catggagcag tagttaatgt      1980
agctgattta tggaaattta cacctttaca tgaagcagca gcaaaaggaa aatatgaaat      2040
ttgcaaactt ctgctccagc atggtgcaga ccctacaaaa aaaaacaggg atggaaatac      2100
tcctttggat cttgttaaag atggagatac agatattcaa gatctgctta ggggagatgc      2160
agctttgcta gatgctgcca agaagggttg tttagccaga gtgaagaagt tgtcttctcc      2220
tgataatgta aattgccgcg atacccaagg cagacattca acacctttac atttagcagc      2280
tggttataat aatttagaag ttgcagagta tttgttacaa cacggagctg atgtgaatgc      2340
ccaagacaaa ggaggactta ttcctttaca taatgcagca tcttacgggc atgtagatgt      2400
agcagctcta ctaataaagt ataatgcatg tgtcaatgcc acggacaaat gggctttcac      2460 accctttgcac gaagcagccc aaaagggacg aacacagctt tgtgctttgt tgctagccca      2520
tggagctgac ccgactctta aaaatcagga aggacaaaca cctttagatt tagtttcagc      2580
agatgatgtc agcgctcttc tgacagcagc catgccccca tctgctctgc cctcttgtta      2640
caagcctcaa gtgctcaatg gtgtgagaag cccaggagcc actgcagatg ctctctcttc      2700
aggtccatct agcccatcaa gcctttctgc agccagcagt cttgacaact tatctgggag      2760 ttttcagaa ctgtcttcag tagttagttc aagtggaaca gagggtgctt ccagtttgga      2820
gaaaaaggag gttccaggag tagattttag cataactcaa ttcgtaagga atcttggact      2880
tgagcaccta atggatatat ttgagagaga acagatcact ttggatgtat tagttgagat      2940
ggggcacaag gagctgaagg agattggaat caatgcttat ggacataggc acaaactaat      3000
taaaggagtc gagagactta tctccggaca acaaggtctt aacccatatt taactttgaa      3060
cacctctggt agtggaacaa ttcttataga tctgtctcct gatgataaag agtttcagtc      3120
tgtggaggaa gagatgcaaa gtacagttcg agagcacaga gatggaggtc atgcaggtgg      3180
aatcttcaac agatacaata ttctcaagat tcagaaggtt tgtaacaaga actatgggaa      3240
aagatacact caccggagaa aagaagtttc tgaagaaaac cacaaccatg ccaatgaacg      3300
aatgctattt catgggtctc cttttgtgaa tgcaattatc cacaaaggct ttgatgaaag      3360
gcatgcgtac ataggtggta tgtttggagc tggcatttat tttgctgaaa actcttccaa      3420
aagcaatcaa tatgtatatg gaattggagg aggtactggg tgtccagttc acaaagacag      3480
atcttgttac atttgccaca ggcagctgct cttttgccgg gtaaccttgg gaaagtcttt      3540
cctgcagttc agtgcaatga aaatggcaca ttctcctcca ggtcatcact cagtcactgg      3600
taggcccagt gtaaatggcc tagcattagc tgaatatgtt atttacagag gagaacaggc      3660
ttatcctgag tatttaatta cttaccagat tatgaggcct gaaggtatgg tcgatggata      3720
aatagttatt ttaagaaact aattccactg aacctaaaat catcaaagca gcagtggcct      3780
ctacgtttta ctccttttgct gaaaaaaaat catcttgccc acaggcctgt ggcaaaagga      3840
taaaaatgtg aacgaagttt aacattctga cttgataaag ctttaataat gtacagtgtt      3900
```

```
ttctaaatat tccctgtttt ttcagcactt taacagatgc cattccaggt taaactgggt    3960
tgtctgtact aaattataaa cagagttaac ttgaacccttt tatatgttat gcattgattc    4020
taacaaactg taatgccctc aacagaacta attttactaa tacaatactg tgttctttaa    4080
aacacagcat ttacactgaa tacaatttca tttgtaaaac tgtaaataag agcttttgta    4140
ctagcccagt atttatttac attgctttgt aatataaatc tgttttagaa ctgcagcggt    4200
ttacaaaatt ttttcatatg tattgttcat ctatacttca tcttacatcg tcatgattga    4260
gtgatcttta catttgattc cagaggctat gttcagttgt tagttgggaa agattgagtt    4320
atcagattta atttgccgat gggagccttt atctgtcatt agaaatcttt ctcatttaag    4380
aacttatgaa tatgctgaag atttaatttg tgatacccttt gtatgtatga gacacattcc    4440
aaagagctct aactatgata ggtcctgatt actaaagaag cttctttact ggcctcaatt    4500
tctagctttc atgttggaaa attttctgca gtccttctgt gaaaattaga gcaaagtgct    4560
cctgtttttt agagaaacta aatcttgctg ttgaacaatt attgtgttct tttcatggaa    4620
cataagtagg atgttaacat tccagggtg ggaagggtaa tcctaaatca tttcccaatc    4680
tattctaatt accttaaatc taagggggaa aaaaaaaatc acaaacagga ctgggtagtt    4740
ttttatccta agtatatttt ttcctgttct ttttacttgg ttttattgct gtatttatag    4800
ccaatctata catcatgggt aaacttaacc cagaactata aaatgtagtt gtttcagtcc    4860
ccttcaggcc tcctgaatgg gcaagtgcag tgaaacaggt gcttcctgct cctgggtttt    4920
ctctccatga tgttatgccc aattggaaat atgctgtcag tttgtgcacc atatggtgac    4980
cacgcctgtg ctcagtttgg cagctataga aggaaatgct gtcccataaa atgccatccc    5040
tatttctaat ataacactct tttccaggaa gcatgcttaa gcatcttgtt acagagacat    5100
acatccatta tggcttggca atctcttta tttgttgact ctagctccct tcaaagtcga    5160
ggaaagatct ttactcactt aatgaggaca ttccccatca ctgtctgtac cagttcacct    5220 ttatttacg ttttattcag tctgtaaatt aactggccct ttgcagtaac ttgtacataa    5280
agtgctagaa aatcatgttc cttgtcctga gtaagagtta atcagagtaa gtgcatttct    5340
ggagttgttt ctgtgatgta aattatgatc attatttaag aagtcaaatc ctgatcttga    5400
agtgcttttt atacagctct ctaataatta caaatatccg aaagtcattt cttggaacac    5460
aagtggagta tgccaaattt tatatgaatt tttcagatta tctaagcttc caggttttat    5520
aattagaaga taatgagaga attaatgggg tttatattta cattatctct caactatgta    5580
gcccatatta ctcaccctat gagtgaatct ggaattgctt ttcatgtgaa atcattgtgg    5640
tctatgagtt tacaatactg caaactgtgt tattttatct aaaccattgc ttaatgagtg    5700
tgtttttcca tgaatgaata taccgtggtt catatgttag catggcagca ttttcagata    5760 gcttttgtt tgttgggaag ttggggtttt gggggaggg ggagtattag tacgttgcat    5820
ggaatagcct actttataat gatgggaatg ctttttcttt tgtttggga ttttttttt    5880 tgaagtgaaa tttaactttt tgtgccagta gtactattat acccatcttc agtgtcttac    5940
ttgtactgta tcaaattcca taccctcatt taattcttaa taaaactgtt cacttgtaaa    6000 aaaaaaaaa aaaaaaaa                                                   6018
```

<210> SEQ ID NO 12
<211> LENGTH: 2039
<212> TYPE: DNA
<213> ORGANISM: Homo sapiens

<400> SEQUENCE: 12

| | |
|---|---|
| ccacatccag aagcaaaagc acttcaatga gcgagaagcc agccgagtgg tgcgggacgt | 60 |
| tgctgctgcc cttgacttcc tgcataccaa aggcattgct catcgtgatc tgaaaccaga | 120 |
| aaatatattg tgtgaatctc cagaaaaggt gtctccagtg aaaatctgtg actttgactt | 180 |
| gggcagtggg atgaaactga caactcctg tacccccata accacaccag agctgaccac | 240 |
| cccatgtggc tctgcagaat acatggcccc tgaggtagtg gaggtcttca cggaccaggc | 300 |
| cacattctac gacaagcgct gtgacctgtg gagcctgggc gtggtcctct acatcatgct | 360 |
| gagtggctac ccacccttcg tgggtcactg cggggccgac tgtggctggg accggggcga | 420 |
| ggtctgcagg gtgtgccaga acaagctgtt tgaaagcatc caggaaggca gtatgagtt | 480 |
| tcctgacaag gactgggcac acatctccag tgaagccaaa gacctcatct ccaagctcct | 540 |
| ggtgcgagat gcaaagcaga aacttagcgc cgcccaagtt ctgcagcacc catgggtgca | 600 |
| ggggcaagct ccagaaaagg gactcccac gccgcaagtc ctccagagga cagcagcac | 660 |
| aatggacctg acgctcttcg cagctgaggc catcgcctt aaccgccagc tatctcagca | 720 |
| cgaagagaac gaactagcag aggagccaga ggcactagct gatggcctct gctccatgaa | 780 |
| gctttcccct ccctgcaagt cacgcctggc ccggagacgg gccctggccc aggcaggccg | 840 |
| tggtgaaaac aggagcccgc ccacagcact ctgaaatgct ccagtcacac cttataggcc | 900 |
| ctaggcctgg ccaggcattg tccctggaa acctgtgtgg ctaaagtctg ctgagcaggc | 960 |
| agcagcctct gctctgtggc tccattcagg cttttcatc tacgaaggcc ctgaggttcc | 1020 |
| catcaacccc catttcccta gggtcctgga ggaaaaagct ttttccaaag gggttgtctt | 1080 |
| tgaaaaggaa agcaatcact tctcactttg cataattgcc tgcagcagga acatctcttc | 1140 |
| actgggctcc acctgctcac ccgcctgcag atctgggatc cagcctgctc tcaccgctgt | 1200 |
| agctgtggcg gctggggctg cagcctgcag ggagaagcaa gaagcatcag ttgacagagg | 1260 |
| ctgccgacac gtgcctcttc cctctcttct ctgtcaccct cctctggcgg tccttccacc | 1320 |
| ttcctctgtc ctccggatgt cctctttgcc cgtcttctcc cttggctgag caaagccatc | 1380 |
| ccctcaattc agggaagggc aaggagcctt cctcattcag gaaatcaaat cagtcttccg | 1440 |
| gtctgcagca cggaaaagca cataatcttt ctttgctgtg actgaaatgt atccctcgtt | 1500 |
| tatcatcccc tttgtttgtg attgctgcta aagtcagtag tatcgttttt ttaaaaaaaa | 1560 |
| agtttggtgt ttttaaccat gctgttccat caaagatgat accttaaact cccactgcaa | 1620 |
| gcccatgaat ttcccagaga gtggaacggc ttgctcttct ttctagaatg tccatgcact | 1680 |
| tgggttttaa tcagcagttc cctattattc tgattttaag ctgttcctgt gatgaactta | 1740 |
| gagacagcat cggtgtctgc tgctgtgtcc ccaggtcttg tgtgggtggc acagatctgg | 1800 |
| gcagttagat agtgctctgt gcctaaggtg aagccacact agggtgaagc ctcacttccc | 1860 |
| tgtttgagca atgcagtgcc tgctgcccgt gtgcatgaag gtacagccat tcagataagt | 1920 |
| ggaactattg agttacataa agaaaataga tttgcatttg tcaggcagac gtttatacaa | 1980 |
| caccacggtg cttttatacattgtgcttat tttaataaaa ctgaaattct aaaaaaaaa | 2039 |

<210> SEQ ID NO 13
<211> LENGTH: 766
<212> TYPE: DNA
<213> ORGANISM: Homo sapiens

<400> SEQUENCE: 13

| | |
|---|---|
| ctctctttcg attcttccat actcagagta cgcacggtct gattttctct ttggattctt | 60 |

| | |
|---|---|
| ccaaaatcag agtcagactg ctcccggtgc catgaacgga gacgacgcct ttgcaaggag | 120 |
| acccacggtt ggtgctcaaa taccagagaa gatccaaaag gccttcgatg atattgccaa | 180 |
| atacttctct aaggaagagt gggaaaagat gaaagcctcg gagaaaatct tctatgtgta | 240 |
| tatgaagaga agtatgagg ctatgactaa actaggtttc aaggccaccc tcccacctt | 300 |
| catgtgtaat aaacgggccg aagacttcca ggggaatgat ttggataatg accctaaccg | 360 |
| tgggaatcag gttaacgtc ctcagatgac tttcggcagg ctccagggaa tctccccgaa | 420 |
| gatcatgccc aagaagccag cagaggaagg aaatgattcg gaggaagtgc cagaagcatc | 480 |
| tggcccacaa aatgatggga aagagctgtg ccccccggga aaaccaacta cctctgagaa | 540 |
| gattcacgag agatctggac ccaaaagggg ggaacatgcc tggacccaca gactgcgtga | 600 |
| gagaaaacag ctggtgattt atgaagagat cagcgaccct gaggaagatg acgagtaact | 660 |
| cccctcaggg atacgacaca tgcccatgat gagaagcaga acgtggtgac ctttcacgaa | 720 |
| catgggcatg gctgcggacc cctcgtcatc aggtgcatag caagtg | 766 |

<210> SEQ ID NO 14
<211> LENGTH: 4204
<212> TYPE: DNA
<213> ORGANISM: Homo sapiens

<400> SEQUENCE: 14

| | |
|---|---|
| acgcaggcag tgatgtcacc cagaccacac cccttccccc aatgccactt caggggtac | 60 |
| tcagagtcag agacttggtc tgaggggagc agaagcaatc tgcagaggat ggcggtccag | 120 |
| gctcagccag gcatcaactt caggaccctg agggatgacc gaaggccccg cccacccacc | 180 |
| cccaactccc ccgaccccac caggatctac agcctcagga cccccgtccc aatccttacc | 240 |
| ccttgcccca tcaccatctt catgcttacc tccaccccca tccgatcccc atccaggcag | 300 |
| aatccagttc caccctgcc cggaaccag ggtagtaccg ttgccaggat gtgacgccac | 360 |
| tgacttgcgc attggaggtc agaagaccgc gagattctcg ccctgagcaa cgagcgacgg | 420 |
| cctgacgtcg gcggagggaa gccggcccag gctcggtgag gaggcaaggt aagacgctga | 480 |
| gggaggactg aggcgggcct cacctcagac agagggcctc aaataatcca gtgctgcctc | 540 |
| tgctgccggg cctgggccac cccgcagggg aagacttcca ggctgggtcg ccactacctc | 600 |
| accccgccga ccccgccgc tttagccacg gggaactctg gggacagagc ttaatgtggc | 660 |
| cagggcaggg ctggttagaa gaggtcaggg cccacgctgt ggcaggaatc aaggtcagga | 720 |
| ccccgagagg gaactgaggg cagcctaacc accaccctca ccaccattcc cgtcccccaa | 780 |
| cacccaaccc cacccccatc ccccattccc atccccaccc ccaccccat cctggcagaa | 840 |
| tccgggcttt gcccctggta tcaagtcacg gaagctccgg gaatggcggc caggcacgtg | 900 |
| agtcctgagg ttcacatcta cggctaaggg agggaagggg ttcggtatcg cgagtatggc | 960 |
| cgttgggagg cagcgaaagg gcccaggcct cctggaagac agtggagtcc tgaggggacc | 1020 |
| cagcatgcca ggacaggggg cccactgtac ccctgtctca aaccgaggca ccttttcatt | 1080 |
| cggctacggg aatcctaggg atgcagaccc acttcagcag ggggttgggg cccagccctg | 1140 |
| cgaggagtca tggggaggaa gaagagggag gactgagggg accttggagt ccagatcagt | 1200 |
| ggcaaccttg gctggggga tgctgggcac agtggccaaa tgtgctctgt gctcattgcg | 1260 |
| ccttcagggt gaccagagag ttgagggctg tggtctgaag agtgggactt caggtcagca | 1320 |
| gagggaggaa tccaggatc tgcagggccc aaggtgtacc cccaaggggc ccctatgtgg | 1380 |
| tggacagatg cagtggtcct aggatctgcc aagcatccag gtgaagagac tgaggagga | 1440 |

-continued

```
ttgagggtac ccctgggaca gaatgcggac tgggggcccc ataaaaatct gccctgctcc    1500
tgctgttacc tcagagagcc tgggcagggc tgtcagctga ggtccctcca ttatcctagg    1560
atcactgatg tcaggaagg ggaagccttg gtctgagggg gctgcactca gggcagtaga    1620 ggaggctct cagaccctac taggagtgga ggtgaggacc aagcagtctc ctcacccagg    1680
gtacatggac ttcaataaat ttggacatct ctcgttgtcc tttccgggag gacctgggaa    1740
tgtatggcca gatgtgggtc ccctcatgtt tttctgtacc atatcaggta tgtgagttct    1800
tgacatgaga gattctcagg ccagcagaag ggagggatta ggccctataa ggagaaaggt    1860
gagggccctg agtgagcaca gaggggatcc tccaccccag tagagtgggg acctcacaga    1920
gtctggccaa ccctcctgac agttctggga atccgtggct gcgtttgctg tctgcacatt    1980
ggggccccgt ggattcctct cccaggaatc aggagctcca ggaacaaggc agtgaggact    2040
tggtctgagg cagtgtcctc aggtcacaga gtagaggggg ctcagatagt gccaacggtg    2100
aaggtttgcc ttggattcaa accaagggcc ccacctgccc cagaacacat ggactccaga    2160
gcgcctggcc tcaccctcaa tactttcagt cctgcagcct cagcatgcgc tggccggatg    2220
taccctgagg tgccctctca cttcctcctt caggttctga ggggacaggc tgacctggag    2280
gaccagaggc ccccgaggga gcactgaagg agaagatctg taagtaagcc tttgttagag    2340
cctccaaggt tccattcagt actcagctga ggtctctcac atgctccctc tctcccagg    2400 ccagtgggtc tccattgccc agctcctgcc cacactcccg cctgttgccc tgaccagagt    2460
catcatgcct cttgagcaga ggagtcagca ctgcaagcct gaagaaggcc ttgaggcccg    2520
aggagaggcc ctgggcctgg tgggtgcgca ggctcctgct actgaggagc aggaggctgc    2580
ctcctcctct tctactctag ttgaagtcac cctgggggag gtgcctgctg ccgagtcacc    2640
agatcctccc cagagtcctc agggagcctc cagcctcccc actaccatga actaccctct    2700
ctggagccaa tcctatgagg actccagcaa ccaagaagag gaggggccaa gcaccttccc    2760
tgacctggag tccgagttcc aagcagcact cagtaggaag gtggccgagt tggttcattt    2820
tctgctcctc aagtatcgag ccaggagcc ggtcacaaag gcagaaatgc tggggagtgt    2880
cgtcggaaat tggcagtatt tctttcctgt gatcttcagc aaagcttcca gttccttgca    2940
gctggtcttt ggcatcgagc tgatggaagt ggacccatc ggccacttgt acatctttgc    3000
cacctgcctg ggcctctcct acgatggcct gctgggtgac aatcagatca tgcccaaggc    3060
aggcctcctg ataatcgtcc tggccataat cgcaagagag ggcgactgtg ccctgagga    3120 gaaaatctgg gaggagctga gtgtgttaga ggtgtttgag gggagggaag acagtatctt    3180 ggggatccc aagaagctgc tcacccaaca tttcgtgcag gaaaactacc tggagtaccg    3240
gcaggtcccc ggcagtgatc ctgcatgtta tgaattcctg tggggtccaa gggccctcgt    3300
tgaaaccagc tatgtgaaag tcctgcacca tatggtaaag atcagtggag gacctcacat    3360
ttcctaccca ccccctgcatg agtgggtttt gagagagggg gaagagtgag tctgagcacg    3420
agttgcagcc agggccagtg ggaggggtc tgggccagtg caccttccgg ggccgcatcc    3480
cttagtttcc actgcctcct gtgacgtgag gcccattctt cactctttga agcgagcagt    3540
cagcattctt agtagtgggt ttctgttctg ttggatgact ttgagattat tctttgtttc    3600
ctgttggagt tgttcaaatg ttcctttaa cggatggttg aatgagcgtc agcatccagg    3660
tttatgaatg acagtagtca cacatagtgc tgtttatata gtttaggagt aagagtcttg    3720 tttttactc aaattgggaa atccattcca ttttgtgaat tgtgacataa taatagcagt    3780
```

```
ggtaaaagta tttgcttaaa attgtgagcg aattagcaat aacatacatg agataactca    3840
agaaatcaaa agatagttga ttcttgcctt gtacctcaat ctattctgta aaattaaaca    3900
aatatgcaaa ccaggatttc cttgacttct tgagaatgc aagcgaaatt aaatctgaat     3960
aaataattct tcctcttcac tggctcgttt cttttccgtt cactcagcat ctgctctgtg    4020
ggaggccctg ggttagtagt ggggatgcta aggtaagcca gactcacgcc tacccatagg    4080
gctgtagagc ctaggacctg cagtcatata attaaggtgg tgagaagtcc tgtaagatgt    4140
agaggaaatg taagagaggg gtgagggtgt ggcgctccgg gtgagagtag tggagtgtca    4200
gtgc                                                                 4204
```

<210> SEQ ID NO 15
<211> LENGTH: 752
<212> TYPE: DNA
<213> ORGANISM: Homo sapiens

<400> SEQUENCE: 15

```
atcctcgtgg gccctgacct tctctctgag agccgggcag aggctccgga gccatgcagg     60
ccgaaggccg gggcacaggg ggttcgacgg gcgatgctga tggcccagga ggccctggca   120
ttcctgatgg cccaggggc aatgctggcg gcccaggaga ggcgggtgcc acgggcggca    180
gaggtccccg ggcgcaggg gcagcaaggg cctcggggcc gggaggaggc gccccgcggg   240
gtccgcatgg cggcgcggct tcagggctga atggatgctg cagatgcggg gccaggggc    300 cggagagccg cctgcttgag ttctacctcg ccatgccttt cgcgacaccc atggaagcag   360
agctggcccg caggagcctg gcccaggatg ccccaccgct tcccgtgcca ggggtgcttc   420
tgaaggagtt cactgtgtcc ggcaacatac tgactatccg actgactgct gcagaccacc   480
gccaactgca gctctccatc agctcctgtc tccagcagct ttccctgttg atgtggatca   540
cgcagtgctt tctgcccgtg tttttggctc agcctccctc agggcagagg cgctaagccc   600
agcctggcgc cccttcctag gtcatgcctc ctcccctagg gaatggtccc agcacgagtg   660
gccagttcat tgtgggggcc tgattgtttg tcgctggagg aggacggctt acatgtttgt   720
ttctgtagaa aataaaactg agctacgaaa aa                                  752
```

<210> SEQ ID NO 16
<211> LENGTH: 1967
<212> TYPE: PRT
<213> ORGANISM: Homo sapiens

<400> SEQUENCE: 16

```
Leu Glu Phe Lys Ile Ser Asp Glu Glu Ala Asp Asp Ala Asp Ala Ala
1               5                   10                  15

Gly Arg Asp Ser Pro Ser Asn Thr Ser Gln Ser Glu Gln Gln Glu Ser
                20                  25                  30

Val Asp Ala Glu Gly Pro Val Val Glu Lys Ile Met Ser Ser Arg Ser
            35                  40                  45

Val Lys Lys Gln Lys Glu Ser Gly Glu Glu Val Glu Ile Glu Glu Phe
        50                  55                  60

Tyr Val Lys Tyr Lys Asn Phe Ser Tyr Leu His Cys Gln Trp Ala Ser
65                  70                  75                  80

Ile Glu Asp Leu Glu Lys Asp Lys Arg Ile Gln Gln Lys Ile Lys Arg
                85                  90                  95

Phe Lys Ala Lys Gln Gly Gln Asn Lys Phe Leu Ser Glu Ile Glu Asp
                100                 105                 110
```

-continued

```
Glu Leu Phe Asn Pro Asp Tyr Val Glu Val Asp Arg Ile Met Asp Phe
            115                 120                 125
Ala Arg Ser Thr Asp Asp Arg Gly Glu Pro Val Thr His Tyr Leu Val
        130                 135                 140
Lys Trp Cys Ser Leu Pro Tyr Glu Asp Ser Thr Trp Glu Arg Arg Gln
145                 150                 155                 160
Asp Ile Asp Gln Ala Lys Ile Glu Glu Phe Glu Lys Leu Met Ser Arg
                165                 170                 175
Glu Pro Glu Thr Glu Arg Val Glu Arg Pro Ala Asp Asp Trp Lys
            180                 185                 190
Lys Ser Glu Ser Ser Arg Glu Tyr Lys Asn Asn Lys Leu Arg Glu
        195                 200                 205
Tyr Gln Leu Glu Gly Val Asn Trp Leu Leu Phe Asn Trp Tyr Asn Met
        210                 215                 220
Arg Asn Cys Ile Leu Ala Asp Glu Met Gly Leu Gly Lys Thr Ile Gln
225                 230                 235                 240
Ser Ile Thr Phe Leu Tyr Glu Ile Tyr Leu Lys Gly Ile His Gly Pro
                245                 250                 255
Phe Leu Val Ile Ala Pro Leu Ser Thr Ile Pro Asn Trp Glu Arg Glu
                260                 265                 270
Phe Arg Thr Trp Thr Glu Leu Asn Val Val Tyr His Gly Ser Gln
            275                 280                 285
Ala Ser Arg Arg Thr Ile Gln Leu Tyr Glu Met Tyr Phe Lys Asp Pro
        290                 295                 300
Gln Gly Arg Val Ile Lys Gly Ser Tyr Lys Phe His Ala Ile Ile Thr
305                 310                 315                 320
Thr Phe Glu Met Ile Leu Thr Asp Cys Pro Glu Leu Arg Asn Ile Pro
                325                 330                 335
Trp Arg Cys Val Val Ile Asp Glu Ala His Arg Leu Lys Asn Arg Asn
                340                 345                 350
Cys Lys Leu Leu Glu Gly Leu Lys Met Met Asp Leu Glu His Lys Val
            355                 360                 365
Leu Leu Thr Gly Thr Pro Leu Gln Asn Thr Val Glu Glu Leu Phe Ser
        370                 375                 380
Leu Leu His Phe Leu Glu Pro Ser Arg Phe Pro Ser Glu Thr Thr Phe
385                 390                 395                 400
Met Gln Glu Phe Gly Asp Leu Lys Thr Glu Glu Gln Val Gln Lys Leu
                405                 410                 415
Gln Ala Ile Leu Lys Pro Met Met Leu Arg Arg Leu Lys Glu Asp Val
            420                 425                 430
Glu Lys Asn Leu Ala Pro Lys Glu Glu Thr Ile Ile Glu Val Glu Leu
        435                 440                 445
Thr Asn Ile Gln Lys Lys Tyr Tyr Arg Ala Ile Leu Glu Lys Asn Phe
        450                 455                 460
Thr Phe Leu Ser Lys Gly Gly Gly Gln Ala Asn Val Pro Asn Leu Leu
465                 470                 475                 480
Asn Thr Met Met Glu Leu Arg Lys Cys Cys Asn His Pro Tyr Leu Ile
                485                 490                 495
Asn Gly Ala Glu Glu Lys Ile Leu Glu Glu Phe Lys Glu Thr His Asn
            500                 505                 510
Ala Glu Ser Pro Asp Phe Gln Leu Gln Ala Met Ile Gln Ala Ala Gly
        515                 520                 525
Lys Leu Val Leu Ile Asp Lys Leu Leu Pro Lys Leu Lys Ala Gly Gly
```

```
                530                 535                 540
His Arg Val Leu Ile Phe Ser Gln Met Val Arg Cys Leu Asp Ile Leu
545                 550                 555                 560

Glu Asp Tyr Leu Ile Gln Arg Arg Tyr Pro Tyr Glu Arg Ile Asp Gly
                565                 570                 575

Arg Val Arg Gly Asn Leu Arg Gln Ala Ala Ile Asp Arg Phe Ser Lys
                580                 585                 590

Pro Asp Ser Asp Arg Phe Val Phe Leu Leu Cys Thr Arg Ala Gly Gly
                595                 600                 605

Leu Gly Ile Asn Leu Thr Ala Ala Asp Thr Cys Ile Ile Phe Asp Ser
                610                 615                 620

Asp Trp Asn Pro Gln Asn Asp Leu Gln Ala Gln Ala Arg Cys His Arg
625                 630                 635                 640

Ile Gly Gln Ser Lys Ser Val Lys Ile Tyr Arg Leu Ile Thr Arg Asn
                645                 650                 655

Ser Tyr Glu Arg Glu Met Phe Asp Lys Ala Ser Leu Lys Leu Gly Leu
                660                 665                 670

Asp Lys Ala Val Leu Gln Ser Met Ser Gly Arg Glu Asn Ala Thr Asn
                675                 680                 685

Gly Val Gln Gln Leu Ser Lys Lys Glu Ile Glu Asp Leu Leu Arg Lys
                690                 695                 700

Gly Ala Tyr Gly Ala Leu Met Asp Glu Glu Asp Gly Ser Lys Phe
705                 710                 715                 720

Cys Glu Glu Asp Ile Asp Gln Ile Leu Leu Arg Arg Thr His Thr Ile
                725                 730                 735

Thr Ile Glu Ser Glu Gly Lys Gly Ser Thr Phe Ala Lys Ala Ser Phe
                740                 745                 750

Val Ala Ser Gly Asn Arg Thr Asp Ile Ser Leu Asp Asp Pro Asn Phe
                755                 760                 765

Trp Gln Lys Trp Ala Lys Lys Ala Glu Leu Asp Ile Asp Ala Leu Asn
                770                 775                 780

Gly Arg Asn Asn Leu Val Ile Asp Thr Pro Arg Val Arg Lys Gln Thr
785                 790                 795                 800

Arg Leu Tyr Ser Ala Val Lys Glu Asp Glu Leu Met Glu Phe Ser Asp
                805                 810                 815

Leu Glu Ser Asp Ser Glu Glu Lys Pro Cys Ala Lys Pro Arg Arg Pro
                820                 825                 830

Gln Asp Lys Ser Gln Gly Tyr Ala Arg Ser Glu Cys Phe Arg Val Glu
                835                 840                 845

Lys Asn Leu Leu Val Tyr Gly Trp Gly Arg Trp Thr Asp Ile Leu Ser
850                 855                 860

His Gly Arg Tyr Lys Arg Gln Leu Thr Glu Gln Asp Val Glu Thr Ile
865                 870                 875                 880

Cys Arg Thr Ile Leu Val Tyr Cys Leu Asn His Tyr Lys Gly Asp Glu
                885                 890                 895

Asn Ile Lys Ser Phe Ile Trp Asp Leu Ile Thr Pro Thr Ala Asp Gly
                900                 905                 910

Gln Thr Arg Ala Leu Val Asn His Ser Gly Leu Ser Ala Pro Val Pro
                915                 920                 925

Arg Gly Arg Lys Gly Lys Lys Val Lys Ala Gln Ser Thr Gln Pro Val
                930                 935                 940

Val Gln Asp Ala Asp Trp Leu Ala Ser Cys Asn Pro Asp Ala Leu Phe
945                 950                 955                 960
```

-continued

```
Gln Glu Asp Ser Tyr Lys Lys His Leu Lys His His Cys Asn Lys Val
            965                 970                 975

Leu Leu Arg Val Arg Met Leu Tyr Tyr Leu Arg Gln Glu Val Ile Gly
            980                 985                 990

Asp Gln Ala Asp Lys Ile Leu Glu Gly Ala Asp Ser Ser Glu Ala Asp
            995                1000                1005

Val Trp Ile Pro Glu Pro Phe His Ala Glu Val Pro Ala Asp Trp
        1010                1015                1020

Trp Asp Lys Glu Ala Asp Lys Ser Leu Leu Ile Gly Val Phe Lys
        1025                1030                1035

His Gly Tyr Glu Lys Tyr Asn Ser Met Arg Ala Asp Pro Ala Leu
        1040                1045                1050

Cys Phe Leu Glu Arg Val Gly Met Pro Asp Ala Lys Ala Ile Ala
        1055                1060                1065

Ala Glu Gln Arg Gly Thr Asp Met Leu Ala Asp Gly Gly Asp Gly
        1070                1075                1080

Gly Glu Phe Asp Arg Glu Asp Glu Asp Pro Glu Tyr Lys Pro Thr
        1085                1090                1095

Arg Thr Pro Phe Lys Asp Glu Ile Asp Glu Phe Ala Asn Ser Pro
        1100                1105                1110

Ser Glu Asp Lys Glu Glu Ser Met Glu Ile His Ala Thr Gly Lys
        1115                1120                1125

His Ser Glu Ser Asn Ala Glu Leu Gly Gln Leu Tyr Trp Pro Asn
        1130                1135                1140

Thr Ser Thr Leu Thr Thr Arg Leu Arg Arg Leu Ile Thr Ala Tyr
        1145                1150                1155

Gln Arg Ser Tyr Lys Arg Gln Gln Met Arg Gln Glu Ala Leu Met
        1160                1165                1170

Lys Thr Asp Arg Arg Arg Arg Pro Arg Glu Glu Val Arg Ala
        1175                1180                1185

Leu Glu Ala Glu Arg Glu Ala Ile Ile Ser Glu Lys Arg Gln Lys
        1190                1195                1200

Trp Thr Arg Arg Glu Glu Ala Asp Phe Tyr Arg Val Val Ser Thr
        1205                1210                1215

Phe Gly Val Ile Phe Asp Pro Val Lys Gln Gln Phe Asp Trp Asn
        1220                1225                1230

Gln Phe Arg Ala Phe Ala Arg Leu Asp Lys Lys Ser Asp Glu Ser
        1235                1240                1245

Leu Glu Lys Tyr Phe Ser Cys Phe Val Ala Met Cys Arg Arg Val
        1250                1255                1260

Cys Arg Met Pro Val Lys Pro Asp Asp Glu Pro Pro Asp Leu Ser
        1265                1270                1275

Ser Ile Ile Glu Pro Ile Thr Glu Glu Arg Ala Ser Arg Thr Leu
        1280                1285                1290

Tyr Arg Ile Glu Leu Leu Arg Lys Ile Arg Glu Gln Val Leu His
        1295                1300                1305

His Pro Gln Leu Gly Glu Arg Leu Lys Leu Cys Gln Pro Ser Leu
        1310                1315                1320

Asp Leu Pro Glu Trp Trp Glu Cys Gly Arg His Asp Arg Asp Leu
        1325                1330                1335

Leu Val Gly Ala Ala Lys His Gly Val Ser Arg Thr Asp Tyr His
        1340                1345                1350
```

-continued

```
Ile Leu Asn Asp Pro Glu Leu Ser Phe Leu Asp Ala His Lys Asn
1355                1360                1365

Phe Ala Gln Asn Arg Gly Ala Gly Asn Thr Ser Ser Leu Asn Pro
1370                1375                1380

Leu Ala Val Gly Phe Val Gln Thr Pro Pro Val Ile Ser Ser Ala
1385                1390                1395

His Ile Gln Asp Glu Arg Val Leu Glu Gln Ala Glu Gly Lys Val
1400                1405                1410

Glu Glu Pro Glu Asn Pro Ala Ala Lys Glu Lys Cys Glu Gly Lys
1415                1420                1425

Glu Glu Glu Glu Glu Thr Asp Gly Ser Gly Lys Glu Ser Lys Gln
1430                1435                1440

Glu Cys Glu Ala Glu Ala Ser Ser Val Lys Asn Glu Leu Lys Gly
1445                1450                1455

Val Glu Val Gly Ala Asp Thr Gly Ser Lys Ser Ile Ser Glu Lys
1460                1465                1470

Gly Ser Glu Glu Asp Glu Glu Glu Lys Leu Glu Asp Asp Asp Lys
1475                1480                1485

Ser Glu Glu Ser Ser Gln Pro Glu Ala Gly Ala Val Ser Arg Gly
1490                1495                1500

Lys Asn Phe Asp Glu Glu Ser Asn Ala Ser Met Ser Thr Ala Arg
1505                1510                1515

Asp Glu Thr Arg Asp Gly Phe Tyr Met Glu Asp Gly Asp Pro Ser
1520                1525                1530

Val Ala Gln Leu Leu His Glu Arg Thr Phe Ala Phe Ser Phe Trp
1535                1540                1545

Pro Lys Asp Arg Val Met Ile Asn Arg Leu Asp Asn Ile Cys Glu
1550                1555                1560

Ala Val Leu Lys Gly Lys Trp Pro Val Asn Arg Arg Gln Met Phe
1565                1570                1575

Asp Phe Gln Gly Leu Ile Pro Gly Tyr Thr Pro Thr Thr Val Asp
1580                1585                1590

Ser Pro Leu Gln Lys Arg Ser Phe Ala Glu Leu Ser Met Val Gly
1595                1600                1605

Gln Ala Ser Ile Ser Gly Ser Glu Asp Ile Thr Thr Ser Pro Gln
1610                1615                1620

Leu Ser Lys Glu Asp Ala Leu Asn Leu Ser Val Pro Arg Gln Arg
1625                1630                1635

Arg Arg Arg Arg Arg Lys Ile Glu Ile Glu Ala Glu Arg Ala Ala
1640                1645                1650

Lys Arg Arg Asn Leu Met Glu Met Val Ala Gln Leu Arg Glu Ser
1655                1660                1665

Gln Val Val Ser Glu Asn Gly Gln Glu Lys Val Val Asp Leu Ser
1670                1675                1680

Lys Ala Ser Arg Glu Ala Thr Ser Ser Thr Ser Asn Phe Ser Ser
1685                1690                1695

Leu Ser Ser Lys Phe Ile Leu Pro Asn Val Ser Thr Pro Val Ser
1700                1705                1710

Asp Ala Phe Lys Thr Gln Met Glu Leu Leu Gln Ala Gly Leu Ser
1715                1720                1725

Arg Thr Pro Thr Arg His Leu Leu Asn Gly Ser Leu Val Asp Gly
1730                1735                1740

Glu Pro Pro Met Lys Arg Arg Arg Gly Arg Arg Lys Asn Val Glu
```

-continued

```
                1745                1750                1755

Gly Leu Asp Leu Leu Phe Met Ser His Lys Arg Thr Ser Leu Ser
        1760                1765                1770

Ala Glu Asp Ala Glu Val Thr Lys Ala Phe Glu Glu Asp Ile Glu
    1775                1780                1785

Thr Pro Pro Thr Arg Asn Ile Pro Ser Pro Gly Gln Leu Asp Pro
1790                1795                1800

Asp Thr Arg Ile Pro Val Ile Asn Leu Glu Asp Gly Thr Arg Leu
    1805                1810                1815

Val Gly Glu Asp Ala Pro Lys Asn Lys Asp Leu Val Glu Trp Leu
    1820                1825                1830

Lys Leu His Pro Thr Tyr Thr Val Asp Met Pro Ser Tyr Val Pro
    1835                1840                1845

Lys Asn Ala Asp Val Leu Phe Ser Ser Phe Gln Lys Pro Lys Gln
    1850                1855                1860

Lys Arg His Arg Cys Arg Asn Pro Asn Lys Leu Asp Ile Asn Thr
    1865                1870                1875

Leu Thr Gly Glu Glu Arg Val Pro Val Val Asn Lys Arg Asn Gly
    1880                1885                1890

Lys Lys Met Gly Gly Ala Met Ala Pro Pro Met Lys Asp Leu Pro
    1895                1900                1905

Arg Trp Leu Glu Glu Asn Pro Glu Phe Ala Val Ala Pro Asp Trp
    1910                1915                1920

Thr Asp Ile Val Lys Gln Ser Gly Phe Val Pro Glu Ser Met Phe
    1925                1930                1935

Asp Arg Leu Leu Thr Gly Pro Val Val Arg Gly Glu Gly Ala Ser
    1940                1945                1950

Arg Arg Gly Arg Arg Pro Lys Ser Glu Ile Ala Arg Ala Ala
    1955                1960                1965

<210> SEQ ID NO 17
<211> LENGTH: 109
<212> TYPE: PRT
<213> ORGANISM: Homo sapiens
<220> FEATURE:
<221> NAME/KEY: MISC_FEATURE
<222> LOCATION: (84)..(84)
<223> OTHER INFORMATION: Xaa = any amino acid
<220> FEATURE:
<221> NAME/KEY: MISC_FEATURE
<222> LOCATION: (100)..(100)
<223> OTHER INFORMATION: Xaa = any amino acid

<400> SEQUENCE: 17

Arg Pro Ser Leu Pro Arg Ala Leu Pro Ala Ala Pro His Glu Arg Ser
1               5                   10                  15

Pro Ala Arg Pro Gly Ser Val Gly Gly Ala Pro Pro Met Leu Leu
            20                  25                  30

Gln Pro Ala Pro Cys Ala Pro Ser Ala Gly Phe Pro Arg Pro Leu Ala
        35                  40                  45

Ala Pro Gly Ala Met His Leu Phe Ala Glu Gly His His Val His Gln
    50                  55                  60

Asp Leu Arg Gly Arg Pro Ala Val Pro His Tyr Arg Arg Leu Ala Gln
65                  70                  75                  80

Glu Val Leu Xaa Gly Leu Arg Arg His Leu Arg Arg Pro Trp Ser Ser
                85                  90                  95

Pro Thr Ala Xaa Arg Ala Ser Pro Ala Ala Thr Ala Ser
```

```
                          100                 105

<210> SEQ ID NO 18
<211> LENGTH: 897
<212> TYPE: PRT
<213> ORGANISM: Homo sapiens

<400> SEQUENCE: 18

Glu Phe Leu Leu Ser Lys Ser Lys Glu Pro Thr Pro Gly Gly Leu Asn
1               5                   10                  15

His Ser Leu Pro Gln His Pro Lys Cys Trp Gly Ala His His Ala Ser
            20                  25                  30

Leu Asp Gln Ser Ser Pro Pro Gln Ser Gly Pro Pro Gly Thr Pro Pro
        35                  40                  45

Ser Tyr Lys Leu Pro Leu Pro Gly Pro Tyr Asp Ser Arg Asp Asp Phe
    50                  55                  60

Pro Leu Arg Lys Thr Ala Ser Glu Pro Asn Leu Lys Val Arg Ser Arg
65                  70                  75                  80

Leu Lys Gln Lys Val Ala Glu Arg Arg Ser Ser Pro Leu Leu Arg Arg
                85                  90                  95

Lys Asp Gly Thr Val Ile Ser Thr Phe Lys Lys Arg Ala Val Glu Ile
            100                 105                 110

Thr Gly Ala Gly Pro Gly Ala Ser Ser Val Cys Asn Ser Ala Pro Gly
        115                 120                 125

Ser Gly Pro Ser Ser Pro Asn Ser Ser His Ser Thr Ile Ala Glu Asn
    130                 135                 140

Gly Phe Thr Gly Ser Val Pro Asn Ile Pro Thr Glu Met Leu Pro Gln
145                 150                 155                 160

His Arg Ala Leu Pro Leu Asp Ser Ser Pro Asn Gln Phe Ser Leu Tyr
                165                 170                 175

Thr Ser Pro Ser Leu Pro Asn Ile Ser Leu Gly Leu Gln Ala Thr Val
            180                 185                 190

Thr Val Thr Asn Ser His Leu Thr Ala Ser Pro Lys Leu Ser Thr Gln
        195                 200                 205

Gln Glu Ala Glu Arg Gln Ala Leu Gln Ser Leu Arg Gln Gly Gly Thr
    210                 215                 220

Leu Thr Gly Lys Phe Met Ser Thr Ser Ser Ile Pro Gly Cys Leu Leu
225                 230                 235                 240

Gly Val Ala Leu Glu Gly Asp Gly Ser Pro His Gly His Ala Ser Leu
                245                 250                 255

Leu Gln His Val Leu Leu Leu Glu Gln Ala Arg Gln Gln Ser Thr Leu
            260                 265                 270

Ile Ala Val Pro Leu His Gly Gln Ser Pro Leu Val Thr Gly Glu Arg
        275                 280                 285

Val Ala Thr Ser Met Arg Thr Val Gly Lys Leu Pro Arg His Arg Pro
    290                 295                 300

Leu Ser Arg Thr Gln Ser Ser Pro Leu Pro Gln Ser Pro Gln Ala Leu
305                 310                 315                 320

Gln Gln Leu Val Met Gln Gln Gln His Gln Gln Phe Leu Glu Lys Gln
                325                 330                 335

Lys Gln Gln Gln Leu Gln Leu Gly Lys Ile Leu Thr Lys Thr Gly Glu
            340                 345                 350

Leu Pro Arg Gln Pro Thr Thr His Pro Glu Glu Thr Glu Glu Glu Leu
        355                 360                 365
```

```
Thr Glu Gln Gln Glu Val Leu Leu Gly Glu Gly Ala Leu Thr Met Pro
    370                 375                 380

Arg Glu Gly Ser Thr Glu Ser Glu Ser Thr Gln Glu Asp Leu Glu Glu
385                 390                 395                 400

Glu Asp Glu Glu Asp Gly Glu Glu Glu Asp Cys Ile Gln Val
                405                 410                 415

Lys Asp Glu Glu Gly Glu Ser Gly Ala Glu Glu Gly Pro Asp Leu Glu
                420                 425                 430

Glu Pro Gly Ala Gly Tyr Lys Lys Leu Phe Ser Asp Ala Gln Pro Leu
            435                 440                 445

Gln Pro Leu Gln Val Tyr Gln Ala Pro Leu Ser Leu Ala Thr Val Pro
    450                 455                 460

His Gln Ala Leu Gly Arg Thr Gln Ser Ser Pro Ala Ala Pro Gly Gly
465                 470                 475                 480

Met Lys Asn Pro Pro Asp Gln Pro Val Lys His Leu Phe Thr Ser
                485                 490                 495

Val Val Tyr Asp Thr Phe Met Leu Lys His Gln Cys Met Cys Gly Asn
                500                 505                 510

Thr His Val His Pro Glu His Ala Gly Arg Ile Gln Ser Ile Trp Ser
    515                 520                 525

Arg Leu Gln Glu Thr Gly Leu Leu Ser Lys Cys Glu Arg Ile Arg Gly
530                 535                 540

Arg Lys Ala Thr Leu Asp Glu Ile Gln Thr Val His Ser Glu Tyr His
545                 550                 555                 560

Thr Leu Leu Tyr Gly Thr Ser Pro Leu Asn Arg Gln Lys Leu Asp Ser
                565                 570                 575

Lys Lys Leu Leu Gly Pro Ile Ser Gln Lys Met Tyr Ala Val Leu Pro
            580                 585                 590

Cys Gly Gly Ile Gly Val Asp Ser Asp Thr Val Trp Asn Glu Met His
    595                 600                 605

Ser Ser Ser Ala Val Arg Met Ala Val Gly Cys Leu Leu Glu Leu Ala
610                 615                 620

Phe Lys Val Ala Ala Gly Glu Leu Lys Asn Gly Phe Ala Ile Ile Arg
625                 630                 635                 640

Pro Pro Gly His His Ala Glu Glu Ser Thr Ala Met Gly Phe Cys Phe
                645                 650                 655

Phe Asn Ser Val Ala Ile Thr Ala Lys Leu Leu Gln Gln Lys Leu Asn
                660                 665                 670

Val Gly Lys Val Leu Ile Val Asp Trp Asp Ile His His Gly Asn Gly
            675                 680                 685

Thr Gln Gln Ala Phe Tyr Asn Asp Pro Ser Val Leu Tyr Ile Ser Leu
    690                 695                 700

His Arg Tyr Asp Asn Gly Asn Phe Phe Pro Gly Ser Gly Ala Pro Glu
705                 710                 715                 720

Glu Val Gly Gly Gly Pro Gly Val Gly Tyr Asn Val Asn Val Ala Trp
                725                 730                 735

Thr Gly Gly Val Asp Pro Pro Ile Gly Asp Val Glu Tyr Leu Thr Ala
                740                 745                 750

Phe Arg Thr Val Val Met Pro Ile Ala His Glu Phe Ser Pro Asp Val
            755                 760                 765

Val Leu Val Ser Ala Gly Phe Asp Ala Val Glu Gly His Leu Ser Pro
    770                 775                 780

Leu Gly Gly Tyr Ser Val Thr Ala Arg Cys Phe Gly His Leu Thr Arg
```

```
                     785                 790                 795                 800
Gln Leu Met Thr Leu Ala Gly Gly Arg Val Val Leu Ala Leu Glu Gly
                    805                 810                 815
Gly His Asp Leu Thr Ala Ile Cys Asp Ala Ser Glu Ala Cys Val Ser
                820                 825                 830
Ala Leu Leu Ser Val Lys Leu Gln Pro Leu Asp Glu Ala Val Leu Gln
            835                 840                 845
Gln Lys Pro Asn Ile Asn Ala Val Ala Thr Leu Glu Lys Val Ile Glu
        850                 855                 860
Ile Gln Ser Lys His Trp Ser Cys Val Gln Lys Phe Ala Ala Gly Leu
865                 870                 875                 880
Gly Arg Ser Leu Arg Gly Ala Gln Ala Gly Glu Thr Glu Glu Ala Glu
                885                 890                 895
Met

<210> SEQ ID NO 19
<211> LENGTH: 890
<212> TYPE: PRT
<213> ORGANISM: Homo sapiens

<400> SEQUENCE: 19

Met Phe Asp Tyr Met Asp Cys Glu Leu Lys Leu Ser Glu Ser Val Phe
1               5                   10                  15
Arg Gln Leu Asn Thr Ala Ile Ala Val Ser Gln Met Ser Ser Gly Gln
                20                  25                  30
Cys Arg Leu Ala Pro Leu Ile Gln Val Ile Gln Asp Cys Ser His Leu
            35                  40                  45
Tyr His Tyr Thr Val Lys Leu Leu Phe Lys Leu His Ser Cys Leu Pro
        50                  55                  60
Ala Asp Thr Leu Gln Gly His Arg Asp Arg Phe His Glu Gln Phe His
65                  70                  75                  80
Ser Leu Arg Asn Phe Phe Arg Arg Ala Ser Asp Met Leu Tyr Phe Lys
                85                  90                  95
Arg Leu Ile Gln Ile Pro Arg Leu Pro Glu Gly Pro Pro Asn Phe Leu
            100                 105                 110
Arg Ala Ser Ala Leu Ala Glu His Ile Lys Pro Val Val Val Ile Pro
        115                 120                 125
Glu Glu Ala Pro Glu Asp Glu Glu Pro Glu Asn Leu Ile Glu Ile Ser
    130                 135                 140
Thr Gly Pro Pro Ala Gly Glu Pro Val Val Val Ala Asp Leu Phe Asp
145                 150                 155                 160
Gln Thr Phe Gly Pro Pro Asn Gly Ser Val Lys Asp Asp Arg Asp Leu
                165                 170                 175
Gln Ile Glu Ser Leu Lys Arg Glu Val Glu Met Leu Arg Ser Glu Leu
            180                 185                 190
Glu Lys Ile Lys Leu Glu Ala Gln Arg Tyr Ile Ala Gln Leu Lys Ser
        195                 200                 205
Gln Val Asn Ala Leu Glu Gly Glu Leu Glu Glu Arg Lys Gln Lys
    210                 215                 220
Gln Lys Ala Leu Val Asp Asn Glu Gln Leu Arg His Glu Leu Ala Gln
225                 230                 235                 240
Leu Arg Ala Ala Gln Leu Glu Gly Glu Arg Ser Gln Gly Leu Arg Glu
                245                 250                 255
Glu Ala Glu Arg Lys Ala Ser Ala Thr Glu Ala Arg Tyr Asn Lys Leu
```

-continued

```
                260                 265                 270
Lys Glu Lys His Ser Glu Leu Val His Val His Ala Glu Leu Leu Arg
            275                 280                 285
Lys Asn Ala Asp Thr Ala Lys Gln Leu Thr Val Thr Gln Gln Ser Gln
290                 295                 300
Glu Glu Val Ala Arg Val Lys Glu Gln Leu Ala Phe Gln Val Glu Gln
305                 310                 315                 320
Val Lys Arg Glu Ser Glu Leu Lys Leu Glu Glu Lys Ser Asp Gln Leu
                325                 330                 335
Glu Lys Leu Lys Arg Glu Leu Glu Ala Lys Ala Gly Glu Leu Ala Arg
            340                 345                 350
Ala Gln Glu Ala Leu Ser His Thr Glu Gln Ser Lys Ser Glu Leu Ser
            355                 360                 365
Ser Arg Leu Asp Thr Leu Ser Ala Glu Lys Asp Ala Leu Ser Gly Ala
        370                 375                 380
Val Arg Gln Arg Glu Ala Asp Leu Leu Ala Ala Gln Ser Leu Val Arg
385                 390                 395                 400
Glu Thr Glu Ala Ala Leu Ser Arg Glu Gln Gln Arg Ser Ser Gln Glu
                405                 410                 415
Gln Gly Glu Leu Gln Gly Arg Leu Ala Glu Arg Glu Ser Gln Glu Gln
            420                 425                 430
Gly Leu Arg Gln Arg Leu Leu Asp Glu Gln Phe Ala Val Leu Arg Gly
        435                 440                 445
Ala Ala Ala Glu Ala Ala Gly Ile Leu Gln Asp Ala Val Ser Lys Leu
    450                 455                 460
Asp Asp Pro Leu His Leu Arg Cys Thr Ser Ser Pro Asp Tyr Leu Val
465                 470                 475                 480
Ser Arg Ala Gln Glu Ala Leu Asp Ala Val Ser Thr Leu Glu Glu Gly
                485                 490                 495
His Ala Gln Tyr Leu Thr Ser Leu Ala Asp Ala Ser Ala Leu Val Ala
            500                 505                 510
Ala Leu Thr Arg Phe Ser His Leu Ala Ala Asp Thr Ile Ile Asn Gly
        515                 520                 525
Gly Ala Thr Ser His Leu Ala Pro Thr Asp Pro Ala Asp Arg Leu Ile
    530                 535                 540
Asp Thr Cys Arg Glu Cys Gly Ala Arg Ala Leu Glu Leu Met Gly Gln
545                 550                 555                 560
Leu Gln Asp Gln Gln Ala Leu Arg His Met Gln Ala Ser Leu Val Arg
                565                 570                 575
Thr Pro Leu Gln Gly Ile Leu Gln Leu Gly Gln Glu Leu Lys Pro Lys
            580                 585                 590
Ser Leu Asp Val Arg Gln Glu Glu Leu Gly Ala Val Val Asp Lys Glu
        595                 600                 605
Met Ala Ala Thr Ser Ala Ala Ile Glu Asp Ala Val Arg Arg Ile Glu
    610                 615                 620
Asp Met Met Asn Gln Ala Arg His Ala Ser Ser Gly Val Lys Leu Glu
625                 630                 635                 640
Val Asn Glu Arg Ile Leu Asn Ser Cys Thr Asp Leu Met Lys Ala Ile
                645                 650                 655
Arg Leu Leu Val Thr Thr Ser Thr Ser Leu Gln Lys Glu Ile Val Glu
            660                 665                 670
Ser Gly Arg Gly Ala Ala Thr Gln Gln Glu Phe Tyr Ala Lys Asn Ser
        675                 680                 685
```

-continued

```
Arg Trp Thr Glu Gly Leu Ile Ser Ala Ser Lys Ala Val Gly Trp Gly
    690                 695                 700

Ala Thr Gln Leu Val Glu Ala Ala Asp Lys Val Val Leu His Thr Gly
705                 710                 715                 720

Lys Tyr Glu Glu Leu Ile Val Cys Ser His Glu Ile Ala Ala Ser Thr
                725                 730                 735

Ala Gln Leu Val Ala Ala Ser Lys Val Lys Ala Asn Lys His Ser Pro
                740                 745                 750

His Leu Ser Arg Leu Gln Glu Cys Ser Arg Thr Val Asn Glu Arg Ala
                755                 760                 765

Ala Asn Val Val Ala Ser Thr Lys Ser Gly Gln Glu Gln Ile Glu Asp
770                 775                 780

Arg Asp Thr Met Asp Phe Ser Gly Leu Ser Leu Ile Lys Leu Lys Lys
785                 790                 795                 800

Gln Glu Met Glu Thr Gln Val Arg Val Leu Glu Leu Glu Lys Thr Leu
                805                 810                 815

Glu Ala Glu Arg Met Arg Leu Gly Glu Leu Arg Lys Gln His Tyr Val
                820                 825                 830

Leu Ala Gly Ala Ser Gly Ser Pro Gly Glu Val Ala Ile Arg Pro
                835                 840                 845

Ser Thr Ala Pro Arg Ser Val Thr Thr Lys Pro Pro Leu Ala Gln
    850                 855                 860

Lys Pro Ser Val Ala Pro Arg Gln Asp His Gln Leu Asp Lys Lys Asp
865                 870                 875                 880

Gly Ile Tyr Pro Ala Gln Leu Val Asn Tyr
                885                 890

<210> SEQ ID NO 20
<211> LENGTH: 725
<212> TYPE: PRT
<213> ORGANISM: Homo sapiens

<400> SEQUENCE: 20

Met Ala Met Asp Ser Ser Leu Gln Ala Arg Leu Phe Pro Gly Leu Ala
1               5                   10                  15

Ile Lys Ile Gln Arg Ser Asn Gly Leu Ile His Ser Ala Asn Val Arg
                20                  25                  30

Thr Val Asn Leu Glu Lys Ser Cys Val Ser Val Glu Trp Ala Glu Gly
            35                  40                  45

Gly Ala Thr Lys Gly Lys Glu Ile Asp Phe Asp Asp Val Ala Ala Ile
        50                  55                  60

Asn Pro Glu Leu Leu Gln Leu Leu Pro Leu His Pro Lys Asp Asn Leu
65                  70                  75                  80

Pro Leu Gln Glu Asn Val Thr Ile Gln Lys Gln Lys Arg Arg Ser Val
                85                  90                  95

Asn Ser Lys Ile Pro Ala Pro Lys Glu Ser Leu Arg Ser Arg Ser Thr
            100                 105                 110

Arg Met Ser Thr Val Ser Glu Leu Arg Ile Thr Ala Gln Glu Asn Asp
        115                 120                 125

Met Glu Val Glu Leu Pro Ala Ala Ala Asn Ser Arg Lys Gln Phe Ser
    130                 135                 140

Val Pro Pro Ala Pro Thr Arg Pro Ser Cys Pro Ala Val Ala Glu Ile
145                 150                 155                 160

Pro Leu Arg Met Val Ser Glu Glu Met Glu Glu Gln Val His Ser Ile
```

-continued

```
                165                 170                 175
Arg Gly Ser Ser Ser Ala Asn Pro Val Asn Ser Val Arg Arg Lys Ser
                180                 185                 190
Cys Leu Val Lys Glu Val Glu Lys Met Lys Asn Lys Arg Glu Glu Lys
                195                 200                 205
Lys Ala Gln Asn Ser Glu Met Arg Met Lys Arg Ala Gln Glu Tyr Asp
                210                 215                 220
Ser Ser Phe Pro Asn Trp Glu Phe Ala Arg Met Ile Lys Glu Phe Arg
225                 230                 235                 240
Ala Thr Leu Glu Cys His Pro Leu Thr Met Thr Asp Pro Ile Glu Glu
                245                 250                 255
His Arg Ile Cys Val Cys Val Arg Lys Arg Pro Leu Asn Lys Gln Glu
                260                 265                 270
Leu Ala Lys Lys Glu Ile Asp Val Ile Ser Ile Pro Ser Lys Cys Leu
                275                 280                 285
Leu Leu Val His Glu Pro Lys Leu Lys Val Asp Leu Thr Lys Tyr Leu
                290                 295                 300
Glu Asn Gln Ala Phe Cys Phe Asp Phe Ala Phe Asp Glu Thr Ala Ser
305                 310                 315                 320
Asn Glu Val Val Tyr Arg Phe Thr Ala Arg Pro Leu Val Gln Thr Ile
                325                 330                 335
Phe Glu Gly Gly Lys Ala Thr Cys Phe Ala Tyr Gly Gln Thr Gly Ser
                340                 345                 350
Gly Lys Thr His Thr Met Gly Gly Asp Leu Ser Gly Lys Ala Gln Asn
                355                 360                 365
Ala Ser Lys Gly Ile Tyr Ala Met Ala Ser Arg Asp Val Phe Leu Leu
                370                 375                 380
Lys Asn Gln Pro Cys Tyr Arg Lys Leu Gly Leu Glu Val Tyr Val Thr
385                 390                 395                 400
Phe Phe Glu Ile Tyr Asn Gly Lys Leu Phe Asp Leu Leu Asn Lys Lys
                405                 410                 415
Ala Lys Leu Arg Val Leu Glu Asp Gly Lys Gln Gln Val Gln Val Val
                420                 425                 430
Gly Leu Gln Glu His Leu Val Asn Ser Ala Asp Asp Val Ile Lys Met
                435                 440                 445
Leu Asp Met Gly Ser Ala Cys Arg Thr Ser Gly Gln Thr Phe Ala Asn
                450                 455                 460
Ser Asn Ser Ser Arg Ser His Ala Cys Phe Gln Ile Ile Leu Arg Ala
465                 470                 475                 480
Lys Gly Arg Met His Gly Lys Phe Ser Leu Val Asp Leu Ala Gly Asn
                485                 490                 495
Glu Arg Gly Ala Asp Thr Ser Ser Ala Asp Arg Gln Thr Arg Met Glu
                500                 505                 510
Gly Ala Glu Ile Asn Lys Ser Leu Leu Ala Leu Lys Glu Cys Ile Arg
                515                 520                 525
Ala Leu Gly Gln Asn Lys Ala His Thr Pro Phe Arg Glu Ser Lys Leu
                530                 535                 540
Thr Gln Val Leu Arg Asp Ser Phe Ile Gly Glu Asn Ser Arg Thr Cys
545                 550                 555                 560
Met Ile Ala Thr Ile Ser Pro Gly Ile Ser Ser Cys Glu Tyr Thr Leu
                565                 570                 575
Asn Thr Leu Arg Tyr Ala Asp Arg Val Lys Glu Leu Ser Pro His Ser
                580                 585                 590
```

```
Gly Pro Ser Gly Glu Gln Leu Ile Gln Met Glu Thr Glu Glu Met Glu
            595                 600                 605

Ala Cys Ser Asn Gly Ala Leu Ile Pro Gly Asn Leu Ser Lys Glu Glu
            610                 615                 620

Glu Glu Leu Ser Ser Gln Met Ser Ser Phe Asn Glu Ala Met Thr Gln
625                 630                 635                 640

Ile Arg Glu Leu Glu Lys Ala Met Glu Leu Lys Glu Ile Ile
            645                 650                 655

Gln Gln Gly Pro Asp Trp Leu Glu Leu Ser Glu Met Thr Glu Gln Pro
            660                 665                 670

Asp Tyr Asp Leu Glu Thr Phe Val Asn Lys Ala Glu Ser Ala Leu Ala
            675                 680                 685

Gln Gln Ala Lys His Phe Ser Ala Leu Arg Asp Val Ile Lys Ala Leu
            690                 695                 700

Arg Leu Ala Met Gln Leu Glu Glu Gln Ala Ser Arg Gln Ile Ser Ser
705                 710                 715                 720

Lys Lys Arg Pro Gln
            725

<210> SEQ ID NO 21
<211> LENGTH: 752
<212> TYPE: PRT
<213> ORGANISM: Homo sapiens

<400> SEQUENCE: 21

Arg Val Lys Ala Thr Leu Ser Glu Arg Lys Ile Gly Asp Ser Cys Asp
1               5                   10                  15

Lys Asp Leu Pro Leu Lys Phe Cys Glu Phe Pro Gln Lys Thr Ile Met
            20                  25                  30

Pro Gly Phe Lys Thr Thr Val Tyr Val Ser His Ile Asn Asp Leu Ser
            35                  40                  45

Asp Phe Tyr Val Gln Leu Ile Glu Asp Glu Ala Glu Ile Ser His Leu
        50                  55                  60

Ser Glu Arg Leu Asn Ser Val Lys Thr Arg Pro Glu Tyr Tyr Val Gly
65                  70                  75                  80

Pro Pro Leu Gln Arg Gly Asp Met Ile Cys Ala Val Phe Pro Glu Asp
            85                  90                  95

Asn Leu Trp Tyr Arg Ala Val Ile Lys Glu Gln Gln Pro Asn Asp Leu
            100                 105                 110

Leu Ser Val Gln Phe Ile Asp Tyr Gly Asn Val Ser Val Val His Thr
        115                 120                 125

Asn Lys Ile Gly Arg Leu Asp Leu Val Asn Ala Ile Leu Pro Gly Leu
130                 135                 140

Cys Ile His Cys Ser Leu Gln Gly Phe Glu Val Pro Asp Asn Lys Asn
145                 150                 155                 160

Ser Lys Lys Met Met His Tyr Phe Ser Gln Arg Thr Ser Glu Ala Ala
            165                 170                 175

Ile Arg Cys Glu Phe Val Lys Phe Gln Asp Arg Trp Glu Val Ile Leu
        180                 185                 190

Ala Asp Glu His Gly Ile Ile Ala Asp Asp Met Ile Ser Arg Tyr Ala
        195                 200                 205

Leu Ser Glu Lys Ser Gln Val Glu Leu Ser Thr Gln Val Ile Lys Ser
        210                 215                 220

Ala Ser Ser Lys Ser Val Asn Lys Ser Asp Ile Asp Thr Ser Val Phe
```

```
                225                 230                 235                 240
Leu Asn Trp Tyr Asn Pro Glu Lys Lys Met Ile Arg Ala Tyr Ala Thr
                245                 250                 255
Val Ile Asp Gly Pro Glu Tyr Phe Trp Cys Gln Phe Ala Asp Thr Glu
            260                 265                 270
Lys Leu Gln Cys Leu Glu Val Glu Val Gln Thr Ala Gly Glu Gln Val
        275                 280                 285
Ala Asp Arg Arg Asn Cys Ile Pro Cys Pro Tyr Ile Gly Asp Pro Cys
    290                 295                 300
Ile Val Arg Tyr Arg Glu Asp Gly His Tyr Tyr Arg Ala Leu Ile Thr
305                 310                 315                 320
Asn Ile Cys Glu Asp Tyr Leu Val Ser Val Arg Leu Val Asp Phe Gly
                325                 330                 335
Asn Ile Glu Asp Cys Val Asp Pro Lys Ala Leu Trp Ala Ile Pro Ser
            340                 345                 350
Glu Leu Leu Ser Val Pro Met Gln Ala Phe Pro Cys Cys Leu Ser Gly
        355                 360                 365
Phe Asn Ile Ser Glu Gly Leu Cys Ser Gln Glu Gly Asn Asp Tyr Phe
    370                 375                 380
Tyr Glu Ile Ile Thr Glu Asp Val Leu Glu Ile Thr Ile Leu Glu Ile
385                 390                 395                 400
Arg Arg Asp Val Cys Asp Ile Pro Leu Ala Ile Val Asp Leu Lys Ser
                405                 410                 415
Lys Gly Lys Ser Ile Asn Glu Lys Met Glu Lys Tyr Ser Lys Thr Gly
            420                 425                 430
Ile Lys Ser Ala Leu Pro Tyr Glu Asn Ile Asp Ser Glu Ile Lys Gln
        435                 440                 445
Thr Leu Gly Ser Tyr Asn Leu Asp Val Gly Leu Lys Lys Leu Ser Asn
    450                 455                 460
Lys Ala Val Gln Asn Lys Ile Tyr Met Glu Gln Gln Thr Asp Glu Leu
465                 470                 475                 480
Ala Glu Ile Thr Glu Lys Asp Val Asn Ile Ile Gly Thr Lys Pro Ser
                485                 490                 495
Asn Phe Arg Asp Pro Lys Thr Asp Asn Ile Cys Glu Gly Phe Glu Asn
            500                 505                 510
Pro Cys Lys Asp Lys Ile Asp Thr Glu Glu Leu Glu Gly Glu Leu Glu
        515                 520                 525
Cys His Leu Val Asp Lys Ala Glu Phe Asp Asp Lys Tyr Leu Ile Thr
    530                 535                 540
Gly Phe Asn Thr Leu Leu Pro His Ala Asn Glu Thr Lys Glu Ile Leu
545                 550                 555                 560
Glu Leu Asn Ser Leu Glu Val Pro Leu Ser Pro Asp Asp Glu Ser Lys
                565                 570                 575
Glu Phe Leu Glu Leu Glu Ser Ile Glu Leu Gln Asn Ser Leu Val Val
            580                 585                 590
Asp Glu Glu Lys Gly Glu Leu Ser Pro Val Pro Pro Asn Val Pro Leu
        595                 600                 605
Ser Gln Glu Cys Val Thr Lys Gly Ala Met Glu Leu Phe Thr Leu Gln
    610                 615                 620
Leu Pro Leu Ser Cys Glu Ala Glu Lys Gln Pro Glu Leu Glu Leu Pro
625                 630                 635                 640
Thr Ala Gln Leu Pro Leu Asp Asp Lys Met Asp Pro Leu Ser Leu Gly
                645                 650                 655
```

```
Val Ser Gln Lys Ala Gln Glu Ser Met Cys Thr Glu Asp Met Arg Lys
            660                 665                 670

Ser Ser Cys Val Glu Ser Phe Asp Asp Gln Arg Arg Met Ser Leu His
            675                 680                 685

Leu His Gly Ala Asp Cys Asp Pro Lys Thr Gln Asn Glu Met Asn Ile
            690                 695                 700

Cys Glu Glu Glu Phe Val Glu Tyr Lys Asn Arg Asp Ala Ile Ser Ala
705                 710                 715                 720

Leu Met Pro Phe Ser Leu Arg Lys Lys Ala Val Met Glu Ala Ser Thr
                725                 730                 735

Ile Met Val Tyr Gln Ile Ile Phe Gln Asn Tyr Arg Thr Pro Thr Leu
            740                 745                 750

<210> SEQ ID NO 22
<211> LENGTH: 286
<212> TYPE: PRT
<213> ORGANISM: Homo sapiens

<400> SEQUENCE: 22

Ala Glu Val Lys Thr Pro Phe Asp Leu Ala Lys Ala Gln Glu Asn Ser
1               5                   10                  15

Asn Ser Val Lys Lys Lys Thr Lys Phe Val Asn Leu Tyr Thr Arg Glu
            20                  25                  30

Arg Gln Asp Arg Leu Ala Val Leu Leu Pro Gly Arg His Pro Cys Asp
        35                  40                  45

Cys Leu Gly Gln Lys His Lys Leu Ile Asn Asn Cys Leu Ile Cys Gly
    50                  55                  60

Arg Ile Val Cys Glu Gln Glu Gly Ser Gly Pro Cys Leu Phe Cys Gly
65                  70                  75                  80

Thr Leu Val Cys Thr His Glu Glu Gln Asp Ile Leu Gln Arg Asp Ser
                85                  90                  95

Asn Lys Ser Gln Lys Leu Leu Lys Lys Leu Met Ser Gly Val Glu Asn
            100                 105                 110

Ser Gly Lys Val Asp Ile Ser Thr Lys Asp Leu Leu Pro His Gln Glu
        115                 120                 125

Leu Arg Ile Lys Ser Gly Leu Glu Lys Ala Ile Lys His Lys Asp Lys
    130                 135                 140

Leu Leu Glu Phe Asp Arg Thr Ser Ile Arg Arg Thr Gln Val Ile Asp
145                 150                 155                 160

Asp Glu Ser Asp Tyr Phe Ala Ser Asp Ser Asn Gln Trp Leu Ser Lys
                165                 170                 175

Leu Glu Arg Glu Thr Leu Gln Lys Arg Glu Glu Leu Arg Glu Leu
            180                 185                 190

Arg His Ala Ser Arg Leu Ser Lys Lys Val Thr Ile Asp Phe Ala Gly
        195                 200                 205

Arg Lys Ile Leu Glu Glu Glu Asn Ser Leu Ala Glu Tyr His Ser Arg
    210                 215                 220

Leu Asp Glu Thr Ile Gln Ala Ile Ala Asn Gly Thr Leu Asn Gln Pro
225                 230                 235                 240

Leu Thr Lys Leu Asp Arg Ser Ser Glu Glu Pro Leu Gly Val Leu Val
                245                 250                 255

Asn Pro Asn Met Tyr Gln Ser Pro Pro Gln Trp Leu Thr Thr Gln Val
            260                 265                 270

Gln Pro His Arg Arg Arg Leu Ser Val Leu Gln Asp Leu Asp
```

-continued

```
              275                 280                 285

<210> SEQ ID NO 23
<211> LENGTH: 197
<212> TYPE: PRT
<213> ORGANISM: Homo sapiens

<400> SEQUENCE: 23

Pro Ser Lys Leu Gln Lys Asn Lys Gln Arg Leu Arg Asn Asp Pro Leu
1               5                   10                  15

Asn Gln Asn Lys Gly Lys Pro Asp Leu Asn Thr Thr Leu Pro Ile Arg
            20                  25                  30

Gln Thr Ala Ser Ile Phe Lys Gln Pro Val Thr Lys Val Thr Asn His
        35                  40                  45

Pro Ser Asn Lys Val Lys Ser Asp Pro Gln Arg Met Asn Glu Gln Pro
    50                  55                  60

Arg Gln Leu Phe Trp Glu Lys Arg Leu Gln Gly Leu Ser Ala Ser Asp
65                  70                  75                  80

Val Thr Glu Gln Ile Ile Lys Thr Met Glu Leu Pro Lys Gly Leu Gln
                85                  90                  95

Gly Val Gly Pro Gly Ser Asn Asp Glu Thr Leu Leu Ser Ala Val Ala
            100                 105                 110

Ser Ala Leu His Thr Ser Ser Ala Pro Ile Thr Gly Gln Val Ser Ala
        115                 120                 125

Ala Val Glu Lys Asn Pro Ala Val Trp Leu Asn Thr Ser Gln Pro Leu
    130                 135                 140

Cys Lys Ala Phe Ile Val Thr Asp Glu Asp Ile Arg Lys Gln Glu Glu
145                 150                 155                 160

Arg Val Gln Gln Val Arg Lys Lys Leu Glu Glu Ala Leu Met Ala Asp
                165                 170                 175

Ile Leu Ser Arg Ala Ala Asp Thr Glu Glu Met Asp Ile Glu Met Asp
            180                 185                 190

Ser Gly Asp Glu Ala
        195

<210> SEQ ID NO 24
<211> LENGTH: 353
<212> TYPE: PRT
<213> ORGANISM: Homo sapiens
<220> FEATURE:
<221> NAME/KEY: MISC_FEATURE
<222> LOCATION: (76)..(76)
<223> OTHER INFORMATION: Xaa = any amino acid

<400> SEQUENCE: 24

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Xaa Thr Ser Ser Ser
65                  70                  75                  80

Tyr Thr Gly Gly Pro Cys Thr Ser Pro Leu Leu Ala Pro Val Ile Phe
                85                  90                  95
```

```
Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Cys Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

His Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala

<210> SEQ ID NO 25
<211> LENGTH: 545
<212> TYPE: PRT
<213> ORGANISM: Homo sapiens

<400> SEQUENCE: 25

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
                20                  25                  30

Glu Asp Leu Gln Glu Leu Asn Asp Arg Leu Ala Val Tyr Ile Asp Arg
            35                  40                  45

Val Arg Ser Leu Glu Thr Glu Asn Ala Gly Leu Arg Leu Arg Ile Thr
        50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110
```

```
Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
                180                 185                 190

Ala Glu Asn Arg Leu Gln Thr Met Lys Glu Glu Leu Asp Phe Gln Lys
            195                 200                 205

Asn Ile Tyr Ser Glu Glu Leu Arg Glu Thr Lys Arg Arg His Glu Thr
210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
                260                 265                 270

Asn Ala Arg Gln Ser Ala Glu Arg Asn Ser Asn Leu Val Gly Ala Ala
            275                 280                 285

His Glu Glu Leu Gln Gln Ser Arg Ile Arg Ile Asp Ser Leu Ser Ala
290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
                340                 345                 350

Gln Gln Gln Leu Asp Glu Tyr Gln Glu Leu Leu Asp Ile Lys Leu Ala
            355                 360                 365

Leu Asp Met Glu Ile His Ala Tyr Arg Lys Leu Leu Glu Gly Glu Glu
370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
                420                 425                 430

His Ala Arg Thr Ser Gly Arg Val Ala Val Glu Glu Val Asp Glu Glu
            435                 440                 445

Gly Lys Phe Val Arg Leu Arg Asn Lys Ser Asn Glu Asp Gln Ser Met
450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Arg Thr
515                 520                 525

Ala Leu Ile Asn Ser Thr Gly Glu Glu Val Ala Met Arg Lys Leu Val
```

Arg
545

<210> SEQ ID NO 26
<211> LENGTH: 1227
<212> TYPE: PRT
<213> ORGANISM: Homo sapiens

<400> SEQUENCE: 26

| Gln | Gly | Ala | Gln | Arg | Gly | Ala | Arg | Val | Gly | Ala | Ala | Met | Gly | Leu | Arg |
|---|---|---|---|---|---|---|---|---|---|---|---|---|---|---|---|
| 1 | | | | 5 | | | | | 10 | | | | | 15 | |

| Arg | Ser | Gly | Asp | Ser | Arg | Glu | Pro | Ser | Gly | Pro | Gly | Glu | Arg | Val |
|---|---|---|---|---|---|---|---|---|---|---|---|---|---|---|
| | | | 20 | | | | 25 | | | | | 30 | | |

| Phe | Ser | Gly | Pro | Arg | Pro | Pro | Ala | Arg | Gly | Ala | Gly | Ala | Pro | Ala |
|---|---|---|---|---|---|---|---|---|---|---|---|---|---|---|
| | | 35 | | | | | 40 | | | | | 45 | | |

| Pro | Val | Ala | Gly | Ala | Val | Ala | Gly | Cys | Gly | Gly | Gln | Asp | His | Val |
|---|---|---|---|---|---|---|---|---|---|---|---|---|---|---|
| | 50 | | | | | 55 | | | | | 60 | | | |

| Gly | Ser | Pro | Leu | Arg | Arg | Gly | Ser | Gly | Leu | Arg | Asp | Ala | Ala | Ala |
|---|---|---|---|---|---|---|---|---|---|---|---|---|---|---|
| 65 | | | | | 70 | | | | | 75 | | | | | 80 |

| Glu | Ala | Val | Glu | Pro | Ala | Ala | Arg | Glu | Leu | Phe | Glu | Ala | Cys | Arg | Asn |
|---|---|---|---|---|---|---|---|---|---|---|---|---|---|---|---|
| | | | | 85 | | | | | 90 | | | | | 95 | |

| Gly | Asp | Val | Glu | Arg | Val | Lys | Arg | Leu | Val | Thr | Pro | Glu | Lys | Val | Asn |
|---|---|---|---|---|---|---|---|---|---|---|---|---|---|---|---|
| | | | 100 | | | | | 105 | | | | | 110 | | |

| Ser | Arg | Asp | Thr | Ala | Gly | Arg | Lys | Ser | Thr | Pro | Leu | His | Phe | Ala | Ala |
|---|---|---|---|---|---|---|---|---|---|---|---|---|---|---|---|
| | | | 115 | | | | | 120 | | | | | 125 | | |

| Gly | Phe | Gly | Arg | Lys | Asp | Val | Val | Glu | Tyr | Leu | Leu | Gln | Asn | Gly | Ala |
|---|---|---|---|---|---|---|---|---|---|---|---|---|---|---|---|
| | | 130 | | | | | 135 | | | | | 140 | | | |

| Asn | Val | Gln | Ala | Arg | Asp | Asp | Gly | Gly | Leu | Ile | Pro | Leu | His | Asn | Ala |
|---|---|---|---|---|---|---|---|---|---|---|---|---|---|---|---|
| 145 | | | | | 150 | | | | | 155 | | | | | 160 |

| Cys | Ser | Phe | Gly | His | Ala | Glu | Val | Val | Asn | Leu | Leu | Leu | Arg | His | Gly |
|---|---|---|---|---|---|---|---|---|---|---|---|---|---|---|---|
| | | | | 165 | | | | | 170 | | | | | 175 | |

| Ala | Asp | Pro | Asn | Ala | Arg | Asp | Asn | Trp | Asn | Tyr | Thr | Pro | Leu | His | Glu |
|---|---|---|---|---|---|---|---|---|---|---|---|---|---|---|---|
| | | | 180 | | | | | 185 | | | | | 190 | | |

| Ala | Ala | Ile | Lys | Gly | Lys | Ile | Asp | Val | Cys | Ile | Val | Leu | Leu | Gln | His |
|---|---|---|---|---|---|---|---|---|---|---|---|---|---|---|---|
| | | 195 | | | | | 200 | | | | | 205 | | | |

| Gly | Ala | Glu | Pro | Thr | Ile | Arg | Asn | Thr | Asp | Gly | Arg | Thr | Ala | Leu | Asp |
|---|---|---|---|---|---|---|---|---|---|---|---|---|---|---|---|
| | 210 | | | | | 215 | | | | | 220 | | | | |

| Leu | Ala | Asp | Pro | Ser | Ala | Lys | Ala | Val | Leu | Thr | Gly | Glu | Tyr | Lys | Lys |
|---|---|---|---|---|---|---|---|---|---|---|---|---|---|---|---|
| 225 | | | | | 230 | | | | | 235 | | | | | 240 |

| Asp | Glu | Leu | Leu | Glu | Ser | Ala | Arg | Ser | Gly | Asn | Glu | Glu | Lys | Met | Met |
|---|---|---|---|---|---|---|---|---|---|---|---|---|---|---|---|
| | | | | 245 | | | | | 250 | | | | | 255 | |

| Ala | Leu | Leu | Thr | Pro | Leu | Asn | Val | Asn | Cys | His | Ala | Ser | Asp | Gly | Arg |
|---|---|---|---|---|---|---|---|---|---|---|---|---|---|---|---|
| | | | 260 | | | | | 265 | | | | | 270 | | |

| Lys | Ser | Thr | Pro | Leu | His | Leu | Ala | Ala | Gly | Tyr | Asn | Arg | Val | Lys | Ile |
|---|---|---|---|---|---|---|---|---|---|---|---|---|---|---|---|
| | | 275 | | | | | 280 | | | | | 285 | | | |

| Val | Gln | Leu | Leu | Leu | Gln | His | Gly | Ala | Asp | Val | His | Ala | Lys | Asp | Lys |
|---|---|---|---|---|---|---|---|---|---|---|---|---|---|---|---|
| | 290 | | | | | 295 | | | | | 300 | | | | |

| Gly | Asp | Leu | Val | Pro | Leu | His | Asn | Ala | Cys | Ser | Tyr | Gly | His | Tyr | Glu |
|---|---|---|---|---|---|---|---|---|---|---|---|---|---|---|---|
| 305 | | | | | 310 | | | | | 315 | | | | | 320 |

| Val | Thr | Glu | Leu | Leu | Val | Lys | His | Gly | Ala | Cys | Val | Asn | Ala | Met | Asp |
|---|---|---|---|---|---|---|---|---|---|---|---|---|---|---|---|
| | | | | 325 | | | | | 330 | | | | | 335 | |

| Leu | Trp | Gln | Phe | Thr | Pro | Leu | His | Glu | Ala | Ala | Ser | Lys | Asn | Arg | Val |
|---|---|---|---|---|---|---|---|---|---|---|---|---|---|---|---|
| | | | 340 | | | | | 345 | | | | | 350 | | |

```
Glu Val Cys Ser Leu Leu Leu Ser Tyr Gly Ala Asp Pro Thr Leu Leu
            355                 360                 365

Asn Cys His Asn Lys Ser Ala Ile Asp Leu Ala Pro Thr Pro Gln Leu
            370                 375                 380

Lys Glu Arg Leu Ala Tyr Glu Phe Lys Gly His Ser Leu Leu Gln Ala
385                 390                 395                 400

Ala Arg Glu Ala Asp Val Thr Arg Ile Lys Lys His Leu Ser Leu Glu
                405                 410                 415

Met Val Asn Phe Lys His Pro Gln Thr His Glu Thr Ala Leu His Cys
                420                 425                 430

Ala Ala Ala Ser Pro Tyr Pro Lys Arg Lys Gln Ile Cys Glu Leu Leu
            435                 440                 445

Leu Arg Lys Gly Ala Asn Ile Asn Glu Lys Thr Lys Glu Phe Leu Thr
            450                 455                 460

Pro Leu His Val Ala Ser Glu Lys Ala His Asn Asp Val Val Glu Val
465                 470                 475                 480

Val Val Lys His Glu Ala Lys Val Asn Ala Leu Asp Asn Leu Gly Gln
                485                 490                 495

Thr Ser Leu His Arg Ala Ala Tyr Cys Gly His Leu Gln Thr Cys Arg
            500                 505                 510

Leu Leu Leu Ser Tyr Gly Cys Asp Pro Asn Ile Ile Ser Leu Gln Gly
            515                 520                 525

Phe Thr Ala Leu Gln Met Gly Asn Glu Asn Val Gln Gln Leu Leu Gln
            530                 535                 540

Glu Gly Ile Ser Leu Gly Asn Ser Glu Ala Asp Arg Gln Leu Leu Glu
545                 550                 555                 560

Ala Ala Lys Ala Gly Asp Val Glu Thr Val Lys Lys Leu Cys Thr Val
                565                 570                 575

Gln Ser Val Asn Cys Arg Asp Ile Glu Gly Arg Gln Ser Thr Pro Leu
            580                 585                 590

His Phe Ala Ala Gly Tyr Asn Arg Val Ser Val Val Glu Tyr Leu Leu
            595                 600                 605

Gln His Gly Ala Asp Val His Ala Lys Asp Lys Gly Gly Leu Val Pro
610                 615                 620

Leu His Asn Ala Cys Ser Tyr Gly His Tyr Glu Val Ala Glu Leu Leu
625                 630                 635                 640

Val Lys His Gly Ala Val Val Asn Val Ala Asp Leu Trp Lys Phe Thr
                645                 650                 655

Pro Leu His Glu Ala Ala Lys Gly Lys Tyr Glu Ile Cys Lys Leu
            660                 665                 670

Leu Leu Gln His Gly Ala Asp Pro Thr Lys Lys Asn Arg Asp Gly Asn
            675                 680                 685

Thr Pro Leu Asp Leu Val Lys Asp Gly Asp Thr Asp Ile Gln Asp Leu
690                 695                 700

Leu Arg Gly Asp Ala Ala Leu Leu Asp Ala Ala Lys Lys Gly Cys Leu
705                 710                 715                 720

Ala Arg Val Lys Lys Leu Ser Ser Pro Asp Asn Val Asn Cys Arg Asp
                725                 730                 735

Thr Gln Gly Arg His Ser Thr Pro Leu His Leu Ala Ala Gly Tyr Asn
            740                 745                 750

Asn Leu Glu Val Ala Glu Tyr Leu Leu Gln His Gly Ala Asp Val Asn
            755                 760                 765

Ala Gln Asp Lys Gly Gly Leu Ile Pro Leu His Asn Ala Ala Ser Tyr
```

-continued

```
              770                 775                 780
Gly His Val Asp Val Ala Ala Leu Leu Ile Lys Tyr Asn Ala Cys Val
785                 790                 795                 800
Asn Ala Thr Asp Lys Trp Ala Phe Thr Pro Leu His Glu Ala Ala Gln
                    805                 810                 815
Lys Gly Arg Thr Gln Leu Cys Ala Leu Leu Ala His Gly Ala Asp
                    820                 825                 830
Pro Thr Leu Lys Asn Gln Glu Gly Gln Thr Pro Leu Asp Leu Val Ser
                    835                 840                 845
Ala Asp Asp Val Ser Ala Leu Leu Thr Ala Ala Met Pro Pro Ser Ala
850                 855                 860
Leu Pro Ser Cys Tyr Lys Pro Gln Val Leu Asn Gly Val Arg Ser Pro
865                 870                 875                 880
Gly Ala Thr Ala Asp Ala Leu Ser Ser Gly Pro Ser Pro Ser Ser
                    885                 890                 895
Leu Ser Ala Ala Ser Ser Leu Asp Asn Leu Ser Gly Ser Phe Ser Glu
                    900                 905                 910
Leu Ser Ser Val Val Ser Ser Ser Gly Thr Glu Gly Ala Ser Ser Leu
                    915                 920                 925
Glu Lys Lys Glu Val Pro Gly Val Asp Phe Ser Ile Thr Gln Phe Val
930                 935                 940
Arg Asn Leu Gly Leu Glu His Leu Met Asp Ile Phe Glu Arg Glu Gln
945                 950                 955                 960
Ile Thr Leu Asp Val Leu Val Glu Met Gly His Lys Glu Leu Lys Glu
                    965                 970                 975
Ile Gly Ile Asn Ala Tyr Gly His Arg His Lys Leu Ile Lys Gly Val
                    980                 985                 990
Glu Arg Leu Ile Ser Gly Gln Gln  Gly Leu Asn Pro Tyr  Leu Thr Leu
                    995                 1000                1005
Asn Thr  Ser Gly Ser Gly Thr  Ile Leu Ile Asp Leu  Ser Pro Asp
    1010                1015                1020
Asp Lys  Glu Phe Gln Ser Val  Glu Glu Glu Met Gln  Ser Thr Val
    1025                1030                1035
Arg Glu  His Arg Asp Gly Gly  His Ala Gly Gly Ile  Phe Asn Arg
    1040                1045                1050
Tyr Asn  Ile Leu Lys Ile Gln  Lys Val Cys Asn Lys  Lys Leu Trp
    1055                1060                1065
Glu Arg  Tyr Thr His Arg Arg  Lys Glu Val Ser Glu  Glu Asn His
    1070                1075                1080
Asn His  Ala Asn Glu Arg Met  Leu Phe His Gly Ser  Pro Phe Val
    1085                1090                1095
Asn Ala  Ile Ile His Lys Gly  Phe Asp Glu Arg His  Ala Tyr Ile
    1100                1105                1110
Gly Gly  Met Phe Gly Ala Gly  Ile Tyr Phe Ala Glu  Asn Ser Ser
    1115                1120                1125
Lys Ser  Asn Gln Tyr Val Tyr  Gly Ile Gly Gly Gly  Thr Gly Val
    1130                1135                1140
Gln Phe  Thr Lys Thr Asp Leu  Val Thr Phe Ala Thr  Ala Ala Ala
    1145                1150                1155
Leu Leu  Pro Gly Asn Leu Gly  Lys Val Phe Pro Ala  Val Gln Cys
    1160                1165                1170
Asn Glu  Asn Gly Thr Ser Pro  Pro Gly His His Ser  Val Thr Gly
    1175                1180                1185
```

```
Arg Pro Ser Val Asn Gly Leu Ala Leu Ala Glu Tyr Val Ile Tyr
    1190                1195                1200

Arg Gly Glu Gln Ala Tyr Pro Glu Tyr Leu Ile Thr Tyr Gln Ile
    1205                1210                1215

Met Arg Pro Glu Gly Met Val Asp Gly
    1220                1225

<210> SEQ ID NO 27
<211> LENGTH: 290
<212> TYPE: PRT
<213> ORGANISM: Homo sapiens

<400> SEQUENCE: 27

His Ile Gln Lys Gln Lys His Phe Asn Glu Arg Glu Ala Ser Arg Val
1               5                   10                  15

Val Arg Asp Val Ala Ala Ala Leu Asp Phe Leu His Thr Lys Gly Ile
            20                  25                  30

Ala His Arg Asp Leu Lys Pro Glu Asn Ile Leu Cys Glu Ser Pro Glu
        35                  40                  45

Lys Val Ser Pro Val Lys Ile Cys Asp Phe Asp Leu Gly Ser Gly Met
    50                  55                  60

Lys Leu Asn Asn Ser Cys Thr Pro Ile Thr Thr Pro Glu Leu Thr Thr
65                  70                  75                  80

Pro Cys Gly Ser Ala Glu Tyr Met Ala Pro Glu Val Val Glu Val Phe
                85                  90                  95

Thr Asp Gln Ala Thr Phe Tyr Asp Lys Arg Cys Asp Leu Trp Ser Leu
            100                 105                 110

Gly Val Val Leu Tyr Ile Met Leu Ser Gly Tyr Pro Pro Phe Val Gly
        115                 120                 125

His Cys Gly Ala Asp Cys Gly Trp Asp Arg Gly Glu Val Cys Arg Val
    130                 135                 140

Cys Gln Asn Lys Leu Phe Glu Ser Ile Gln Glu Gly Lys Tyr Glu Phe
145                 150                 155                 160

Pro Asp Lys Asp Trp Ala His Ile Ser Ser Glu Ala Lys Asp Leu Ile
                165                 170                 175

Ser Lys Leu Leu Val Arg Asp Ala Lys Gln Lys Leu Ser Ala Ala Gln
            180                 185                 190

Val Leu Gln His Pro Trp Val Gln Gly Gln Ala Pro Glu Lys Gly Leu
        195                 200                 205

Pro Thr Pro Gln Val Leu Gln Arg Asn Ser Ser Thr Met Asp Leu Thr
    210                 215                 220

Leu Phe Ala Ala Glu Ala Ile Ala Leu Asn Arg Gln Leu Ser Gln His
225                 230                 235                 240

Glu Glu Asn Glu Leu Ala Glu Glu Pro Glu Ala Leu Ala Asp Gly Leu
                245                 250                 255

Cys Ser Met Lys Leu Ser Pro Pro Cys Lys Ser Arg Leu Ala Arg Arg
            260                 265                 270

Arg Ala Leu Ala Gln Ala Gly Arg Gly Glu Asn Arg Ser Pro Pro Thr
        275                 280                 285

Ala Leu
    290

<210> SEQ ID NO 28
<211> LENGTH: 188
<212> TYPE: PRT
```

<213> ORGANISM: Homo sapiens

<400> SEQUENCE: 28

Met Asn Gly Asp Asp Ala Phe Ala Arg Arg Pro Thr Val Gly Ala Gln
1               5                   10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile His Glu Arg Ser Gly Pro Lys Arg Gly
145                 150                 155                 160

Glu His Ala Trp Thr His Arg Leu Arg Glu Arg Lys Gln Leu Val Ile
                165                 170                 175

Tyr Glu Glu Ile Ser Asp Pro Glu Glu Asp Asp Glu
            180                 185

<210> SEQ ID NO 29
<211> LENGTH: 314
<212> TYPE: PRT
<213> ORGANISM: Homo sapiens

<400> SEQUENCE: 29

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr

```
                    165                 170                 175
Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Pro His Ile Ser Tyr Pro Pro Leu
    290                 295                 300

His Glu Trp Val Leu Arg Glu Gly Glu Glu
305                 310

<210> SEQ ID NO 30
<211> LENGTH: 180
<212> TYPE: PRT
<213> ORGANISM: Homo sapiens

<400> SEQUENCE: 30

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 31
<211> LENGTH: 30
<212> TYPE: PRT
<213> ORGANISM: Homo sapiens
```

```
<400> SEQUENCE: 31

Met Asp Ser Ser Leu Gln Ala Arg Leu Phe Pro Gly Leu Ala Ile Lys
1               5                   10                  15

Ile Gln Arg Ser Asn Gly Leu Ile His Ser Ala Asn Val Arg
            20                  25                  30

<210> SEQ ID NO 32
<211> LENGTH: 12
<212> TYPE: PRT
<213> ORGANISM: Homo sapiens

<400> SEQUENCE: 32

Leu Ala Ile Lys Ile Gln Arg Ser Asn Gly Leu Ile
1               5                   10

<210> SEQ ID NO 33
<211> LENGTH: 30
<212> TYPE: PRT
<213> ORGANISM: Homo sapiens

<400> SEQUENCE: 33

Glu Ile Tyr Asn Gly Lys Leu Phe Asp Leu Leu Asn Lys Lys Ala Lys
1               5                   10                  15

Leu Arg Val Leu Glu Asp Gly Lys Gln Gln Val Gln Val Val
            20                  25                  30

<210> SEQ ID NO 34
<211> LENGTH: 30
<212> TYPE: PRT
<213> ORGANISM: Homo sapiens

<400> SEQUENCE: 34

Lys His Phe Ser Ala Leu Arg Asp Val Ile Lys Ala Leu Arg Leu Ala
1               5                   10                  15

Met Gln Leu Glu Gln Ala Ser Arg Gln Ile Ser Ser Lys
            20                  25                  30

<210> SEQ ID NO 35
<211> LENGTH: 30
<212> TYPE: PRT
<213> ORGANISM: Homo sapiens

<400> SEQUENCE: 35

Thr Lys Gly Lys Glu Ile Asp Phe Asp Val Ala Ala Ile Asn Pro
1               5                   10                  15

Glu Leu Leu Gln Leu Leu Pro Leu His Pro Lys Asp Asn Leu
            20                  25                  30

<210> SEQ ID NO 36
<211> LENGTH: 30
<212> TYPE: PRT
<213> ORGANISM: Homo sapiens

<400> SEQUENCE: 36

Arg Pro Ser Cys Pro Ala Val Ala Glu Ile Pro Leu Arg Met Val Ser
1               5                   10                  15

Glu Glu Met Glu Glu Gln Val His Ser Ile Arg Gly Ser Ser
            20                  25                  30

<210> SEQ ID NO 37
<211> LENGTH: 30
<212> TYPE: PRT
```

```
<213> ORGANISM: Homo sapiens

<400> SEQUENCE: 37

Gln Glu Leu Ala Lys Lys Glu Ile Asp Val Ile Ser Ile Pro Ser Lys
1               5                   10                  15
Cys Leu Leu Leu Val His Glu Pro Lys Leu Lys Val Asp Leu
            20                  25                  30

<210> SEQ ID NO 38
<211> LENGTH: 30
<212> TYPE: PRT
<213> ORGANISM: Homo sapiens

<400> SEQUENCE: 38

Ala Met Ala Ser Arg Asp Val Phe Leu Leu Lys Asn Gln Pro Cys Tyr
1               5                   10                  15
Arg Lys Leu Gly Leu Glu Val Tyr Val Thr Phe Phe Glu Ile
            20                  25                  30

<210> SEQ ID NO 39
<211> LENGTH: 30
<212> TYPE: PRT
<213> ORGANISM: Homo sapiens

<400> SEQUENCE: 39

Arg Met Glu Gly Ala Glu Ile Asn Lys Ser Leu Leu Ala Leu Lys Glu
1               5                   10                  15
Cys Ile Arg Ala Leu Gly Gln Asn Lys Ala His Thr Pro Phe
            20                  25                  30

<210> SEQ ID NO 40
<211> LENGTH: 30
<212> TYPE: PRT
<213> ORGANISM: Homo sapiens

<400> SEQUENCE: 40

Ser Phe Asn Glu Ala Met Thr Gln Ile Arg Glu Leu Glu Glu Lys Ala
1               5                   10                  15
Met Glu Glu Leu Lys Glu Ile Ile Gln Gln Gly Pro Asp Trp
            20                  25                  30

<210> SEQ ID NO 41
<211> LENGTH: 9
<212> TYPE: PRT
<213> ORGANISM: Homo sapiens

<400> SEQUENCE: 41

Ala Ile Asn Pro Glu Leu Leu Gln Leu
1               5

<210> SEQ ID NO 42
<211> LENGTH: 9
<212> TYPE: PRT
<213> ORGANISM: Homo sapiens

<400> SEQUENCE: 42

Leu Leu Leu Val His Glu Pro Lys Leu
1               5

<210> SEQ ID NO 43
<211> LENGTH: 9
<212> TYPE: PRT
<213> ORGANISM: Homo sapiens
```

```
<400> SEQUENCE: 43

Leu Val His Glu Pro Lys Leu Lys Val
1               5

<210> SEQ ID NO 44
<211> LENGTH: 9
<212> TYPE: PRT
<213> ORGANISM: Homo sapiens

<400> SEQUENCE: 44

Ala Met Ala Ser Arg Asp Val Phe Leu
1               5

<210> SEQ ID NO 45
<211> LENGTH: 9
<212> TYPE: PRT
<213> ORGANISM: Homo sapiens

<400> SEQUENCE: 45

Val Leu Glu Asp Gly Lys Gln Gln Val
1               5

<210> SEQ ID NO 46
<211> LENGTH: 9
<212> TYPE: PRT
<213> ORGANISM: Homo sapiens

<400> SEQUENCE: 46

Ser Leu Leu Ala Leu Lys Glu Cys Ile
1               5

<210> SEQ ID NO 47
<211> LENGTH: 9
<212> TYPE: PRT
<213> ORGANISM: Homo sapiens

<400> SEQUENCE: 47

Asn Leu Ser Lys Glu Glu Glu Glu Leu
1               5

<210> SEQ ID NO 48
<211> LENGTH: 9
<212> TYPE: PRT
<213> ORGANISM: Homo sapiens

<400> SEQUENCE: 48

Ile Ile Gln Gln Gly Pro Asp Trp Leu
1               5

<210> SEQ ID NO 49
<211> LENGTH: 9
<212> TYPE: PRT
<213> ORGANISM: Homo sapiens

<400> SEQUENCE: 49

Ala Leu Arg Asp Val Ile Lys Ala Leu
1               5

<210> SEQ ID NO 50
<211> LENGTH: 9
<212> TYPE: PRT
<213> ORGANISM: Homo sapiens

<400> SEQUENCE: 50
```

```
Leu Gln Ala Arg Leu Phe Pro Gly Leu
1               5

<210> SEQ ID NO 51
<211> LENGTH: 9
<212> TYPE: PRT
<213> ORGANISM: Homo sapiens

<400> SEQUENCE: 51

Thr Ile Phe Glu Gly Gly Lys Ala Thr
1               5

<210> SEQ ID NO 52
<211> LENGTH: 9
<212> TYPE: PRT
<213> ORGANISM: Homo sapiens

<400> SEQUENCE: 52

Lys Leu Gly Leu Glu Val Tyr Val Thr
1               5

<210> SEQ ID NO 53
<211> LENGTH: 9
<212> TYPE: PRT
<213> ORGANISM: Homo sapiens

<400> SEQUENCE: 53

Lys Gln Gln Val Gln Val Val Gly Leu
1               5

<210> SEQ ID NO 54
<211> LENGTH: 9
<212> TYPE: PRT
<213> ORGANISM: Homo sapiens

<400> SEQUENCE: 54

Val Val Gly Leu Gln Glu His Leu Val
1               5

<210> SEQ ID NO 55
<211> LENGTH: 9
<212> TYPE: PRT
<213> ORGANISM: Homo sapiens

<400> SEQUENCE: 55

Lys Met Ile Asp Met Gly Ser Ala Cys
1               5

<210> SEQ ID NO 56
<211> LENGTH: 9
<212> TYPE: PRT
<213> ORGANISM: Homo sapiens

<400> SEQUENCE: 56

Arg Met His Gly Lys Phe Ser Leu Val
1               5

<210> SEQ ID NO 57
<211> LENGTH: 9
<212> TYPE: PRT
<213> ORGANISM: Homo sapiens

<400> SEQUENCE: 57

Ala Leu Gly Gln Asn Lys Ala His Thr
```

<210> SEQ ID NO 58
<211> LENGTH: 9
<212> TYPE: PRT
<213> ORGANISM: Homo sapiens

<400> SEQUENCE: 58

Lys Ala Met Glu Glu Leu Lys Glu Ile
1               5

<210> SEQ ID NO 59
<211> LENGTH: 9
<212> TYPE: PRT
<213> ORGANISM: Homo sapiens

<400> SEQUENCE: 59

Phe Val Asn Lys Ala Glu Ser Ala Leu
1               5

<210> SEQ ID NO 60
<211> LENGTH: 9
<212> TYPE: PRT
<213> ORGANISM: Homo sapiens

<400> SEQUENCE: 60

Met Ala Ser Arg Asp Val Phe Leu Leu
1               5

<210> SEQ ID NO 61
<211> LENGTH: 9
<212> TYPE: PRT
<213> ORGANISM: Homo sapiens

<400> SEQUENCE: 61

Arg Leu Phe Pro Gly Leu Ala Ile Lys
1               5

<210> SEQ ID NO 62
<211> LENGTH: 9
<212> TYPE: PRT
<213> ORGANISM: Homo sapiens

<400> SEQUENCE: 62

Ser Ala Asn Val Arg Thr Val Asn Leu
1               5

<210> SEQ ID NO 63
<211> LENGTH: 9
<212> TYPE: PRT
<213> ORGANISM: Homo sapiens

<400> SEQUENCE: 63

Asn Leu Glu Lys Ser Cys Val Ser Val
1               5

<210> SEQ ID NO 64
<211> LENGTH: 9
<212> TYPE: PRT
<213> ORGANISM: Homo sapiens

<400> SEQUENCE: 64

Lys Ile Pro Ala Pro Lys Glu Ser Leu
1               5

```
<210> SEQ ID NO 65
<211> LENGTH: 9
<212> TYPE: PRT
<213> ORGANISM: Homo sapiens

<400> SEQUENCE: 65

Ser Ser Ala Asn Pro Val Asn Ser Val
1               5

<210> SEQ ID NO 66
<211> LENGTH: 9
<212> TYPE: PRT
<213> ORGANISM: Homo sapiens

<400> SEQUENCE: 66

Met Ile Lys Glu Phe Arg Ala Thr Leu
1               5

<210> SEQ ID NO 67
<211> LENGTH: 9
<212> TYPE: PRT
<213> ORGANISM: Homo sapiens

<400> SEQUENCE: 67

Ser Ile Pro Ser Lys Cys Leu Leu Leu
1               5

<210> SEQ ID NO 68
<211> LENGTH: 9
<212> TYPE: PRT
<213> ORGANISM: Homo sapiens

<400> SEQUENCE: 68

Asp Leu Leu Asn Lys Lys Ala Lys Leu
1               5

<210> SEQ ID NO 69
<211> LENGTH: 9
<212> TYPE: PRT
<213> ORGANISM: Homo sapiens

<400> SEQUENCE: 69

Glu Ile Asn Lys Ser Leu Leu Ala Leu
1               5

<210> SEQ ID NO 70
<211> LENGTH: 9
<212> TYPE: PRT
<213> ORGANISM: Homo sapiens

<400> SEQUENCE: 70

Ala Leu Lys Glu Cys Ile Arg Ala Leu
1               5

<210> SEQ ID NO 71
<211> LENGTH: 9
<212> TYPE: PRT
<213> ORGANISM: Homo sapiens

<400> SEQUENCE: 71

Gly Ile Ser Ser Cys Glu Tyr Thr Leu
1               5

<210> SEQ ID NO 72
```

-continued

```
<211> LENGTH: 12
<212> TYPE: PRT
<213> ORGANISM: Homo sapiens

<400> SEQUENCE: 72

Asp Val Ile Lys Ala Leu Arg Leu Ala Met Gln Leu
1               5                   10

<210> SEQ ID NO 73
<211> LENGTH: 10
<212> TYPE: PRT
<213> ORGANISM: Homo sapiens

<400> SEQUENCE: 73

Glu Leu Ala Gly Ile Gly Ile Leu Thr Val
1               5                   10
```

METHOD FOR INDUCING IMMUNE RESPONSE TO NY-CO-58

RELATED APPLICATIONS

This application is a continuation-in-part of U.S. patent application Ser. No. 09/849,602, filed May 4, 2001, now U.S. Pat. 6,794,501, the entire content of which is incorporated herein by reference.

FIELD OF THE INVENTION

The invention relates to the use of polypeptides and/or nucleic acids in methods and compositions that induce and/or enhance an immune response in a subject. The invention in some aspects includes kits that include the polypeptides and/or nucleic acids of the invention that induce and/or enhance an immune response. In some aspects of the invention, the polypeptide and/or nucleic acid molecules of the invention are useful to induce and/or enhance an immune response in a subject who has or is suspected of having cancer.

BACKGROUND OF THE INVENTION

Colon cancer, which is also known as cancer of the large bowel and colorectal cancer, is second only to lung cancer as a cause of cancer death in the United States. Colorectal cancer is a common malignant condition that generally occurs in individuals 50 years of age or older; and the overall incidence rate of colon cancer has not changed substantially during the past 40 years. (Harrison's Principles of Internal Medicine, 14/e, McGraw-Hill Companies, New York, 1998). The treatment of colon cancer once diagnosis is made depends on the extent of the cancer's invasion of the colon tissue, lymph nodes, and metastasis to other organs such as the liver. The survival rate for patients diagnosed with early-stage cancer is about 90% survival after 5 years. The five-year survival rate drops if the cancer is not detected until the cancer has spread beyond the mucosal layer of the colon, and drops significantly further if, when detected, the cancer has spread beyond the colon to the lymph nodes and beyond. Thus, it is critical to diagnose colon cancer at the earliest possible stage to increase the likelihood of a positive prognosis and outcome.

The traditional method of colon cancer diagnosis is through the use of non-invasive or mildly invasive diagnostic tests, more invasive visual examination, and histologic examination of biopsy. Although these tests may detect colon cancers, each has drawbacks that limit its effectiveness as a diagnostic tool. One primary source of difficulty with most of the currently available methods for diagnosing colorectal cancer, is patient reluctance to submit to, or follow through with the procedures, due to the uncomfortable or perceived embarrassing nature of the tests.

Some of the less invasive diagnostic methods include fecal occult blood testing and digital rectal exam. A digital exam may detect tumors at the distal end of the colon/rectum, but is not effective at more proximal levels. The usefulness of tests for occult blood is hampered by the intermittent bleeding patterns of colon cancers, which can result in a high percentage of false negative results. For example, approximately 50 percent of patients with documented colorectal cancers have a negative fecal blood test. In addition, false-positive fecal occult blood tests may also present problems for accurate diagnosis of colon cancer, because a number of non-colon cancer conditions (e.g.: gingivitis, ulcer, or aspirin use) may yield positive test results, resulting in unnecessary invasive follow-up procedures. These limitations of the less-invasive tests for colon cancer may delay a patient's procurement of rapid diagnosis and appropriate colon cancer treatment.

Visual examination of the colon for abnormalities can be performed through endoscopic or radiographic techniques such as rigid proctosigmoidoscopy, flexible sigmoidoscopy, colonoscopy, and barium-contrast enema. These methods are expensive, and uncomfortable, and also carry with them a risk of complications.

Another method of colon cancer diagnosis is the detection of carcinoembryonic antigen (CEA) in a blood sample from a subject, which when present at high levels, may indicate the presence of advanced colon cancer. But CEA levels may also be abnormally high when no cancer is present. Thus, this test is not selective for colon cancer, which limits the test's value as an accurate and reliable diagnostic tool. In addition, elevated CEA levels are not detectable until late-stage colon cancer, when the cure rate is low, treatment options limited, and patient prognosis poor.

More effective techniques for colon cancer diagnosis and evaluation of colon cancer treatments are needed. Although available diagnostic procedures for colon cancer may be partially successful, the methods for detecting colon cancer remain unsatisfactory. There is a critical need for diagnostic tests that can detect colon cancer at its early stages, when appropriate treatment may substantially increase the likelihood of positive outcome for the patient.

SUMMARY OF THE INVENTION

The invention provides methods and compositions to induce and/or enhance an immune response in a subject. The invention is based on our identification of certain cancer-associated polypeptides and the encoding nucleic acid molecules thereof, as antigens that elicit immune responses. The identified antigens can be utilized in methods and compositions that induce and/or enhance an immune response in a subject. The invention in some aspects includes kits that include the polypeptides and/or nucleic acids of the invention that induce and/or enhance an immune response. In some aspects of the invention, the polypeptide and/or nucleic acid molecules of the invention are useful to induce and/or enhance an immune response in a subject who has or is suspected of having cancer.

According to one aspect of the invention, methods of inducing or enhancing an immune response in a subject are provided. The methods include administering to a subject in need of such treatment an isolated polypeptide comprising the amino acid sequence set forth as SEQ ID NO:20, in an amount effective to induce or enhance the immune response in the subject. In some embodiments, the immune response is mediated by HLA class I molecules. In certain embodiments, the immune response is mediated by HLA class II molecules. In some embodiments, the subject has or is suspected of having cancer. In some embodiments, the cancer is colon cancer.

According to another aspect of the invention, a composition is provided. The composition includes an isolated polypeptide comprising the amino acid sequence set forth as SEQ ID NO:20. In some embodiments, the composition also includes a pharmaceutically acceptable carrier. In certain embodiments, the composition also includes an adjuvant.

According to another aspect of the invention, methods of inducing or enhancing an immune response in a subject are provided. The methods include administering to a subject in need of such treatment an isolated immunogenic fragment of a polypeptide comprising the amino acid sequence set forth as SEQ ID NO:20, in an amount effective to induce or enhance the immune response in the subject. In some embodiments, the isolated immunogenic fragment is a HLA class II binding peptide. In certain embodiments, the isolated immunogenic fragment is selected from the group consisting of: SEQ ID NOs: 31, 32, 33, 34, and 72. In some embodiments, the isolated immunogenic fragment is a HLA class I binding peptide. In certain embodiments, the isolated immunogenic fragment is selected from the group consisting of SEQ ID NOs: 46, 50, 52, and 63. In some embodiments, the subject has or is suspected of having cancer. In some embodiments, the cancer is colon cancer.

According to another aspect of the invention, a composition is provided. The composition includes an isolated immunogenic fragment of a polypeptide comprising the amino acid sequence set forth as SEQ ID NO:20. In some embodiments, the composition also includes a pharmaceutically acceptable carrier. In certain embodiments, the composition also includes an adjuvant.

According to another aspect of the invention, compositions are provided. The compositions include an isolated antigen-presenting cell and a peptide comprising the amino acid sequence set forth as SEQ ID NO:20, or immunogenic fragment thereof. In some embodiments, the isolated antigen-presenting cell comprises an HLA-A2 molecule. In certain embodiments, the isolated antigen-presenting cell comprises an HLA-DR molecule. In some embodiments, the HLA-DR molecule is selected from the group consisting of HLA-DR1, HLA-DR11, HLA-DR13, and HLA-DR15.

According to yet another aspect of the invention, compositions are provided. The compositions include an isolated antigen-presenting cell and an isolated immunogenic fragment of a polypeptide comprising the amino acid sequence set forth as SEQ ID NO:20. In some embodiments, the isolated antigen-presenting cell comprises an HLA-DR molecule. In some embodiments, the isolated immunogenic fragment is selected from the group consisting of: SEQ ID NO:32 and 72. In certain embodiments, the HLA-DR molecule is selected from the group consisting of HLA-DR1, HLA-DR11, HLA-DR13, and HLA-DR15. In some embodiments, the isolated antigen-presenting cell comprises an HLA-A2 molecule. In certain embodiments, the isolated immunogenic fragment is selected from the group consisting of SEQ ID NOs: 46, 50, 52, and 63.

According to another aspect of the invention, compositions are provided. The compositions include an isolated HLA class I-binding peptide and an isolated HLA class II-binding peptide, wherein the binding peptides are isolated immunogenic fragments of a polypeptide comprising the amino acid sequence set forth as SEQ ID NO:20. In some embodiments, the HLA class I-binding peptide and the HLA class II-binding peptide are combined as a polytope polypeptide. In certain embodiments, the HLA class I-binding peptide is an immunogenic fragment selected from the group consisting of SEQ ID NOs: 46, 50, 52, and 63. In some embodiments, the HLA class II-binding peptide is an immunogenic fragment selected from the group consisting of SEQ ID NOs:32 and 72.

According to another aspect of the invention, compositions are provided. The compositions include an isolated polypeptide comprising the amino acid sequence set forth as SEQ ID NO:20 and one or more isolated HLA class I-binding peptides. In some embodiments, the one or more isolated HLA class I-binding peptide is an immunogenic fragment selected from the group consisting of SEQ ID NOs: 46, 50, 52, and 63.

According to another aspect of the invention, compositions are provided. The compositions include an isolated polypeptide comprising the amino acid sequence set forth as SEQ ID NO:20 and one or more isolated HLA class II-binding peptides. In some embodiments, the one or more isolated HLA class II-binding peptide is an immunogenic fragment selected from the group consisting of SEQ ID NOs:32 and 72.

According to yet another aspect of the invention, compositions are provided. The compositions include an isolated polypeptide comprising the amino acid sequence set forth as SEQ ID NO:20 and one or more isolated HLA class II- and HLA class I-binding peptides. In some embodiments, the one or more isolated HLA class I-binding peptide is an immunogenic fragment selected from the group consisting of SEQ ID NOs: 46, 50, 52, and 63 and the one or more isolated HLA class II-binding peptide is an immunogenic fragment selected from the group consisting of SEQ ID NOs:32 and 72. In certain embodiments, one or more HLA class I-binding peptides and one or more of the HLA class II-binding peptide are combined as a polytope polypeptide.

According to another aspect of the invention, isolated antigen-presenting cells are provided. The isolated antigen-presenting cells include a complex of an HLA class I molecule and an HLA class I-binding polypeptide. In some embodiments, the HLA class I molecule is an HLA-A2 molecule. In certain embodiments, wherein the HLA class I-binding polypeptide is an immunogenic fragment selected from the group consisting of SEQ ID NOs: 46, 50, 52, and 63.

According to another aspect of the invention, isolated antigen-presenting cells are provided. The isolated antigen-presenting cells include a complex of an HLA class II molecule and an HLA class II-binding polypeptide. In some embodiments, the HLA class II molecule is an HLA-DR molecule. In certain embodiments, the HLA-DR molecule is selected from the group consisting of HLA-DR1, HLA-DR11, HLA-DR13, and HLA-DR15. In some embodiments, the HLA class II-binding polypeptide is selected from the group consisting of: SEQ ID NO:32 and 72.

According to yet another aspect of the invention, methods of inducing or enhancing an immune response in a subject are provided. The methods include administering to the subject an isolated nucleic acid molecule that encodes a polypeptide comprising the amino acid sequence set forth as SEQ ID NO:20, in an amount effective to induce or enhance the immune response in the subject. In some embodiments, the subject has or is suspected of having cancer. In certain embodiments, the cancer is colon cancer. In some embodiments, the isolated nucleic acid is in a plasmid. In certain embodiments, the isolated nucleic acid is in a virus. In some embodiments, the virus is vaccinia virus. In certain embodiments, the nucleic acid molecule is a plasmid. In some embodiments, the methods also include boosting the subject with recombinant virus that encodes a polypeptide comprising the amino acid sequence set forth as SEQ ID NO:20. In some embodiments, the virus is vaccinia virus.

According to another aspect of the invention, a recombinant virus is provided. The recombinant virus includes a nucleic acid molecule that encodes a polypeptide comprising the amino acid sequence set forth as SEQ ID NO:20. In some embodiments, the virus is vaccinia virus.

According to yet another aspect of the invention, methods of inducing or enhancing an immune response in a subject are provided. The methods include administering to the subject a nucleic acid molecule that encodes an immunogenic fragment of a polypeptide comprising the amino acid sequence set forth as SEQ ID NO:20, in an amount effective to induce or enhance the immune response in the subject. In some embodiments, the immunogenic fragment is a HLA class II binding peptide. In certain embodiments, the immunogenic fragment is selected from the group consisting of: SEQ ID NOs:31, 32, 33, 34, and 72. In certain embodiments, the immunogenic fragment is an HLA class I binding peptide. In some embodiments, the immunogenic fragment is selected from the group consisting of SEQ ID NOs: 46, 50, 52, and 63. In certain embodiments, the subject has or is suspected of having cancer. In some embodiments, the cancer is colon cancer. In some embodiments, the nucleic acid molecule is a plasmid. In certain embodiments the method also includes boosting the subject with recombinant virus that encodes an immunogenic fragment of a polypeptide comprising the amino acid sequence set forth as SEQ ID NO:20. In some embodiments, the virus is vaccinia virus.

According to another aspect of the invention, compositions are provided. The compositions include an isolated nucleic acid molecule that encodes an immunogenic fragment of a polypeptide comprising the amino acid sequence set forth as SEQ ID NO:20. In some embodiments, the compositions also include a pharmaceutically acceptable carrier. In certain embodiments, the compositions also include an adjuvant.

According to yet another aspect of the invention, recombinant viruses are provided. The recombinant viruses include an isolated nucleic acid molecule that encodes an immunogenic fragment of a polypeptide comprising the amino acid sequence set forth as SEQ ID NO:20 operably linked to a promoter. In some embodiments, the virus is vaccinia virus.

According to one aspect of the invention, methods for diagnosing colon cancer in a subject are provided. The methods include obtaining a biological sample from a subject, contacting the sample with at least two different colon cancer-associated polypeptides encoded by nucleic acid molecules comprising a nucleotide sequence selected from the group consisting of SEQ ID NOs:1-15, and determining specific binding between the colon cancer-associated polypeptides and agents in the sample, wherein the presence of specific binding is diagnostic for colon cancer in the subject.

According to another aspect of the invention, methods of determining onset, progression, or regression, of colon cancer in a subject are provided. The methods include obtaining from a subject a first biological sample, contacting the first sample with at least two different colon cancer-associated polypeptides encoded by nucleic acid molecules comprising a nucleotide sequence selected form the group consisting of SEQ ID NOs:1-15, determining specific binding between agents in the first sample and the at least two different colon cancer-associated polypeptides, obtaining from a subject a second biological sample, contacting the second biological sample with at least two different colon cancer-associated polypeptides encoded by nucleic acid molecules comprising a nucleotide sequence selected form the group consisting of SEQ ID NOs:1-15, determining specific binding between agents in the second sample and the at least two different colon cancer-associated polypeptides, and comparing the determination of binding in the first sample to the determination of specific binding in the second sample as a determination of the onset, progression, or regression of the colon cancer.

According to yet another aspect of the invention, methods for selecting a course of treatment of a subject having or suspected of having colon cancer is provided. The methods include obtaining from the subject a biological sample, contacting the sample with at least two different colon cancer-associated polypeptides encoded by nucleic acid molecules comprising a nucleotide sequence selected from the group consisting of SEQ ID NOs:1-15, determining specific binding between agents in the sample that are differentially expressed in different types of cancer, and the colon cancer-associated polypeptides, and selecting a course of treatment appropriate to the cancer of the subject. In some embodiments, the treatment is administering antibodies that specifically bind to the colon cancer-associated polypeptides. In some embodiments, the antibodies are labeled with one or more cytotoxic agents.

In some embodiments of the foregoing methods, the biological sample is a blood sample. In some embodiments, the agents are antibodies or antigen-binding fragments thereof. In some embodiments of the foregoing methods, the biological sample is contacted with at least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:15. In some embodiments of the foregoing methods, the biological sample is contacted with a colon cancer-associated polypeptide other than those encoded by nucleic acid molecules comprising a nucleotide sequence selected from the group consisting of SEQ ID NOs:1-15.

According to another aspect of the invention, methods for diagnosing colon cancer in a subject are provided. The methods include obtaining a biological sample from a subject, contacting the sample with antibodies or antigen-binding fragments thereof, that bind specifically to at least two different colon cancer-associated polypeptides encoded by nucleic acid molecules comprising a nucleotide sequence selected from the group consisting of SEQ ID NOs:1-15, and determining specific binding between the antibodies or antigen-binding fragments thereof and colon cancer-associated polypeptides in the sample, wherein the presence of specific binding is diagnostic for colon cancer in the subject.

According to another aspect of the invention, methods for determining onset, progression, or regression, of colon cancer in a subject are provided. The methods include, obtaining from a subject a first biological sample, contacting the first sample with antibodies or antigen-binding fragments thereof, that bind specifically to at least two different colon cancer-associated polypeptides encoded by nucleic acid molecules comprising a nucleotide sequence selected from the group consisting of SEQ ID NOs:1-15, determining specific binding between colon cancer-associated polypeptides in the first sample and the antibodies or antigen-binding fragments thereof, obtaining from a subject a second biological sample, contacting the second sample with antibodies or antigen-binding fragments thereof, that bind specifically to at least two different colon cancer-associated polypeptides encoded by nucleic acid molecules comprising a nucleotide sequence selected from the group consisting of SEQ ID NOs:1-15, determining specific binding between colon cancer-associated polypeptides in the second sample and the antibodies or antigen-binding fragments thereof, and comparing the determination of specific binding in the first sample to the determination of specific binding in the second sample as a determination of the onset, progression, or regression of colon cancer.

According to another aspect of the invention methods for selecting a course of treatment of a subject having or suspected of having colon cancer are provided. The methods include obtaining from the subject a biological sample, contacting the sample with antibodies or antigen-binding fragments thereof that bind specifically to at least two different colon cancer-associated polypeptides encoded by nucleic acid molecules comprising a nucleotide sequence selected from the group consisting of SEQ ID NOs:1-15, determining specific binding between colon cancer-associated polypeptides in the sample that are differentially expressed in different types of cancer, and the antibodies or antigen-binding fragments thereof, and selecting a course of treatment appropriate to the cancer of the subject. In some embodiments, the treatment is administering antibodies that specifically bind to the colon cancer-associated polypeptides. In some embodiments, the antibodies are labeled with one or more cytotoxic agents.

In some embodiments of the foregoing methods, the sample is selected from the group consisting of: tissue, stool, cells, blood, and mucus. In preferred embodiments of the foregoing methods, the tissue is colorectal tissue. In some embodiments of the foregoing methods, the antibodies are monoclonal or polyclonal antibodies, and in some embodiments, of the foregoing methods the antibodies are chimeric, human, or humanized antibodies. In some embodiments the antibodies are single chain antibodies, and in some embodiments of the foregoing methods, the antigen-binding fragments are F(ab')$_2$, Fab, Fd, or Fv fragments. In some embodiments of the foregoing methods, the biological sample is contacted with antibodies or antigen-binding fragments thereof, that bind specifically to at least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:1-15. In some embodiments of the foregoing methods, the biological sample is contacted with an antibody or antigen-binding fragment thereof, that binds specifically to a colon cancer-associated polypeptide other than those encoded by nucleic acid molecules comprising a nucleotide sequence selected from the group consisting of SEQ ID NOs: 1-15.

According to yet another aspect of the invention, kits for the diagnosis of colon cancer in a subject are provided. The kits include at least two different colon cancer-associated polypeptides encoded by nucleic acid molecules comprising a nucleotide sequence selected from the group consisting of: SEQ ID NOs: 1-15, one or more control antigens, and instructions for the use of the polypeptides in the diagnosis of colon cancer. In some embodiments, the colon cancer-associated polypeptides are bound to a substrate. In some embodiments, the one or more agents are antibodies or antigen-binding fragments thereof. In some embodiments, the kit includes at least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:1-15. In some embodiments, the kit further includes a colon cancer-associated polypeptide other than those encoded by a nucleic acid molecule comprising a nucleotide sequence selected from the group consisting of SEQ ID NOs:1-15.

According to yet another aspect of the invention, kits for the diagnosis of colon cancer in a subject are provided. The kits include antibodies or antigen-binding fragments thereof that bind specifically to at least two different colon cancer-associated polypeptides encoded by nucleic acid molecules comprising a nucleotide sequence selected from the group consisting of SEQ ID NOs:1-15, one or more control agents, and instructions for the use of the agents in the diagnosis of colon cancer. In some embodiments, the one or more agents are antibodies or antigen-binding fragments thereof. In some embodiments, the one or more agents are bound to a substrate. In some embodiments, the kit includes antibodies or antigen-binding fragments thereof, that bind specifically to at least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:1-15. In some embodiments, the kit further includes an antibody or antigen-binding fragment thereof, that binds specifically to a colon cancer-associated polypeptide other than those encoded by a nucleic acid molecule comprising a nucleotide sequence selected from the group consisting of SEQ ID NOs:1-15.

According to another aspect of the invention, protein microarrays are provided, which include at least two different colon cancer-associated polypeptides, wherein the colon cancer-associated polypeptides are encoded by nucleic acid molecules comprising a nucleotide sequence selected from the group consisting of: SEQ ID NOs: 1-15, fixed to a solid substrate. In some embodiments, the microarray comprises at least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:1-15. In some embodiments, the microarrays further consist essentially of a colon cancer-associated polypeptide other than those encoded by a nucleic acid molecule comprising a nucleotide sequence selected from the group consisting of SEQ ID NOs:1-15. In some embodiments, microarray further consists essential of at least one control polypeptide molecule.

According to yet another aspect of the invention, protein microarrays are provided, which include antibodies or antigen-binding fragments thereof, that specifically bind at least two different colon cancer-associated polypeptides encoded by nucleic acid molecules comprising a nucleotide sequence selected from the group consisting of: SEQ ID NOs:1-15, fixed to a solid substrate. In some embodiments, the protein microarray consists essentially of antibodies or antigen-binding fragments thereof, that bind specifically to least 3, 4, 5, 6, 7, 8, 9, 10, 11, 12, 13, 14, or 15 different colon cancer-associated polypeptides encoded by nucleic acid molecules comprising a nucleotide sequence selected from the group consisting of SEQ ID NOs:1-15. In some embodiments, the protein microarrays further consist essentially of an antibody or antigen-binding fragment thereof, that binds specifically to a colon cancer-associated polypeptide other than those encoded by a nucleic acid molecule comprising a nucleotide sequence selected from the group consisting of SEQ ID NOs: 1-15. In some embodiments, the protein microarrays further consist essentially of at least one control polypeptide molecule. In some embodiments, the antibodies are monoclonal or polyclonal antibodies. In some embodiments, the antibodies are chimeric, human, or humanized antibodies. In some embodiments, the antibodies are single chain antibodies, and in some embodiments, the antigen-binding fragments are F(ab')$_2$, Fab, Fd, or Fv fragments.

According to another aspect of the invention nucleic acid microarrays are provided. The nucleic acid microarrays include at least two nucleic acids selected from the group consisting of SEQ ID NOs:1-15, fixed to a solid substrate. In some embodiments, the microarray consists essentially of at least 3, 4, 5, 6, 7, 8, 9, 10, 11, 12, 13, 14, or 15 different nucleic acid molecules comprising a nucleotide sequence selected from the group consisting of SEQ ID NOs:1-15. In some embodiments, the microarray further consists essentially of a nucleic acid molecule other than those selected from the group consisting of SEQ ID NOs:1-15. In yet another embodiment, the microarrays further consist essentially of at least one control nucleic acid molecule.

According to another aspect of the invention, methods for diagnosing colon cancer in a subject are provided. The methods include obtaining from the subject a biological sample, and determining the expression of at least two colon cancer-associated nucleic acid molecules or expression products thereof in the sample, wherein the nucleic acid molecules comprise a nucleotide sequence selected from the group consisting of: SEQ ID NO: 1-15, wherein the expression is diagnosis of the colon cancer in the subject. In some embodiments, expression is determined for at least 3, 4, 5, 6, 7, 8, 9, 10, 11, 12, 13, 14, or 15 nucleic acid molecules comprising a nucleotide sequence selected from the group consisting of SEQ ID NOs:1-15. In some embodiments, the method includes determining expression of a colon cancer-associated nucleic acid molecule other than those comprising a nucleotide sequence selected from the group consisting of SEQ ID NOs:1-15. In some embodiments, the sample is selected from the group consisting of: tissue, stool, cells, blood, and mucus. In preferred embodiments, the tissue is colorectal tissue. In some embodiments, the expression of colon cancer-associated nucleic acid molecules is determined by a method selected from the group consisting of nucleic acid hybridization and nucleic acid amplification. In preferred embodiments, the hybridization is performed using a nucleic acid microarray.

According to yet another aspect of the invention, methods for determining onset, progression, or regression, of colon cancer in a subject are provided. The methods include obtaining from a subject a first biological sample, determining a level of expression of at least two colon cancer-associated nucleic acid molecules or expression products thereof in the first sample, wherein the nucleic acid molecules are selected from the group consisting of: SEQ ID NOs: 1-15, obtaining from the subject a second biological sample, determining a level of expression of at least two colon cancer-associated nucleic acid molecules or expression products thereof in the second sample, wherein the nucleic acid molecules are selected from the group consisting of: SEQ ID NOs: 1-15, and comparing the level of expression in the first sample to the level of expression in the second sample as a determination of the onset, progression, or regression of the colon cancer. In some embodiments, expression is determined for at least 3, 4, 5, 6, 7, 8, 9, 10, 11, 12, 13, 14, or 15 nucleic acid molecules selected from the group consisting of SEQ ID NOs:1-15. In some embodiments, the method further includes determining expression for a colon cancer-associated nucleic acid molecule other than those comprising a nucleotide sequence selected from the group consisting of SEQ ID NOs:1-15. In some embodiments, the sample is selected from the group consisting of: tissue, stool, cells, blood, and mucus. In preferred embodiments, the tissue is colorectal tissue. In some embodiments, the expression of colon cancer-associated nucleic acid molecules is determined by a method selected from the group consisting of nucleic acid hybridization and nucleic acid amplification. In preferred embodiments, the hybridization is performed using a nucleic acid microarray.

According to another aspect of the invention, methods for diagnosing cancer in a subject are provided. The methods include obtaining a biological sample from a subject, contacting the sample with a colon cancer-associated polypeptide encoded by a nucleic acid molecule comprising a nucleotide sequence selected from the group consisting of SEQ ID NOs: 1, 2, 5, and 6, and determining specific binding between the colon cancer-associated polypeptide and agents in the sample, wherein the presence of specific binding is diagnostic for cancer in the subject.

According to another aspect of the invention, methods for determining onset, progression, or regression, of cancer in a subject are provided. The methods include obtaining from a subject a first biological sample, contacting the first sample with a colon cancer associated polypeptide encoded by a nucleic acid molecule comprising a nucleotide sequence selected from the group consisting of SEQ ID NOs:1, 2, 5, and 6, determining specific binding between agents in the first sample and the colon cancer-associated, obtaining from a subject a second biological sample, contacting the second sample with a colon cancer associated polypeptide encoded by a nucleic acid molecule comprising a nucleotide sequence selected from the group consisting of SEQ ID NOs:1, 2, 5, and 6, determining specific binding between agents in the second sample and the colon cancer-associated polypeptide, and comparing the determination of binding in the first sample to the determination of specific binding in the second sample as a determination of the onset, progression, or regression of cancer.

According to another aspect of the invention, methods for selecting a course of treatment of a subject having or suspected of having cancer are provided. The methods include obtaining from the subject a biological sample, contacting the sample with a colon cancer-associated polypeptide encoded by a nucleic acid molecule comprising a nucleotide sequence selected from the group consisting of SEQ ID NOs:1, 2, 5, and 6, determining specific binding between agents in the sample that are differentially expressed in different types of cancer, and the colon cancer-associated polypeptide, and selecting a course of treatment appropriate to the cancer of the subject. In some embodiments, the treatment is administering antibodies that specifically bind to the colon cancer-associated polypeptide. In some embodiments, the antibodies are labeled with one or more cytotoxic agents.

In some embodiments of the foregoing methods, the sample is blood. In some embodiments of the foregoing methods, the agents are antibodies or antigen-binding fragments thereof. In preferred embodiments of the foregoing methods, the cancer is colon cancer.

According to another aspect of the invention, methods for diagnosing cancer in a subject are provided. The methods include obtaining a biological sample from a subject, contacting the sample with an antibody or antigen-binding fragment thereof, that binds specifically to a colon cancer-associated polypeptide encoded by a nucleic acid molecule comprising a nucleotide sequence selected from the group consisting of SEQ ID NOs:1, 2, 5, and 6, and determining specific binding between the antibody or antigen-binding fragment thereof and the colon cancer-associated polypeptide in the sample, wherein the presence of specific binding is diagnostic for cancer in the subject.

According to another aspect of the invention, methods for determining onset, progression, or regression, of cancer in a subject are provided. The methods include obtaining from a subject a first biological sample, contacting the first sample with antibodies or antigen-binding fragments thereof, that bind specifically to a colon cancer-associated polypeptides encoded by a nucleic acid molecule comprising a nucleotide sequence selected from the group consisting of SEQ ID NOs: 1, 2, 5, and 6, determining specific binding between colon cancer-associated polypeptides in the first sample and the antibodies or antigen-fragments thereof, obtaining from a subject a second biological sample, contacting the second sample with antibodies or antigen-binding fragments thereof, that bind specifically to a colon cancer-associated polypeptides encoded by a nucleic acid molecule comprising a nucleotide sequence selected from the group consisting of SEQ ID NOs:1, 2, 5, and 6, determining specific binding between colon cancer-associated polypeptides in the second sample and the antibodies or antigen-binding fragments thereof, and comparing the determination of specific binding in the first sample to the determination of specific binding in the second sample as a determination of the onset, progression, or regression of cancer.

According to another aspect of the invention, methods for selecting a course of treatment of a subject having or suspected of having cancer are provided. The methods include obtaining from the subject a biological sample, contacting the sample with antibodies or antigen-binding fragments thereof that bind specifically to a colon cancer-associated polypeptide encoded by a nucleic acid molecule comprising a nucleotide sequence selected from the group consisting of SEQ ID NOs:1, 2, 5, and 6, determining specific binding between colon cancer-associated polypeptides in the sample that are differentially expressed in different types of cancer, and the antibodies or antigen-binding fragments thereof, and selecting a course of treatment appropriate to the cancer of the subject. In some embodiments, the treatment is administering antibodies that specifically bind to the colon cancer-associated polypeptide. In some embodiments, the antibodies are labeled with one or more cytotoxic agents.

In some embodiments of the foregoing methods, the sample is selected from the group consisting of: tissue, stool, cells, blood, and mucus. In some embodiments of the foregoing methods, the tissue is colorectal tissue. In preferred embodiments of the foregoing methods, the antibodies are monoclonal or polyclonal antibodies, chimeric, human, or humanized antibodies. In some embodiments of the foregoing methods, the antibodies are single chain antibodies or antigen-binding fragments are F(ab')$_2$, Fab, Fd, or Fv fragments. In preferred embodiments of the foregoing methods, the cancer is colon cancer.

According to another aspect of the invention, kits for the diagnosis of cancer in a subject are provided. The kits include a colon cancer-associated polypeptide encoded by a nucleic acid molecule comprising a nucleotide sequence selected from the group consisting of: SEQ ID NOs: 1, 2, 5, and 6; one or more control antigens; and instructions for the use of the polypeptide and control antigens in the diagnosis of cancer. In some embodiments, the colon cancer-associated polypeptide is bound to a substrate. In some embodiments, the one or more agents are antibodies or antigen-binding fragments thereof. In preferred embodiments, the cancer is colon cancer.

According to another aspect of the invention, kits for the diagnosis of cancer in a subject, are provided. The kits include antibodies or antigen-binding fragments thereof that bind specifically to a colon cancer-associated polypeptide encoded by a nucleic acid molecule comprising a nucleotide sequence selected from the group consisting of SEQ ID NOs:1, 2, 5, and 6; one or more control agents; and instructions for the use of the antibodies, antigen-binding fragments, and agents in the diagnosis of cancer. In some embodiments, the one or more agents are antibodies or antigen-binding fragments thereof. In some embodiments, the one or more agents are bound to a substrate. In preferred embodiments, the cancer is colon cancer.

According to another aspect of the invention, protein microarrays are provided. The protein microarrays include a colon cancer-associated polypeptide, wherein the colon cancer-associated polypeptide is encoded by a nucleic acid molecule comprising a nucleotide sequence selected from the group consisting of: SEQ ID NOs: 1, 2, 5, and 6, fixed to a solid substrate. In some embodiments, the protein microarray further includes at least one control polypeptide molecule.

According to yet another aspect of the invention, protein microarrays are provided. The protein microarrays include antibodies or antigen-binding fragments thereof, that specifically bind a colon cancer-associated polypeptide encoded by a nucleic acid molecule comprising a nucleotide sequence selected from the group consisting of: SEQ ID NOs:1, 2, 5, and 6, fixed to a solid substrate. In some embodiments, the protein microarrays further include at least one control polypeptide molecule. In some embodiments, the antibodies are monoclonal or polyclonal antibodies. In some embodiments, the antibodies are chimeric, human, or humanized antibodies and in some embodiments, the antibodies are single chain antibodies. In some embodiments, the antigen-binding fragments are F(ab')$_2$, Fab, Fd, or Fv fragments.

According to another aspect of the invention, nucleic acid microarrays are provided. The nucleic acid microarrays include a nucleic acid selected from the group consisting of SEQ ID NOs: 1, 2, 5, and 6, fixed to a solid substrate. In some embodiments, the nucleic acid microarrays further include at least one control nucleic acid molecule.

According to yet another aspect of the invention, methods for diagnosing cancer in a subject are provided. The methods include obtaining from the subject a biological sample, and determining the expression of a colon cancer-associated nucleic acid molecule or expression product thereof in the sample, wherein the nucleic acid molecule comprises a nucleotide sequence selected from the group consisting of: SEQ ID NO: 1, 2, 5, and 6, wherein the expression is diagnostic of cancer in the subject. In some embodiments, the sample is selected from the group consisting of: tissue, stool, cells, blood, and mucus. In preferred embodiments, the tissue is colorectal tissue. In some embodiments, the expression of colon cancer-associated nucleic acid molecules is determined by a method selected from the group consisting of nucleic acid hybridization and nucleic acid amplification. In preferred embodiments, the hybridization is performed using a nucleic acid microarray. In preferred embodiments, the cancer is colon cancer.

According to another aspect of the invention, methods for determining onset, progression, or regression, of cancer in a subject are provided. The methods include obtaining from a subject a first biological sample, determining a level of expression of a colon cancer-associated nucleic acid molecule or expression products thereof in the first sample, wherein the nucleic acid molecule is selected from the group consisting of: SEQ ID NOs: 1, 2, 5, and 6, obtaining from the subject a second biological sample, determining a level of expression of a colon cancer-associated nucleic acid molecule or expression product thereof in the second sample, wherein the nucleic acid molecule is selected from the group consisting of: SEQ ID NOs: 1, 2, 5, and 6, and comparing the level of expression in the first sample to the level of expression in the second sample as a determination of the onset, progression, or regression of the cancer. In some embodiments, the sample is selected from the group consisting of: tissue, stool, cells, blood, and mucus. In preferred embodiments, the tissue is colorectal tissue. In some embodiments, the expression of colon cancer-associated nucleic acid molecules is determined by a method selected from the group consisting of nucleic acid hybridization and nucleic acid amplification. In some embodiments, the hybridization is performed using a nucleic acid microarray. In preferred embodiments, the cancer is colon cancer.

BRIEF DESCRIPTION OF THE DRAWINGS

FIG. 1 shows the results of the assay of Group 6, peptide 2 (SLLALKECI; SEQ ID NO:46). FIGS. 1A and 1B show results after two restimulations using Group 6 peptides. FIGS. 1C and 1D are the negative and positive controls, respectively, for the two-restimulation experiment. FIG. 1E shows results after three restimulations using Group 6 peptides. FIG. 1F shows results after three restimulations using peptide 6-2. FIG. 1G is the negative control for the three-restimulation experiment. Group 6 peptides=pool of 6 peptides including SLLALKECI (SEQ ID NO:46). The number in parenthesis is the number of spots per well.

FIG. 2 shows the results of the assay of Group 6 peptide 6 (LQARLFPGL; SEQ ID NO:50). FIGS. 2A and 2B show results after two restimulations using Group 6 peptides. FIGS. 2C and D are the negative and positive controls, respectively, for the two-stimulation experiment. FIG. 2E shows results after three restimulations using Group 6 peptides. FIGS. 2F and G show results after three restimulations using peptide 6-6. FIG. 2H is the negative control for the three-restimulation experiment. Group 6 peptides=pool of 6 peptides including LQARLFPGL (SEQ ID NO:50). The number in parenthesis is the number of spots per well.

FIG. 3 shows the results of the assay of Group 1 peptide 3 (NLEKSCVSV; SEQ ID NO:63). FIGS. 3A and 3B show results after two restimulations using Group 1 peptides. FIGS. 3C and 3D are the negative and positive controls, respectively, for the two-stimulation experiment. FIG. 3E shows results after three restimulations using Group 1 peptides. FIGS. 3F and G show results after three restimulations using peptide 1-3. FIG. 3H is the negative control for the three-restimulation experiment. Group 1 peptides=pool of 5 peptides including NLEKSCVSV (SEQ ID NO:63). The number in parenthesis is the number of spots per well.

DETAILED DESCRIPTION OF THE INVENTION

Figure 4A:
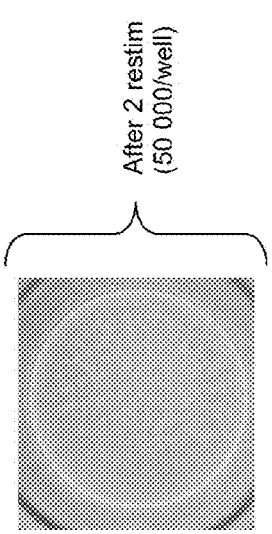
FIGS. 4A and 4B show results after two restimulations using Group 3 peptides.

The invention described herein relates to methods and compositions to induce and/or enhance an immune response in a subject. We have identified certain cancer-associated polypeptides and the encoding nucleic acid molecules thereof, as antigens that are useful to elicit immune responses. The identified antigenic polypeptides and/or their encoding nucleic acids can be utilized in methods and compositions that induce and/or enhance an immune response in a subject. The invention also includes kits that include the polypeptides and/or nucleic acids of the invention that induce and/or enhance an immune response. In some aspects of the invention, the polypeptide and/or nucleic acid molecules of the invention are useful to induce and/or enhance an immune response in a subject who has or is suspected of having cancer.

The invention described herein relates to the identification of polypeptides that elicit specific immune responses in subjects with cancer, particularly colon cancer, which is also known as large-bowel cancer and colorectal cancer. Colon cancer-associated polypeptides have been identified through SEREX screening of patients with cancer. The SEREX method (serological analysis of antigens by recombinant expression cloning), has been described by Sahin et al. (*Proc. Natl. Acad. Sci. USA* 92:11810-11813, 1995). The newly identified colon cancer-associated polypeptides and the encoding nucleic acid molecules thereof may be used as markers for cancer, including colon cancer, and may be used in the diagnosis and treatment assessment of colon cancer in humans. In addition, sets of at least two colon cancer-associated polypeptides and the encoding nucleic acid molecules thereof, may be used as markers in the diagnosis and treatment assessment of colon cancer in humans.

Polypeptides that elicit specific immune responses in colon cancer have now been identified and this identification allows use of these newly identified colon cancer-associated polypeptides or the encoding nucleic acids molecules thereof in cancer diagnostic assays and kits. In addition, sets of at least two of these new or previously identified polypeptides or the encoding nucleic acid molecules thereof, may be used in colon cancer diagnostic assays and kits. Such assays and kits are useful to detect colon cancer in human subjects, and for staging the progression, regression, or onset of colon cancer in subjects. The methods and kits described herein may also be used to evaluate treatments for colon cancer.

As used herein, "colon cancer-associated polypeptides" means polypeptides that elicit specific immune responses in animals having colon cancer and thus, include colon cancer-associated antigens and fragments of colon cancer-associated antigens, that are recognized by the immune system (e.g., by antibodies and/or T lymphocytes). The invention also relates to the use of the nucleic acid molecules that encode the colon cancer-associated polypeptides. In all embodiments, human colon cancer-associated polypeptides and the encoding nucleic acid molecules thereof, are preferred. As used herein, the "encoding nucleic acid molecules thereof" means the nucleic acid molecules that code for the polypeptides.

As used herein, a subject is preferably a human, non-human primate, cow, horse, pig, sheep, goat, dog, cat, or rodent. In all embodiments, human subjects are preferred. In some embodiments, the subject is suspected of having cancer and in preferred embodiments the subject is suspected of having colon cancer. In some embodiments the subject has been diagnosed with cancer, and in preferred embodiments the subject has been diagnosed with colon cancer.

As used herein, "different types" of cancer may include different histological types, cell types, different stages of cancer, (e.g., primary tumor or metastatic growth).

Methods for identifying subjects suspected of having colon cancer may include fecal occult blood examination, digital examination, CEA testing, endoscopic or radiographic techniques, biopsy, subject's family medical history, subject's medical history, or imaging technologies, such as magnetic resonance imaging (MRI). Such methods for identifying subjects suspected of having colon cancer are well-known to those of skill in the medical arts. As used herein, a biological sample includes, but is not limited to: tissue, body fluid (e.g. blood), bodily exudate, mucus, and stool specimen. The tissue may be obtained from a subject or may be grown in culture (e.g. from a cell line).

As used herein, a colorectal tissue sample is tissue obtained (e.g., from a colorectal tissue biopsy) using methods well-known to those of ordinary skill in the related medical arts. The phrase "suspected of being cancerous" as used herein means a colon cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Because of the variability of the cell types in diseased-tissue biopsy material, and the variability in sensitivity of the diagnostic methods used, the sample size required for analysis may range from 1, 10, 50, 100, 200, 300, 500, 1000, 5000, 10,000, to 50,000 or more cells. The appropriate sample size may be determined based on the cellular composition and condition of the biopsy and the standard preparative steps for this determination and subsequent isolation of the nucleic acid for use in the invention are well known to one of ordinary skill in the art. An example of this, although not intended to be limiting, is that in some instances a sample from the biopsy may be sufficient for assessment of RNA expression without amplification, but in other instances the lack of suitable cells in a small biopsy region may require use of RNA conversion and/or amplification methods or other methods to enhance resolution of the nucleic acid molecules. Such methods, which allow use of limited biopsy materials, are well known to those of ordinary skill in the art and include, but are not limited to: direct RNA amplification, reverse transcription of RNA to cDNA, amplification of cDNA, or the generation of radio-labeled nucleic acids.

In some embodiments, the colon cancer-associated nucleic acid molecules from the group of nucleic acid sequences numbered 1 through 15 in Table 3 (SEQ ID Nos: 1-15) and the colon cancer-associated polypeptides encoded by SEQ ID NOs: 1-15, are the group of polypeptide sequences SEQ ID NOs: 16 through 30 in Table 3. In some embodiments, colon cancer-associated polypeptides may include polypeptides other than those encoded by nucleic acid molecules comprising a nucleotide sequence selected from the group consisting of SEQ ID NOs:1-15.

The invention involves in some embodiments, diagnosing or monitoring colon cancer in subjects by determining the presence of an immune response to at least two colon cancer-associated polypeptides. In some embodiments, cancer, such as colon cancer, in subjects may be diagnosed or monitored by determining the presence of an immune response to one of the novel colon cancer-associated polypeptides described herein. In preferred embodiments, this determination is performed by assaying a bodily fluid obtained from the subject, preferably blood, for the presence of antibodies against at least two colon cancer-associated polypeptides or the nucleic acid molecules that encode the cancer-associated polypeptides, or for the presence of antibodies against one of the novel colon cancer-associated polypeptides or the encoding nucleic acid molecules thereof as described herein. This determination may also be performed by assaying a tissue of the subject for the presence of at least two colon cancer-associated polypeptides and/or the encoding nucleic acid molecules thereof, or assaying a tissue of the subject for the presence of one of the novel colon cancer-associated polypeptides or the encoding nucleic acid molecules thereof as described herein.

Measurement of the immune response against one of the novel colon cancer-associated polypeptides described herein, or at least two colon cancer-associated polypeptides in a subject over time by sequential determinations permits monitoring of the disease and/or the effects of a course of treatment. For example, a sample may be obtained from a subject, tested for an immune response to one of the novel colon cancer-associated polypeptides or may be tested for an immune response to at least two colon cancer-associated polypeptides and at a second, subsequent time, another sample may be obtained from the subject and similarly tested. The results of the first and second (subsequent) tests can be compared as a measure of the onset, regression or progression of colon cancer, or, if colon-cancer treatment was undertaken during the interval between obtaining the samples, the effectiveness of the treatment may be evaluated by comparing the results of the two tests.

The invention also involves in some embodiments diagnosing or monitoring colon cancer by determining the presence of at least two colon cancer-associated polypeptides and the encoding nucleic acid molecules thereof, or by determining the presence of one of the novel colon cancer-associated polypeptides and the encoding nucleic acid molecules thereof as described herein. In some important embodiments, this determination is performed by assaying a tissue sample from subject, preferably one believed to be cancerous, for the presence of at least two colon cancer-associated polypeptides or the encoding nucleic acid molecules thereof, or for the presence of one of the novel colon cancer-associated polypeptides and the encoding nucleic acid molecules thereof as described herein.

In other important embodiments, the presence of at least two colon cancer-associated polypeptides and the encoding nucleic acid molecules thereof, or the presence of one of the novel colon cancer-associated polypeptides and the encoding nucleic acid molecules thereof as described herein, are measured in mucus or fecal/stool samples. Such samples may contain colon cancer-associated polypeptides, or the encoding nucleic acids thereof, for example in shed cells. Measurement of the presence of at least two colon cancer-associated polypeptides and the encoding nucleic acid molecules thereof, or the presence of one of the novel colon cancer-associated polypeptides and the encoding nucleic acid molecules thereof as described herein, in subject's samples over time by sequential determinations at temporal intervals permits monitoring of the disease and/or the effects of a course of treatment.

In all embodiments, treatment for colon cancer may include, but is not limited to: surgical intervention, chemotherapy, radiotherapy, and adjuvant systemic therapies. In a preferred embodiment, treatment may include administering antibodies that specifically bind to the colon cancer-associated antigen. Optionally, an antibody can be linked to one or more detectable markers, antitumor agents or immunomodulators. Antitumor agents can include cytotoxic agents and agents that act on tumor neovasculature. Detectable markers include, for example, radioactive or fluorescent markers. Cytotoxic agents include cytotoxic radionuclides, chemical toxins and protein toxins.

The cytotoxic radionuclide or radiotherapeutic isotope may be an alpha-emitting isotope such as $^{225}$Ac, $^{211}$At, $^{212}$Bi, or $^{213}$Bi. Alternatively, the cytotoxic radionuclide may be a beta-emitting isotope such as $^{186}$Rh, $^{188}$Rh, $^{90}$Y, $^{131}$I or $^{67}$Cu. Further, the cytotoxic radionuclide may emit Auger and low energy electrons such as the isotopes $^{125}$I, $^{123}$I or $^{77}$Br.

Suitable chemical toxins or chemotherapeutic agents include members of the enediyne family of molecules, such as chalicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouaracil. Other chemotherapeutic agents are known to those skilled in the art.

Agents that act on the tumor neovasculature can include tubulin-binding agents such as combrestatin A4 (Griggs et al., Lancet Oncol. 2:82, 2001) and angiostatin and endostatin (reviewed in Rosen, Oncologist 5:20, 2000, incorporated by reference herein). Immunomodulators may also be conjugated to colon cancer-associated antibodies.

The invention thus involves in one aspect, colon cancer-associated polypeptides, genes encoding those polypeptides, functional modifications and variants of the foregoing, useful fragments of the foregoing, as well as diagnostics relating thereto, and diagnostic uses thereof. In some embodiments, the colon cancer-associated polypeptide genes correspond to SEQ ID NOs: 1-15. Encoded polypeptides (e.g., proteins), peptides and antisera thereto are also preferred for diagnosis and correspond to SEQ ID NOs: 16-30. In some embodiments, encoded polypeptides (e.g. proteins), peptides, and antisera thereto are ones other than those corresponding to SEQ ID NOs:16-30.

Some of the amino acid sequences identified by SEREX as colon cancer-associated polypeptides, and the nucleotide sequences encoding them, are newly identified and some are sequences deposited in databases such as GenBank. The use of the newly identified sequences in diagnostic assays for cancer is novel, as is the use of sets of at least two or more of the sequences in colon cancer diagnostic assays and kits.

Homologs and alleles of the colon cancer-associated polypeptide nucleic acids of the invention can be identified by conventional techniques. Thus, an aspect of the invention is those nucleic acid sequences that code for colon cancer-associated antigens and antigenic fragments thereof. As used herein, a homolog to a colon cancer-associated polypeptide is a polypeptide from a human or other animal that has a high degree of structural similarity to the identified colon cancer-associated polypeptides.

Identification of human and other organism homologs of colon cancer-associated polypeptides will be familiar to those of skill in the art. In general, nucleic acid hybridization is a suitable method for identification of homologous sequences of another species (e.g., human, cow, sheep), which correspond to a known sequence. Standard nucleic acid hybridization procedures can be used to identify related nucleic acid sequences of selected percent identity. For example, one can construct a library of cDNAs reverse transcribed from the mRNA of a selected tissue (e.g., colon) and use the nucleic acids that encode colon cancer-associated polypeptide identified herein to screen the library for related nucleotide sequences. The screening preferably is performed using high-stringency conditions to identify those sequences that are closely related by sequence identity. Nucleic acids so identified can be translated into polypeptides and the polypeptides can be tested for activity.

The term "high stringency" as used herein refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5× SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of colon cancer-associated polypeptide nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecule and sequencing.

In general homologs and alleles typically will share at least 75% nucleotide identity and/or at least 90% amino acid identity to the sequences of colon cancer-associated antigen, antigenic fragment thereof, and antigen precursor thereof nucleic acid and polypeptides, respectively, in some instances will share at least 90% nucleotide identity and/or at least 95% amino acid identity, and in other instances will share at least 95% nucleotide identity and/or at least 99% amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for colon cancer-associated polypeptide genes, a Southern blot may be performed using the foregoing conditions, together with a detectably labeled probe (e.g. radioactive or chemiluminescent probes). After washing the membrane to which the DNA is finally transferred, the membrane can be placed against X-ray film or a phosphorimager to detect the radioactive or chemiluminescent signal. In screening for the expression of colon cancer-associated polypeptide nucleic acids, Northern blot hybridizations using the foregoing conditions can be performed on samples taken from colon cancer patients or subjects suspected of having a condition characterized by abnormal cell proliferation or neoplasia of the colorectal tissues. Amplification protocols such as polymerase chain reaction using primers that hybridize to the sequences presented also can be used for detection of the colon cancer-associated polypeptide genes or expression thereof.

Identification of related sequences can also be achieved using polymerase chain reaction (PCR) and other amplification techniques suitable for cloning related nucleic acid sequences. Preferably, PCR primers are selected to amplify portions of a nucleic acid sequence believed to be conserved (e.g., a catalytic domain, a DNA-binding domain, etc.). Again, nucleic acids are preferably amplified from a tissue-specific library (e.g., colon). One also can use expression cloning utilizing the antisera described herein to identify nucleic acids that encode related antigenic proteins in humans or other species using the SEREX procedure to screen the appropriate expression libraries. (See: Sahin et al. *Proc. Natl. Acad. Sci. USA* 92:11810-11813, 1995).

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating colon cancer-associated polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as antigenicity, receptor binding, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also provides nucleic acid molecules that encode antigenic fragments of colon cancer-associated proteins.

Fragments, can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Fragments also can be used to produce fusion proteins for generating antibodies or determining binding of the polypeptide fragments, or for generating immunoassay components. Likewise, fragments can be employed to produce nonfused fragments of the colon cancer-associated polypeptides, useful, for example, in the preparation of antibodies, and in immunoassays. Preferred fragments are antigenic fragments, which are recognized by agents that specifically bind to colon cancer-associated polypeptides. As used herein, colon cancer-associated antibodies, are antibodies that specifically bind to colon cancer-associated polypeptides.

The invention also permits the construction of colon cancer-associated polypeptide gene "knock-outs" or "knock-ins" in cells and in animals, providing materials for studying certain aspects of colon cancer and immune system responses to colon cancer by regulating the expression of colon cancer-associated polypeptides. For example, a knock-in mouse may be constructed and examined for clinical parallels between the model and a colon cancer-infected mouse with upregulated expression of a colon cancer-associated polypeptide, which may be useful to trigger an immune reaction to the polypeptide. Such a cellular or animal model may also be useful for assessing treatment strategies for colon cancer.

Alternative types of animal models for colon cancer may be developed based on the invention. Stimulating an immune response to a colon cancer-associated polypeptide in an animal may provide a model in which to test treatments, and assess the etiology of colon cancers.

The invention also provides isolated polypeptides (including whole proteins and partial proteins) encoded by the foregoing colon cancer-associated nucleic acids. Such polypeptides are useful, for example, alone or as fusion proteins to generate antibodies, and as components of an immunoassay or diagnostic assay. Colon cancer-associated polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, such as colon cancer-associated antigen fragments including antigenic peptides also can be synthesized chemically using well-established methods of peptide synthesis.

Fragments of a polypeptide preferably are those fragments that retain a distinct functional capability of the polypeptide. Functional capabilities that can be retained in a fragment of a polypeptide include interaction with antibodies (e.g. antigenic fragments), interaction with other polypeptides or fragments thereof, selective binding of nucleic acids or proteins, and enzymatic activity. One important activity is the ability to provoke in a subject an immune response. As will be recognized by those skilled in the art, the size of the fragment will depend upon factors such as whether the epitope recognized by an antibody is a linear epitope or a conformational epitope. Thus, some antigenic fragments of colon cancer-associated polypeptides will consist of longer segments while others will consist of shorter segments, (e.g. 5, 6, 7, 8, 9, 10, 11 or 12 or more amino acids long, including each integer up to, but not including, the full length of the colon cancer-associated polypeptide). Those skilled in the art are well versed in methods for selecting antigenic fragments of proteins.

The skilled artisan will also realize that conservative amino acid substitutions may be made in colon cancer-associated polypeptides to provide functionally equivalent variants, or homologs of the foregoing polypeptides, i.e, the variants retain the functional capabilities of the colon cancer-associated antigen polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants or homologs of the colon cancer-associated polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

For example, upon determining that a peptide is a colon cancer-associated polypeptide, one can make conservative amino acid substitutions to the amino acid sequence of the peptide, and still have the polypeptide retain its specific antibody-binding characteristics and still retain the ability to induce an immune response in a subject.

Conservative amino-acid substitutions in the amino acid sequence of colon cancer-associated polypeptides to produce functionally equivalent variants of colon cancer-associated polypeptides typically are made by alteration of a nucleic acid encoding a colon cancer-associated polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a colon cancer-associated polypeptide. Where amino acid substitutions are made to a small unique fragment of a colon cancer-associated polypeptide, such as an antigenic epitope recognized by autologous or allogeneic sera or cytolytic T lymphocytes, the substitutions can be made by directly synthesizing the peptide. The activity of functionally equivalent fragments of colon cancer-associated polypeptides can be tested by cloning the gene encoding the altered colon cancer-associated polypeptide into a bacterial or mammalian expression vector, introducing the vector into an appropriate host cell, expressing the altered polypeptide, and testing for a functional capability of the colon cancer-associated polypeptides as disclosed herein. Peptides that are chemically synthesized can be tested directly for function, e.g., for binding to antisera recognizing associated antigens.

The invention as described herein has a number of uses, some of which are described elsewhere herein. First, the invention permits isolation of the colon cancer-associated protein molecules. A variety of methodologies well-known to the skilled practitioner can be utilized to obtain isolated colon cancer-associated polypeptide molecules. The polypeptide may be purified from cells that naturally produce the polypeptide, by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating colon cancer-associated polypeptides. These include, but are not limited to, immunochromatography, HPLC, size-exclusion chromatography, ion-exchange chromatography, and immune-affinity chromatography.

The isolation and identification of colon cancer-associated polypeptides also permits the artisan to diagnose a disorder characterized by expression of colon cancer-associated polypeptides, and characterized preferably by an immune response against the colon cancer-associated polypeptides.

The methods related to colon cancer-associated polypeptide immune responses involve determining the immune response (antibody or cellular) against one or more colon cancer-associated polypeptides. The immune response can be assayed by any of the various immunoassay methodologies known to one of ordinary skill in the art. For example, the antigenic colon cancer-associated polypeptides can be used as a target to capture antibodies from a blood sample drawn from a patient in an ELISA assay.

The methods related to colon cancer-associated polypeptide expression involve determining expression of one or more colon cancer-associated nucleic acids, and/or encoded colon cancer-associated polypeptides and/or peptides derived therefrom and comparing the expression with that in a colon cancer-free subject. Such determinations can be carried out via any standard nucleic acid determination assay, including the polymerase chain reaction, or assaying with labeled hybridization probes. Such hybridization methods include, but are not limited to microarray techniques.

The invention also makes it possible to isolate proteins that specifically bind to colon cancer-associated antigens as disclosed herein, including antibodies and cellular binding partners of the colon cancer-associated polypeptides. Additional uses are described further herein.

The invention also involves agents such as polypeptides that bind to colon cancer-associated polypeptides. Such binding agents can be used, for example, in screening assays to detect the presence or absence of colon cancer-associated polypeptides and complexes of colon cancer-associated polypeptides and their binding partners and in purification protocols to isolate colon cancer-associated polypeptides and complexes of colon cancer-associated polypeptides and their binding partners. Such agents also may be used to inhibit the native activity of the colon cancer-associated polypeptides, for example, by binding to such polypeptides.

The invention, therefore, embraces peptide binding agents which, for example, can be antibodies or fragments of antibodies having the ability to selectively bind to colon cancer-associated polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to colon cancer-associated polypeptides, and complexes of both colon cancer-associated polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the colon cancer-associated polypeptide. This process can be repeated through several cycles of reselection of phage that bind to the colon cancer-associated polypeptide. Repeated rounds lead to enrichment of phage bearing particular sequences. DNA sequence analysis can be conducted to identify the sequences of the expressed polypeptides. The minimal linear portion of the sequence that binds to the colon cancer-associated polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the colon cancer-associated polypeptides.

Thus, the colon cancer-associated polypeptides of the invention, including fragments thereof, can be used to screen peptide libraries, including phage display libraries, to identify and select peptide binding partners of the colon cancer-associated polypeptides of the invention. Such molecules can be used, as described, for screening assays, for purification protocols, for interfering directly with the functioning of colon cancer-associated polypeptides and for other purposes that will be apparent to those of ordinary skill in the art. For example, isolated colon cancer-associated polypeptides can be attached to a substrate (e.g., chromatographic media, such as polystyrene beads, or a filter), and then a solution suspected of containing the binding partner may be applied to the substrate. If a binding partner that can interact with colon cancer-associated polypeptides is present in the solution, then it will bind to the substrate-bound colon cancer-associated polypeptide. The binding partner then may be isolated.

As detailed herein, the foregoing antibodies and other binding molecules may be used for example, to identify tissues expressing protein or to purify protein. Antibodies also may be coupled to specific diagnostic labeling agents for imaging of cells and tissues that express colon cancer-associated polypeptides or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m, iodine-131 and indium-1, nuclides for nuclear magnetic resonance such as fluorine and gadolinium.

The invention also includes methods to monitor the onset, progression, or regression of colon cancer in a subject by, for example, obtaining samples at sequential times from a subject and assaying such samples for the presence and/or absence of an antigenic response that is a marker of the condition. A subject may be suspected of having colon cancer or may be believed not to have colon cancer and in the latter case, the sample may serve as a normal baseline level for comparison with subsequent samples.

Onset of a condition is the initiation of the changes associated with the condition in a subject. Such changes may be evidenced by physiological symptoms, or may be clinically asymptomatic. For example, the onset of colon cancer may be followed by a period during which there may be colon cancer-associated physiological changes in the subject, even though clinical symptoms may not be evident at that time. The progression of a condition follows onset and is the advancement of the physiological elements of the condition, which may or may not be marked by an increase in clinical symptoms. In contrast, the regression of a condition is a decrease in physiological characteristics of the condition, perhaps with a parallel reduction in symptoms, and may result from a treatment or may be a natural reversal in the condition.

A marker for colon cancer may be the specific binding of a colon cancer-associated polypeptide with an antibody. Onset of a colon cancer condition may be indicated by the appearance of such a marker(s) in a subject's samples where there was no such marker(s) determined previously. For example, if marker(s) for colon cancer are determined not to be present in a first sample from a subject, and colon cancer marker(s) are determined to be present in a second or subsequent sample from the subject, it may indicate the onset of cancer.

Progression and regression of a colon cancer condition may be generally indicated by the increase or decrease, respectively, of marker(s) in a subject's samples over time. For example, if marker(s) for colon cancer are determined to be present in a first sample from a subject and additional marker(s) or more of the initial marker(s) for colon cancer are determined to be present in a second or subsequent sample from the subject, it may indicate the progression of cancer. Regression of cancer may be indicated by finding that marker(s) determined to be present in a sample from a subject are not determined to be found, or found at lower amounts in a second or subsequent sample from the subject.

The progression and regression of a colon cancer condition may also be indicated based on characteristics of the colon cancer-associated polypeptides determined in the subject. For example, some colon cancer-associated polypeptides may be abnormally expressed at specific stages of colon cancer (e.g. early-stage colon cancer-associated polypeptides; mid-stage colon cancer-associated polypeptides; and late-stage colon cancer-associated polypeptides). Another example, although not intended to be limiting, is that colon cancer-associated polypeptides may be differentially expressed in primary tumors versus metastases, thereby allowing the stage and/or diagnostic level of the disease to be established, based on the identification of selected colon cancer-associated polypeptides in a subject sample.

Another method of staging colon cancer may be based on variation in a subject's immune response to colon cancer-associated polypeptides, which may or may not be abnormally expressed in the subject. Variability in the immune response to the polypeptides may be used to indicate the stage of colon cancer in a subject, for example, some colon cancer-associated polypeptides may trigger an immune response at different stages of the colon cancer than that triggered by other colon cancer-associated polypeptides.

Different types of colon cancer, such as familial adenomatous polyposis (FAP) or hereditary nonpolyposis colon cancer (HNPCC), also known as Lynch syndrome, may express different colon cancer-associated polypeptides and the encoding nucleic acid molecules thereof, or may have different spatial or temporal expression patterns. Such variations may allow cancer-specific diagnosis and subsequent treatment tailored to the patient's specific condition. These colon cancer-specific diagnoses may also be based on the variations in immune responses to the different colon cancer-associated polypeptides.

The invention includes kits for assaying the presence of colon cancer-associated polypeptides and/or antibodies that specifically bind to colon cancer-associated polypeptides. An example of such a kit may include the above-mentioned polypeptides bound to a substrate, for example a dipstick, which is dipped into a blood or body fluid sample of a subject. The surface of the substrate may then be processed using procedures well known to those of skill in the art, to assess whether specific binding occurred between the polypeptides and agents (e.g. antibodies) in the subject's sample. For example, procedures may include, but are not limited to, contact with a secondary antibody, or other method that indicates the presence of specific binding.

Another example of a kit may include an antibody or antigen-binding fragment thereof, that binds specifically to a colon cancer-associated polypeptide. The antibody or antigen-binding fragment thereof, may be applied to a tissue sample from a patient with colon cancer and the sample then processed to assess whether specific binding occurs between the antibody and a polypeptide or other component of the sample. In addition, the antibody or antigen-binding fragment thereof, may be applied to a stool sample from a subject, either suspected of having colon cancer, diagnosed with colon cancer, or believed to be free of colon cancer. As will be understood by one of skill in the art, such binding assays may also be performed with a sample or object contacted with an antibody and/or colon cancer-associated polypeptide that is in solution, for example in a 96-well plate or applied directly to an object surface.

The foregoing kits can include instructions or other printed material on how to use the various components of the kits for diagnostic purposes.

The invention also relates, in part, to the use of colon cancer-associated polypeptides of the invention to induce an immune response in a subject. Colon cancer-associated polypeptides, fragments thereof, and their respective encoding nucleic acids that are identified herein may be used in the disclosed methods and compositions for inducing an immune response in a subject. For example, one cancer-associated peptides of the invention, identified herein as NY-CO-58 (Kinesin-like 6, KNSL6) and fragments of the polypeptide can be used in the methods and compositions of the invention that related to inducing an immune response in a subject.

The nucleic acid that encodes the full-length NY-CO-58 polypeptide and the full-length NY-CO-58 polypeptide are disclosed herein as SEQ ID NO:5 and SEQ ID NO:20 respectively. In addition to the use of full-length NY-CO-58 polypeptide and nucleic acids to induce an immune response, the invention also includes methods of inducing an immune response in a subject with the administration of immunogenic fragments of the full-length NY-CO-58 polypeptide and nucleic acid molecules.

As used herein, the term "fragment" means a portion of a polypeptide or nucleic acid molecule that has an amino acid or nucleotide sequence that corresponds to the sequence of the full-length polypeptide or nucleic acid, respectively, but is shorter in length than the full-length molecule. Thus, a fragment of the polypeptide comprising the amino acid sequence set forth as SEQ ID NO:20, would correspond to a portion of the amino acid sequence of SEQ ID NO:20 that is one or more residues shorter than the full-length polypeptide set forth as SEQ ID NO:20. Some fragments of a polypeptide consist of longer segments (e.g. 20, 30, 40, 50, 60, 70, 80, 90, 100 or more amino acids long), while others consist of shorter segments, (e.g. 5, 6, 7, 8, 9, 10, 11 or 12 or more amino acids long). A "fragment" means a polypeptide that may include each integer up to, but not including, the full length of the "original" (e.g. full-length) polypeptide.

In some embodiments of the invention, a polypeptide fragment is an immunogenic (or antigenic) fragment. As used herein, an immunogenic or antigenic fragment is a polypeptide that when administered to a subject induces an immune response. An immunogenic fragment of the polypeptide set forth as SEQ ID NO:20, would be a portion of the polypeptide set forth as SEQ ID NO:20 that includes 724 or fewer amino acids that correspond to a portion of the amino acid sequence of SEQ ID NO:20 and that can induce an immune response when administered to a subject. Examples of immunogenic fragments of the polypeptide set forth as SEQ ID NO:20 are provided herein and include, but are not limited to: SEQ ID NOs:31, 32, 33, 34, 72, 46, 50, 52, and 63.

The examples below show the isolation of immunogenic fragments of the polypeptide set forth as SEQ ID NO:20 and the use of the full-length SEQ ID NO:20 and immunogenic fragments thereof, to induce an immune response in a subject. The immunogenic fragments of the invention include peptides that are HLA class I-binding peptides and peptides that are HLA class II-binding peptides. Examples of such fragments include SEQ ID NOs:32 and 72, which are HLA class II-binding fragments and SEQ ID NOs:46, 50, 52, and 63, which are HLA class I-binding fragments.

Additional NY-CO-58 polypeptide fragments that are useful in the methods and compositions of the invention are fragments that are at least eight amino acids in length. These fragments include between 8 and 29 amino acids of one of the polypeptide sequences set forth as SEQ ID NO:31, 33, 34, 35, 36, 37, 38, 39, and 40. Thus, in some aspects of the invention, a fragment is a polypeptide that corresponds to an amino acid sequence of SEQ ID NOs:31, 33, 34, 35, 36, 37, 38, 39, or 40 that has a total of 1, 2, 3, 4, 5, 6, 7, 8, 9, 10, 11, 12, 13, 14, 15, 16, 17, 18, 19, 20, 21, or 22 amino acids removed from the N-terminal and/or the C-terminal end of the sequence—yielding a polypeptide that is from 8 to 29 amino acids in length. The polypeptide LAIKIQRSNGLI (SEQ ID NO:32) is an example of a fragment of SEQ ID NO:31 that corresponds to the amino acid sequence of SEQ ID NO:31 minus 12 amino acids from the N-terminal end and minus 6 amino acids from the C-terminal end of SEQ ID NO:31. In some embodiments, a polypeptide fragment is a class II binding peptide. The class I or class II binding property of a NY-CO-58 polypeptide fragment can be assessed using standard methods and assays provided herein. One of ordinary skill in the art will recognize the polypeptide fragments of SEQ ID NOs:31, 33, 34, 35, 36, 37, 38, 39, or 40 based on the foregoing description.

The HLA class I and class II molecules are structurally distinct but homologous proteins. Class I molecules present peptides to and are recognized by CD8$^+$ T cells, and class II molecules present peptides to CD4$^+$ T cells. It is known in the art that HLA class I molecules can accommodate peptides that are about 8 to 11 amino acid residues long. It is also well known in the art that HLA class II peptide length is variable between about 10 amino acids and about 30 amino acids (Engelhard, *Ann. Rev. Immunol.* 12:181-201, 1994). Most of the HLA class II binding peptides fall in to the length range of 12-19 amino acids. Nested sets of HLA class II binding peptides have been identified, wherein the peptides share a core sequence but have different amino acids at amino and/or carboxyl terminal ends (see, e.g., Chicz et al., *J. Exp. Med.* 178:27-47, 1993). Thus additional HLA class I binding peptides and HLA class II binding peptides that are immunogenic fragments of the polypeptide designated as NY-CO-58 polypeptide (SEQ ID NO:20), can be identified by one of ordinary skill in the art according to the procedures described herein.

The procedures described in the Examples can be utilized to identify NY-CO-58 family HLA class I and II binding peptides. Thus, for example to identify additional HLA class II binding peptides, one can load antigen presenting cells, such as dendritic cells of normal blood donors, with a recombinant NY-CO-58 protein (or a fragment thereof) by contacting the cells with the NY-CO-58 polypeptide or by introducing into the cells a nucleic acid molecule which directs the expression of the NY-CO-58 protein of interest (or fragment thereof containing the HLA class II binding peptide). The antigen-presenting cells then can be used to induce in vitro the activation and proliferation of specific CD4 lymphocytes which recognize NY-CO-58 HLA class II binding peptides. The sequence of the peptides then can be determined as described in the Examples, e.g., by stimulating cells with peptide fragments of the NY-CO-58 protein used to stimulate the activation and proliferation of CD4 lymphocytes. Alternatively, one can load antigen presenting cells with peptides derived from a NY-CO-58 protein. For example, one can make predictions of peptide sequences derived from NY-CO-58 family proteins which are candidate HLA class II binding peptides based on the similarity with the peptide sequences identified herein, and/or based on the consensus amino acid sequences for binding HLA class II molecules. In this regard, see, e.g. International applications PCT/US96/03182 and PCT/US98/01373. Peptides which are thus selected can be used in the assays described herein for inducing specific CD4 lymphocytes and identification of peptides. Additional methods of selecting and testing peptides for HLA class II binding are well known in the art.

Similarly, routine methods of identifying HLA class I binding peptides are known in the art. Assays described herein can be used for inducing CD8 T cells, and additional HLA class I binding peptides can be identified.

As noted above, the invention embraces functional variants of NY-CO-58 HLA class I and class II binding peptides. As used herein, a "functional variant" or "variant" of an HLA class I or class II binding peptide is a peptide that contains one or more modifications (generally 5 or fewer) to the primary amino acid sequence of a HLA class I or class II binding peptide and retains the HLA class I or class II and T cell receptor binding properties disclosed herein. Modifications that create a NY-CO-58 HLA class I or class II binding peptide functional variant can be made, for example to: 1) enhance a property of a NY-CO-58 HLA class I or class II binding peptide, such as peptide stability in an expression system or the stability of protein-protein binding such as HLA-peptide binding; 2) to provide a novel activity or property to a NY-CO-58 HLA class I or class II binding peptide, such as addition of an antigenic epitope or addition of a detectable moiety; or 3) to provide a different amino acid sequence that produces the same or similar T cell stimulatory properties. Modifications to NY-CO-58 HLA class I or class II binding peptides can be made to nucleic acids which encode the peptides, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like. Variants also can be selected from libraries of peptides, which can be random peptides or peptides based on the sequence of the NY-CO-58 peptides (including fragments thereof) including substitutions at one or more positions. Some suitable sequences for preparation of peptide libraries are provided in the Examples below. For example, a peptide library can be used in competition assays with complexes of NY-CO-58 peptides bound to HLA class II molecules (e.g. dendritic cells loaded with NY-CO-58 peptide) and with complexes of NY-CO-58 peptides bound to HLA class I molecules. Peptides which compete for binding of the NY-CO-58 peptide to the HLA class I or class II molecule can be sequenced and used in other assays (e.g., CD8 lymphocyte proliferation, CD4 lymphocyte proliferation) to determine suitability as NY-CO-58 peptide and NY-CO-58 fragment functional variants.

The amino acid sequence of NY-CO-58 HLA class I or class II binding peptides may be of natural or non-natural origin, that is, they may comprise a natural NY-CO-58 HLA class I or class II binding peptide molecule or may comprise a modified sequence as long as the amino acid sequence retains the ability to stimulate helper T cells when presented (i.e., bound to an appropriate HLA class I or class II molecule on the cell surface) and retains the property of binding to an HLA class I or class II molecule such as an HLA-A2 or HLA DR molecule, respectively. Such modified peptides that retain the ability to bind HLA class II molecules and stimulate helper T cells and modified peptides that retain the ability to bind HLA class I molecules and stimulate T cells are "functional variants" as used herein. For example, NY-CO-58 HLA class I and class II binding peptides in this context may be fusion proteins including a NY-CO-58 HLA class I or class II binding peptide and unrelated amino acid sequences, synthetic NY-CO-58 HLA class I or class II binding peptides, labeled peptides, peptides isolated from patients with a NY-CO-58 protein-expressing cancer (e.g. colon cancer), peptides isolated from cultured cells which express one or more NY-CO-58 proteins, and peptides coupled to nonpeptide molecules (for example in certain drug delivery systems).

Preferably, the NY-CO-58 HLA class I and class II binding peptides are non-hydrolyzable. To provide such peptides, one may select NY-CO-58 HLA class I and class II binding peptides from a library of non-hydrolyzable peptides, such as peptides containing one or more D-amino acids or peptides containing one or more non-hydrolyzable peptide bonds linking amino acids. Alternatively, one can select peptides which are optimal for inducing $CD4^+$ T lymphocytes or $CD8^+$ T cells and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a NY-CO-58 HLA class I or class II binding peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include, but are not limited to, -psi[$CH_2NH$]— reduced amide peptide bonds, -psi[$COCH_2$]— ketomethylene peptide bonds, -psi[CH(CN)NH]— (cyanomethylene)amino peptide bonds, -psi[$CH_2CH(OH)$]— hydroxyethylene peptide bonds, -psi[$CH_2O$]— peptide bonds, and -psi[$CH_2S$]— thiomethylene peptide bonds.

Nonpeptide analogs of peptides, e.g., those which provide a stabilized structure or lessened biodegradation, are also provided in accordance with the invention. Peptide mimetic analogs can be prepared based on a selected NY-CO-58 HLA class I or class II binding peptide by replacement of one or more residues by nonpeptide moieties. Preferably, the nonpeptide moieties permit the peptide to retain its natural conformation, or stabilize a preferred, e.g., bioactive, confirmation. Such peptides can be tested in molecular or cell-based binding assays to assess the effect of the substitution(s) on conformation and/or activity. One example of methods for preparation of nonpeptide mimetic analogs from peptides is described in Nachman et al., *Regul. Pept.* 57:359-370 (1995). Peptide as used herein embraces all of the foregoing.

If a variant involves a change to an amino acid sequence of the invention, such as SEQ ID NO:20, SEQ ID NO:31, SEQ ID NO:32, SEQ ID NO:33, SEQ ID NO:34, SEQ ID NO:72, SEQ ID NO:46, SEQ ID NO:50, SEQ ID NO:52, and SEQ ID NO:63, functional variants of the NY-CO-58 HLA class I and class II binding peptide having conservative amino acid substitutions typically will be preferred, i.e., substitutions which retain a property of the original amino acid such as charge, hydrophobicity, conformation, ability to induce an immune response. Examples of conservative substitutions are provided above herein.

Additional methods for identifying functional variants of the NY-CO-58 HLA class I and class II binding peptides are known in the art. For example, the published PCT application of Strominger and Wucherpfennig (PCT/US96/03182) provides methods for identifying functional variants of HLA class II binding peptides. These methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine. These and other art-known methods may be employed to identify functional variants of NY-CO-58 HLA class I and class II binding peptides.

Other computational methods for selecting amino acid substitutions, such as iterative computer structural modeling, can also be performed by one of ordinary skill in the art to prepare variants. Sequence motifs for NY-CO-58 HLA class I binding peptide functional variants can be developed by analysis of the binding domains or binding pockets of major histocompatibility complex HLA-A2 proteins and/or the T cell receptor ("TCR") contact points of the NY-CO-58 HLA class I binding peptides disclosed herein. By providing a detailed structural analysis of the residues involved in forming the HLA class I binding pockets, one is enabled to make predictions of sequence motifs for binding of NY-CO-58 peptides to any of the HLA class I proteins. Similarly, sequence motifs for NY-CO-58 HLA class II binding peptide functional variants can be developed by analysis of the binding domains or binding pockets of major histocompatibility complex HLA-DR proteins and/or the T cell receptor ("TCR") contact points of the NY-CO-58 HLA class II binding peptides disclosed herein. By providing a detailed structural analysis of the residues involved in forming the HLA class II binding pockets, one is enabled to make predictions of sequence motifs for binding of NY-CO-58 peptides to any of the HLA class II proteins.

Using these sequence motifs as search, evaluation, or design criteria, one is enabled to identify classes of peptides (e.g. NY-CO-58 HLA class I or class II binding peptides, particularly the NY-CO-58 peptides disclosed herein, and functional variants thereof) that have a reasonable likelihood of binding to a particular HLA molecule and of interacting with a T cell receptor to induce T cell response. These peptides can be synthesized and tested for activity as described herein. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of disease.

The Strominger and Wucherpfennig PCT application, and references cited therein, all of which are incorporated by reference in their entirety, describe the HLA class II and TCR binding pockets which contact residues of an HLA class II peptide. By keeping the residues which are likely to bind in the HLA class II and/or TCR binding pockets constant or permitting only specified substitutions, functional variants of NY-CO-58 HLA class II binding peptides can be prepared which retain binding to HLA class II and T cell receptor.

Similar strategies are useful to identify and prepare NY-CO-58 HLA class I and class II binding peptides for use in the methods of the invention.

Thus methods for identifying additional NY-CO-58 family HLA class I and class II peptides, in particular NY-CO-58 HLA class I and class II binding peptides, and functional variants thereof, are provided. In general, any NY-CO-58 protein can be subjected to the analysis noted above, peptide sequences selected and the tested as described herein. With respect to NY-CO-58 full-length and immunogenic fragments disclosed herein, for example, the methods include selecting a NY-CO-58 HLA class I or class II binding peptide, an HLA class I or class II binding molecule that binds the NY-CO-58 HLA class I or class II binding peptide, respectively, and a T cell that is stimulated by the NY-CO-58 HLA class I or class II binding peptide presented by the HLA class I or class II binding molecule, respectively. In some embodiments, the NY-CO-58 HLA class I binding peptide comprises the amino acid sequence of SEQ ID NO: 46, SEQ ID NO:50, SEQ ID NO:52, or SEQ ID NO:63. In some embodiments, the NY-CO-58 HLA class II binding peptide comprises the amino acid sequence of SEQ ID NO:31, SEQ ID NO:32, SEQ ID NO:33, SEQ ID NO:34, or SEQ ID NO:72. In some embodiments, the peptide consists of those amino acid sequences. A first amino acid residue of the NY-CO-58 HLA class I or class II binding peptide may be mutated to prepare a variant peptide. The amino acid residue can be mutated according to the principles of HLA and T cell receptor contact points set forth in the Strominger and Wucherpfennig PCT application described above. Any method for preparing variant peptides can be employed, such as synthesis of the variant peptide, recombinantly producing the variant peptide using a mutated nucleic acid molecule, and the like.

The binding of the variant peptide to HLA class I and class II binding molecules and stimulation of the T cell are then determined according to standard procedures. For example, as exemplified below, the variant peptide can be contacted with an antigen presenting cell which contains the HLA class I or class II molecule that binds the NY-CO-58 peptide to form a complex of the variant peptide and antigen presenting cell. This complex can then be contacted with a T cell which recognizes the NY-CO-58 HLA class I or class II binding peptide presented by the HLA class I or class II binding molecule, respectively. T cells can be obtained from a patient having a condition characterized by expression of NY-CO-58 proteins or nucleic acids, such as cancer. In some embodiments, the cancer is colon cancer. Recognition of variant peptides by the T cells can be determined by measuring an indicator of T cell stimulation such as TNF or IFNγ production. Similar procedures can be carried out for identification and characterization of other NY-CO-58 family HLA class I or class II binding peptides. T cells, and other cells that have similar binding properties, also can be made using the cloned T cell receptors described herein, in accordance with standard transfection or transduction procedures.

Binding of a variant peptide to the HLA class I or class II binding molecule and stimulation of the T cell by the variant peptide presented by the HLA class I or class II binding molecule, respectively, indicates that the variant peptide is a functional variant. The methods also can include the step of comparing the stimulation of the T cell by the NY-CO-58 HLA class I or class II binding peptide and the stimulation of the T cell by the functional variant as a determination of the effectiveness of the stimulation of the T cell by the functional variant. By comparing the functional variant with the NY-CO-58 HLA class I or class II binding peptide, peptides with increased T cell stimulatory properties can be prepared.

The foregoing methods can be repeated sequentially with, for example, a second, third, fourth, fifth, sixth, seventh, eighth, ninth, and tenth substitutions to prepare additional functional variants of the disclosed NY-CO-58 HLA class I and class II binding peptides. Variants of the NY-CO-58 HLA class I and class II binding peptides prepared by any of the foregoing methods can be sequenced, if necessary, to determine the amino acid sequence and thus deduce the nucleotide sequence which encodes such variants.

Also a part of the invention are those nucleic acid sequences which code for NY-CO-58 HLA class I or class II binding peptides or variants thereof and other nucleic acid sequences which hybridize to a nucleic acid molecule consisting of the above-described nucleotide sequences, under high stringency conditions (see above herein). Preferred nucleic acid molecules include those comprising the nucleotide sequences that encode HLA class I binding peptides comprising the amino acid sequence of SEQ ID NO: 46, SEQ ID NO:50, SEQ ID NO:52, or SEQ ID NO:63. Preferred nucleic acid molecules include those comprising the nucleotide sequences that encode HLA class II binding peptides comprising the amino acid sequence SEQ ID NO:31, SEQ ID NO:32, SEQ ID NO:33, SEQ ID NO:34, or SEQ ID NO:72. Methods of identifying related nucleic acid sequences, including sequences of selected percent identity are provided above herein.

It will also be understood that the invention embraces the use of the sequences in expression vectors, as well as to transfect host cells and cell lines, be these prokaryotic (e.g., *E. coli*), or eukaryotic (e.g., dendritic cells, CHO cells, COS cells, yeast expression systems and recombinant baculovirus expression in insect cells). The expression vectors require that the pertinent sequence, i.e., nucleotide sequences that encode the peptides described herein, be operably linked to a promoter.

As it has been found that human HLA-A2 molecules present a NY-CO-58 HLA class I binding peptide, the expression vector may also include a nucleic acid sequence coding for an HLA-A2 molecule. In a situation where the vector contains both coding sequences, it can be used to transfect a cell which does not normally express either one. The NY-CO-58 HLA class I binding peptide coding sequence may be used alone, when, e.g. the host cell already expresses an HLA-A2 molecule. Of course, there is no limit on the particular host cell that can be used as the vectors, which contain the two coding sequences, may be used in host cells which do not express HLA-A2 molecules if desired, and the nucleic acid coding for the NY-CO-58 HLA class I binding peptide can be used in antigen presenting cells that express an HLA-A2 molecule.

Similarly, it has been found that human HLA-DR molecules present a NY-CO-58 HLA class II binding peptide, the expression vector may also include a nucleic acid sequence coding for an HLA-DR molecule. In a situation where the vector contains both coding sequences, it can be used to transfect a cell which does not normally express either one. The NY-CO-58 HLA class II binding peptide coding sequence may be used alone, when, e.g. the host cell already expresses an HLA-DR molecule. There is no limit on the particular host cell which can be used as the vectors, which contain the two coding sequences, may be used in host cells which do not express HLA-DR molecules if desired, and the nucleic acid coding for the NY-CO-58 HLA class II binding peptide can be used in antigen presenting cells which express an HLA-DR molecule. In some embodiments, the HLA-DR molecule is an HLA-DR1 molecule. In some embodiments the HLA-DR molecule is an HLA-DR11 molecule. In some embodiments, the HLA-DR molecule is an HLA-DR13 molecule and in certain embodiments, the HLA-DR molecule is an HLA-DR15 molecule.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or after integration into the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

In some embodiments, of the invention, the expression vectors contain sequences which target a NY-CO-58 family polypeptide, or a HLA class II binding peptide derived therefrom, to the endosomes of a cell in which the protein or peptide is expressed. HLA class II molecules contain an invariant chain (Ii) which impedes binding of other molecules to the HLA class II molecules. This invariant chain is cleaved in endosomes, thereby permitting binding of peptides by HLA class II molecules. Therefore it is preferable that the NY-CO-58 HLA class II binding peptides and precursors thereof (e.g. the various NY-CO-58 proteins that contain HLA class II binding peptides as identified herein) are targeted to the endosome, thereby enhancing NY-CO-58 HLA class II binding peptide binding to HLA class II molecules. Targeting signals for directing molecules to endosomes are known in the art and these signals conveniently can be incorporated in expression vectors such that fusion proteins which contain the endosomal targeting signal are produced. Sanderson et al. (*Proc. Nat'l. Acad. Sci. USA* 92:7217-7221, 1995), Wu et al. (*Proc. Nat'l. Acad. Sci. USA* 92:11671-11675, 1995) and Thomson et al (*J. Virol.* 72:2246-2252, 1998) describe endosomal targeting signals (including invariant chain Ii and lysosomal-associated membrane protein LAMP-1) and their use in directing antigens to endosomal and/or lysosomal cellular compartments.

Endosomal targeting signals such as invariant chain also can be conjugated to NY-CO-58 proteins or peptides by non-peptide bonds (i.e. not fusion proteins) to prepare a conjugate capable of specifically targeting NY-CO-58 proteins. Specific examples of covalent bonds include those wherein bifunctional cross-linker molecules are used. The cross-linker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available cross-linkers are reactive with one or more of the following groups; primary amines, secondary amines, sulfhydryls, carboxyls, carbonyls and carbohydrates. One of ordinary skill in the art will be able to ascertain without undue experimentation the preferred molecule for linking the endosomal targeting moiety and NY-CO-58 peptide or protein, based on the chemical properties of the molecules being linked and the preferred characteristics of the bond or bonds.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a NY-CO-58 HLA class II binding peptide. That heterologous DNA (RNA) is placed under operable control of transcriptional elements to permit the expression of the heterologous DNA in the host cell. As described herein, such expression constructs optionally also contain nucleotide sequences which encode endosomal targeting signals, preferably human invariant chain or a targeting fragment thereof Preferred systems for mRNA expression in mammalian cells are those such as pRc/CMV and pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extra-chromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992). The use of the adenovirus as an Adeno.P1A recombinant is disclosed by Warnier et al., in intradermal injection in mice for immunization against P1A (*Int. J. Cancer,* 67:303-310, 1996). Recombinant vectors including viruses selected from the group consisting of adenoviruses, adeno-associated viruses, poxviruses including vaccinia viruses and attenuated poxviruses such as ALVAC, NYVAC, Semliki Forest virus, Venezuelan equine encephalitis virus, retroviruses, Sindbis virus, Ty virus-like particle, other alphaviruses, VSV, plasmids (e.g. "naked" DNA), bacteria (e.g. the bacterium Bacille Calmette Guerin, attenuated *Salmonella*), and the like can be used in such delivery, for example, for use as a vaccine.

The invention also embraces so-called expression kits, which allow the artisan to prepare a desired expression vector or vectors. Such expression kits include at least separate portions of at least two of the previously discussed materials. Other components may be added, as desired.

The invention as described herein has a number of uses, some of which are described herein. The following uses are described for NY-CO-58 HLA class I and class II binding peptides. The invention permits the artisan to diagnose a disorder characterized by expression of a NY-CO-58 HLA class I or class II binding peptide. These methods involve determining expression of a NY-CO-58 HLA class I or class II binding peptide, or a complex of a NY-CO-58 HLA class I or class II binding peptide and an HLA class I or class II molecule, respectively, in a biological sample. The expression of a peptide or complex of peptide and HLA class I or class II molecule can be determined by assaying with a binding partner for the peptide or complex, such as an antibody.

The invention also permits the artisan to treat a subject having a disorder characterized by expression of a NY-CO-58 peptide. Treatments include administering an agent that enriches in the subject a complex of a NY-CO-58 HLA class I or class II binding peptide and an HLA class I or class II molecule, and administering CD8$^+$ T cells or CD4$^+$ T lymphocytes that are specific for such complexes including T cells transfected or transduced to express T cell receptors that include the TCR sequences disclosed herein. Agents useful in the foregoing treatments include NY-CO-58 HLA class I and class II binding peptides and functional variants thereof, endosome-targeted fusion proteins which include such NY-CO-58 peptides, nucleic acids that express such proteins and peptides (including viruses which contain the nucleic acids), complexes of such peptides and HLA class I and/or class II binding molecules (e.g. HLA-A2, HLA-DR including HLA-DR1, HLA-DR11, HLA-DR13, and HLA-DR15), antigen presenting cells bearing complexes of a NY-CO-58 HLA class I or class II binding peptide and an HLA class I or class II binding molecule, and the like. The invention also allows one to selectively enrich a population to T cells for CD8$^+$ T cells specific for NY-CO-58 HLA class I binding peptides or to selectively enrich a population of T lymphocytes for CD4$^+$ T lymphocytes specific for a NY-CO-58 HLA class II binding peptide, for example by exposing a population of cells to a complex of a NY-CO-58 HLA class I or class II binding peptide and an HLA class I or class II binding molecule, respectively.

The isolation of the NY-CO-58 HLA class I and class II binding peptides also makes it possible to isolate nucleic acids which encode the NY-CO-58 HLA class I and class II binding peptides. Nucleic acids can be used to produce in vitro or in prokaryotic or eukaryotic host cells the NY-CO-58 HLA class I and/or class II binding peptides. A variety of methodologies well-known to the skilled practitioner can be utilized to obtain isolated NY-CO-58 HLA class I or class II binding peptides. For example, an expression vector may be introduced into cells to cause production of the peptides. In another method, mRNA transcripts may be microinjected or otherwise introduced into cells to cause production of the encoded peptides. Translation of mRNA in cell-free extracts such as the reticulocyte lysate system also may be used to produce peptides. Peptides comprising the NY-CO-58 HLA class I and/or class II binding peptides of the invention may also be synthesized in vitro. Those skilled in the art also can readily follow known methods for isolating peptides in order to obtain isolated NY-CO-58 HLA class I and/or class II binding peptides. These include, but are not limited to, immunochromatography, HPLC, size-exclusion chromatography, ion-exchange chromatography and immune-affinity chromatography.

These isolated NY-CO-58 HLA class I and class II binding peptides, proteins which include such peptides, or complexes (including soluble complexes such as tetramers) of the peptides and HLA class I and class II molecules, such as HLA-A2, HLA-DR1, HLA-DR11, HLA-DR13, and HLADR15 molecules, may be combined with materials such as adjuvants to be used to induce immune responses in subjects that are useful in treating disorders characterized by expression of the HLA class I and/or class II binding peptide. In addition, medicaments that are useful to induce an immune response in a subject can be prepared from cells that present the NY-CO-58 HLA class II binding peptide/HLA complexes on their surface. For HLA Class II binding peptides this include cells such as dendritic cells, B cells, non-proliferative transfectants, etcetera. In all cases where cells are used as a to induce an immune response, these can be cells transfected with coding sequences for one or both of the components necessary to stimulate CD4$^+$ lymphocytes or CD8$^+$ T cells, or can be cells which already express both molecules without the need for transfection. For example, autologous antigen presenting cells can be isolated from a patient and treated to obtain cells that present NY-CO-58 epitopes in association of HLA class I and HLA class II molecules. These cells would be capable of stimulating both CD4$^+$ and CD8$^+$ cell responses. Such antigen presenting cells can be obtained by infecting dendritic cells with recombinant viruses encoding an Ii. NY-CO-58 fusion protein. Dendritic cells also can be loaded with HLA class I and HLA class II epitopes.

Compositions of the invention that are useful to stimulate an immune response also encompass naked DNA or RNA, encoding a NY-CO-58 HLA class I or class II binding peptide or precursor thereof, which may be produced in vitro and administered via injection, particle bombardment, nasal aspiration and other methods. Compositions of the "naked nucleic acid" type have been demonstrated to provoke an immunological response including generation of CTLs specific for the peptide encoded by the naked nucleic acid (*Science* 259: 1745-1748, 1993). Compositions of the invention that are useful to stimulate an immune response may also include nucleic acids packaged in a virus, liposome or other particle, including polymeric particles useful in drug delivery.

The immune response generated or enhanced by any of the treatments described herein can be monitored by various methods known in the art. For example, the presence of T cells specific for a given antigen can be detected by direct labeling of T cell receptors with soluble fluorogenic MHC molecule tetramers which present the antigenic peptide (Altman et al., *Science* 274:94-96, 1996; Dunbar et al., *Curr. Biol.* 8:413-416, 1998). Briefly, soluble MHC class I molecules are folded in vitro in the presence of β2-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio of 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein. The use of MHC class II molecules as tetramers was recently demonstrated by Crawford et al. (*Immunity* 8:675-682, 1998; see also Dunbar and Ogg, *J. Immunol. Methods* 268(1):3-7, 2002; Arnold et al., *J. Immunol. Methods* 271(1-2):137-151, 2002). Multimeric soluble MHC class II molecules were complexed with a covalently attached peptide (which can be attached with or without a linker molecule), but also can be loaded onto class II molecules. The class II tetramers were shown to bind with appropriate specificity and affinity to specific T cells. Thus tetramers can be used to monitor both $CD4^+$ and $CD8^+$ cell responses to immune response inducing protocols. Methods for preparation of multimeric complexes of MHC class II molecules are described in Hugues et al., *J. Immunological Meth.* 268: 83-92, (2002) and references cited therein, each of which is incorporated by reference in its entirety.

The NY-CO-58 polypeptides (e.g. fragments of full-length NY-CO-58), as well as complexes of NY-CO-58 HLA class I and/or class II binding peptides and their respective HLA molecule, also may be used to produce antibodies, using standard techniques well known to the art. (See additional details above herein). Standard reference works setting forth the general principles of antibody production include Catty, D., *Antibodies, A Practical Approach*, Vol. 1, IRL Press, Washington D.C. (1988); Klein, J., *Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology*, in *Laboratory Techniques and Biochemistry and Molecular Biology*, Vol. 13 (Burdon, R. et al. EDS.), Elsevier Amsterdam (1984); and Eisen, H. N., *Microbiology*, third edition, Davis, B. D. et al. EDS. (Harper & Rowe, Philadelphia (1980).

Methods for identifying Fab molecules endowed with the antigen-specific, HLA-restricted specificity of T cells has been described by Denkberg et al. *Proc. Nat'l. Acad. Sci. USA* 99:9421-9426 (2002) and Cohen et al. *Cancer Res.* 62:5835-5844 (2002), both of which are incorporated herein by reference. Methods for generating and identifying other antibody molecules, e.g., scFv and diabodies are well known in the art, see e.g., Bird et al., *Science*, 242:423-426 (1988); Huston et al., *Proc. Nat'l. Acad. Sci. USA* 85:5879-5883 (1988); Mallender and Voss, *J. Biol. Chem.* 269:199-206 (1994); Ito and Kurosawa, *J. Biol. Chem.* 27: 20668-20675 (1993), and Gandecha et al., *Prot. Express. Purif.* 5: 385-390 (1994).

The immunogenic response induced in a subject according to the methods of the present invention can be induced using any of a variety of methods, including administering polypeptides, fragments of polypeptides, cells expressing the full-length polypeptide (e.g. SEQ ID NO:20) or fragments thereof and an appropriate HLA class II molecule, and the like to an animal to induce an immune response. Polyclonal and monoclonal antibodies to full-length NY-CO-58 full length polypeptide and/or immunogenic fragments thereof, may be done according to techniques well known in the art. Binding molecules can also be identified by screening libraries of binding peptides (e.g., phage display libraries); the binding molecules can be incorporated recombinantly into antibody or TCR molecules using standard methodologies.

The antibodies of this invention can be used for experimental purposes (e.g., localization of the HLA/peptide complexes, immunoprecipitations, Western blots, flow cytometry, ELISA etc.) as well as diagnostic or therapeutic purposes (e.g., assaying extracts of tissue biopsies for the presence of HLA/peptide complexes, targeting delivery of cytotoxic or cytostatic substances to cells expressing the appropriate HLA/peptide complex). The antibodies of this invention are useful for the study and analysis of antigen presentation on tumor cells and can be used to assay for changes in the HLA/peptide complex expression before, during or after a treatment protocol, e.g., vaccination with peptides, antigen presenting cells, HLA/peptide tetramers, adoptive transfer or chemotherapy.

The full-length NY-CO-58 polypeptide and/or immunogenic fragments thereof may be administered to a subject in conjunction with additionally therapeutically useful agents by using standard methods well-known in the art. As used herein, "therapeutically useful agents" include any therapeutic molecules, which are preferably targeted selectively to a cell expressing the HLA/peptide complexes, including antineoplastic agents, radioiodinated compounds, toxins, other cytostatic or cytolytic drugs. Antineoplastic therapeutics are well known and include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-.alpha., lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division). The immunogenic fragments or full-length NY-CO-58 polypeptides may be administered to a subject having a pathological condition characterized by the presentation of the HLA/peptide complexes of this invention, e.g., melanoma or other cancers, e.g. colon caner, in an amount sufficient to alleviate the symptoms associated with the pathological condition.

Soluble T cell receptors (TCRs) which specifically bind to the HLA/peptide complexes described herein are also an aspect of this invention. In their soluble form, T cell receptors are analogous to a monoclonal antibody in that they bind to HLA/peptide complex in a peptide-specific manner. Immobilized TCRs or antibodies may be used to identify and purify unknown peptide/HLA complexes which may be involved in cellular abnormalities. Methods for identifying and isolating soluble TCRs are known in the art, see for example WO 99/60119, WO 99/60120 (both incorporated herein by reference) which describe synthetic multivalent T cell receptor complexes for binding to peptide-MHC complexes. Recombinant, refolded soluble T cell receptors are specifically described. Such receptors may be used for delivering therapeutic agents or detecting specific peptide-MHC complexes expressed by tumor cells. WO 02/088740 (incorporated by reference) describes a method for identifying a substance that binds to a peptide-MHC complex. A peptide-MHC complex is formed between a predetermined MHC and peptide known to bind to such predetermined MHC. The complex is then use to screen or select an entity that binds to the peptide-MHC complex such as a T cell receptor. The method could also be applied to the selection of monoclonal antibodies that bind to the predetermined peptide-MHC complex.

When "disorder" or "condition" is used herein, it refers to any pathological condition where the NY-CO-58 HLA class I or class II binding peptide is expressed. Such disorders include cancers, such as biliary tract cancer; bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS-associated leukemias and adult T-cell leukemia lymphoma; intraepithelial neoplasms including Bowen's disease and Paget's disease; liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilms tumor.

Some therapeutic approaches based upon the disclosure are premised on inducing a response by a subject's immune system to NY-CO-58 HLA class I and/or class II binding peptide presenting cells. For example, one such approach relating to HLA class II binding peptide presenting cells includes the administration of autologous CD4$^+$ T cells specific to the complex of NY-CO-58 HLA class II binding peptide and an HLA class II molecule to a subject with abnormal cells of the phenotype at issue. It is within the skill of the artisan to develop such CD4$^+$ T cells in vitro. Generally, a sample of cells taken from a subject, such as blood cells, are contacted with a cell presenting the complex and capable of provoking CD4$^+$ lymphocytes to proliferate; alternatively, T cells of appropriate specificity can be sorted from a larger population of T cells using an HLA-NY-CO-58 peptide multimer (e.g., tetramer). The target cell can be a transfectant, such as a COS cell, or an antigen presenting cell bearing HLA class II molecules, such as dendritic cells or B cells. These transfectants present the desired complex of their surface and, when combined with a CD4$^+$ T lymphocyte of interest, stimulate its proliferation. COS cells are widely available, as are other suitable host cells. Specific production of CD4$^+$ T lymphocytes is described below. The clonally expanded autologous CD4$^+$ T lymphocytes then are administered to the subject. The CD4$^+$ T lymphocytes then stimulate the subject's immune response, thereby achieving the desired therapeutic goal.

CD4$^+$ T cells specific to a complex of a NY-CO-58 HLA class II binding peptide and an HLA class II molecule also can be prepared by transfecting or transducing T lymphocytes with T cell receptor sequences including the CDR sequences described herein, as noted above.

CTL proliferation can be increased by increasing the level of tryptophan in T cell cultures, by inhibiting enzymes which catabolizes tryptophan, such as indoleamine 2,3-dioxygenase (IDO), or by adding tryptophan to the culture (see, e.g., PCT application WO99/29310). Proliferation of T cells is enhanced by increasing the rate of proliferation and/or extending the number of divisions of the T cells in culture. In addition, increasing tryptophan in T cell cultures also enhances the lytic activity of the T cells grown in culture.

The foregoing therapy assumes that at least some of the subject's abnormal cells present the relevant HLA/peptide complex. This can be determined very easily, as the art is very familiar with methods for identifying cells which present a particular HLA molecule, as well as how to identify cells expressing DNA of the pertinent sequences, in this case a NY-CO-58 sequence.

The foregoing therapy is not the only form of therapy that is available in accordance with the invention. CD4$^+$ T lymphocytes can also be provoked in vivo, using a number of approaches. One approach is the use of non-proliferative cells expressing the complex. The cells used in this approach may be those that normally express the complex, such as dendritic cells or cells transfected with one or both of the genes necessary for presentation of the complex. Chen et al., (*Proc. Natl. Acad. Sci. USA* 88: 110-114, 1991) exemplifies this approach, showing the use of transfected cells expressing HPV-E7 peptides in a therapeutic regime. Various cell types may be used. Similarly, vectors carrying one or both of the genes of interest may be used. Viral or bacterial vectors are especially preferred. For example, nucleic acids which encode a NY-CO-58 HLA class I or a class II binding peptide may be operably linked to promoter and enhancer sequences which direct expression of the NY-CO-58 HLA class I or class II binding peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding NY-CO-58 HLA class I or class II binding peptides. Nucleic acids encoding a NY-CO-58 HLA class I or class II binding peptide also may be inserted into a retroviral genome, thereby facilitating integration of the nucleic acid into the genome of the target tissue or cell type. In these systems, the gene of interest is carried by a microorganism, e.g., a vaccinia virus, poxviruses in general, adenovirus, herpes simplex virus, retrovirus or the bacteria BCG, and the materials de facto "infect" host cells. The cells which result present the complex of interest, and are recognized by autologous CD4$^+$ or CD8$^+$ T cells, which then proliferate.

A similar effect can be achieved by combining a NY-CO-58 HLA class I and/or class II binding peptide with an adjuvant to facilitate incorporation into HLA class I or class II presenting cells in vivo. If larger than the HLA class I or class II binding portion, the NY-CO-58 HLA class I or class II binding peptide can be processed if necessary to yield the peptide partner of the HLA molecule while the TRA is presented without the need for further processing. Generally, subjects can receive an intradermal injection of an effective amount of the NY-CO-58 HLA class I or class II binding peptide. Initial doses can be followed by booster doses, following immunogenic response inducing protocols standard in the art.

A method that may be used for facilitating incorporation of NY-CO-58 HLA class II binding peptides into HLA class II presenting cells is by expressing in the presenting cells a polypeptide which includes an endosomal targeting signal fused to a NY-CO-58 polypeptide that includes the class II binding peptide. Particularly preferred are NY-CO-58 fusion proteins that contain human invariant chain Ii.

Any of the foregoing compositions or protocols can include also NY-CO-58 HLA class I binding peptides for induction of a cytolytic T lymphocyte response. The NY-CO-58 polypeptide fragments can be processed in a cell to produce both HLA class I and HLA class II responses. Several such peptides have been described in U.S. Pat. Nos. 5,585,461 and 5,591,430, and PCT published application PCT/US95/03657, as well as by Gaugler et al. (*J. Exp. Med.* 179: 921-930, 1994), van der Bruggen et al. (*Eur. J. Immunol.* 24:3038-3043, 1994), and Herman et al. (*Immunogenetics* 43:377-383, 1996). By administering NY-CO-58 polypeptide fragments that bind HLA class I and class II molecules (or nucleic acid encoding such peptides), an improved immune response may be provided by inducing both T helper cells and T killer cells (CTLs).

In addition, non-NY-CO-58 tumor associated peptides also can be administered to increase immune response via HLA class I and/or class II. It is well established that cancer cells can express more that one tumor associated gene. It is within the scope of routine experimentation for one of ordinary skill in the art to determine whether a particular subject expresses additional tumor associated genes, and then include HLA class I and/or HLA class II binding peptides derived from expression products of such genes in the foregoing NY-CO-58 compositions.

Especially preferred are nucleic acids encoding a series of epitopes, known as "polytopes". The epitopes can be arranged in sequential or overlapping fashion (see, e.g., Thomson et al., *Proc. Natl. Acad. Sci. USA* 92:5845-5849, 1995; Gilbert et al., *Nature Biotechnol.* 15:1280-1284, 1997), with or without the natural flanking sequences, and can be separated by unrelated linker sequences if desired. The polytope is processed to generated individual epitopes which are recognized by the immune system for generation of immune responses.

Thus, for example, NY-CO-58 HLA class I and binding peptides can be combined with peptides from other tumor rejection antigens (e.g. by preparation of hybrid nucleic acids or polypeptides) and/or with NY-CO-58 HLA class II binding peptides to form "polytopes". Exemplary tumor associated peptide antigens that can be administered to induce or enhance an immune response are derived from tumor associated genes and encoded proteins including MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1 (CT-7), MAGE-C2 (CT-10), NY-ESO-1, LAGE-1, SSX-1, SSX-2 (HOM-MEL-40), SSX-4, SSX-5, and SCP-1. For example, antigenic peptides characteristic of tumors include those listed in published PCT application WO 00/20581 (PCT/US99/21230).

Other examples of HLA class I and HLA class II binding peptides will be known to one of ordinary skill in the art (for example, see Coulie, *Stem Cells* 13:393-403, 1995; there is a listing on the website of the journal Cancer Immunity in the "Peptide Database" section, www.cancerimmunity.org/peptidedatabase/Tcellepitopes.htm), and can be used in the invention in a like manner as those disclosed herein. One of ordinary skill in the art can prepare polypeptides comprising one or more NY-CO-58 fragments and/or the full-length polypeptide and one or more of the foregoing tumor rejection peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes to an induce immunogenic response is well known in the art (see, e.g., Thomson et al., *Proc. Acad. Natl. Acad. Sci. USA* 92(13):5845-5849, 1995; Gilbert et al., *Nature Biotechnol.* 15(12):1280-1284, 1997; Thomson et al., *J. Immunol.* 157(2):822-826, 1996; Tam et al., *J. Exp. Med.* 171(1):299-306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8):1951-1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

The invention involves the use of various materials disclosed herein to induce an immune response in subjects. As used herein, "inducing an immune response" means increasing or activating an immune response against an antigen. It does not require elimination or eradication of a condition but rather contemplates the clinically favorable enhancement of an immune response toward an antigen. Generally accepted animal models, can be used for testing of immunization against cancer using a NY-CO-58 molecule of the invention. For example, human cancer cells can be introduced into a mouse to create a tumor, and one or more NY-CO-58 molecules of the invention can be delivered by the methods described herein. The effect on the cancer cells (e.g., reduction of tumor size) can be assessed as a measure of the effectiveness of the NY-CO-58 molecule administration. Of course, testing of the foregoing animal model using more conventional methods for inducing an immune response include the administration of one or more NY-CO-58 polypeptides or fragments derived therefrom, optionally combined with one or more adjuvants and/or cytokines to boost the immune response.

Methods for inducing an immune response, including formulation of an immunizing composition and selection of doses, route of administration and the schedule of administration (e.g. primary and one or more booster doses), are well known in the art. The tests also can be performed in humans, where the end point is to test for the presence of enhanced levels of circulating CTLs against cells bearing the antigen, to test for levels of circulating antibodies against the antigen, to test for the presence of cells expressing the antigen and so forth.

As part of the immune response-inducing compositions of the invention, one or more substances that potentiate an immune response may be administered along with the peptides described herein. Such substances include adjuvants and cytokines. An adjuvant is a substance incorporated into or administered with antigen that potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella* minnesota Re 595 lipopolysaccharide; saponins including QS21 (SmithKline Beecham), a pure QA-21 saponin purified from *Quillja saponaria* extract; DQS21, described in PCT application WO96/33739 (SmithKline Beecham), ISCOM (CSL Ltd., Parkville, Victoria, Australia) derived from the bark of the *Quillaia saponaria* molina tree; QS-7, QS-17, QS-18, and QS-L1 (So et al., Mol. Cells. 7:178-186, 1997); incomplete Freund's adjuvant; complete Freund's adjuvant; montanide; alum; CpG oligonucleotides (see e.g. Kreig et al., Nature 374:546-9, 1995); various water-in-oil emulsions prepared from biodegradable oils such as squalene and/or tocopherol; and factors that are taken up by the so-called 'toll-like receptor 7' on certain immune cells that are found in the outside part of the skin, such as imiquimod (3M, St. Paul, Minn.). Preferably, the antigens are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 µg to about 100 µg. Other adjuvants are known in the art and can be used in the invention (see, e.g. Goding, Monoclonal Antibodies: Principles and Practice, 2nd Ed., 1986). Methods for the preparation of mixtures or emulsions of polypeptide and adjuvant are well known to those of skill in the art of inducing and/or enhancing an immune response and the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268:1432-1434, 1995), GM-CSF and IL-18. Thus cytokines can be administered in conjunction with antigens and adjuvants to increase the immune response to the antigens. There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *Proc. Nat'l Acad. Sci. USA* 95:6284-6289, 1998).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol.* 154:5637-5648, 1995). Tumor cell transfection with B7 has been discussed in relation to in vitro CTL expansion for adoptive transfer immunotherapy by Wang et al. (*J. Immunother.* 19:1-8, 1996). Other delivery mechanisms for the B7 molecule would include nucleic acid (naked DNA) immunization (Kim et al., *Nature Biotechnol.* 15:7:641-646, 1997) and recombinant viruses such as adeno and pox (Wendtner et al., *Gene Ther.* 4:726-735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., *Nature* 397:263-266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.,* 158:637-642, 1997; Fenton et al., *J. Immunother.,* 21:95-108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature* 393:474, 1998; Bennett et al., *Nature* 393:478, 1998; Schoenberger et al., *Nature* 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor associated antigens which are normally encountered outside of an inflammatory context or are presented by non-professional APCs (tumor cells). Other methods for inducing maturation of dendritic cells, e.g., by increasing CD40-CD40L interaction, or by contacting DCs with CpG-containing oligodeoxynucleotides or stimulatory sugar moieties from extracellular matrix, are known in the art. In these situations Th help and B7 costimulation signals are not provided. This mechanism might be used in the context of antigen pulsed DC based therapies or in situations where Th epitopes have not been defined within known tumor associated antigen precursors.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of inducing an immune response, the desired response is an increase in antibodies or T lymphocytes which are specific for the NY-CO-58 immunogen(s) employed. These desired responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

The invention contemplates delivery of nucleic acids, polypeptides or fragments thereof for immune-response induction. Delivery of polypeptides and fragments thereof can be accomplished according to standard immunogenic response inducing protocols which are well known in the art. In another embodiment, the delivery of nucleic acid is accomplished by ex vivo methods, i.e. by removing a cell from a subject, genetically engineering the cell to include a colon cancer-associated polypeptide, and reintroducing the engineered cell into the subject. One example of such a procedure is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo nucleic acid delivery using vectors such as viruses and targeted liposomes also is contemplated according to the invention.

A virus vector for delivering a nucleic acid encoding a cancer-associated polypeptide is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., *Virology* 219:220-227, 1996; Eloit et al., *J. Virol.* 7:5375-5381, 1997; Chengalvala et al., *Vaccine* 15:335-339, 1997), a modified retrovirus (Townsend et al., *J. Virol.* 71:3365-3374, 1997), a nonreplicating retrovirus (Irwin et al., *J. Virol.* 68:5036-5044, 1994), a replication defective Semliki Forest virus (Zhao et al., *Proc. Natl. Acad. Sci. USA* 92:3009-3013, 1995), canarypox virus and highly attenuated vaccinia virus derivative (Paoletti, *Proc. Natl. Acad. Sci. USA* 93:11349-11353, 1996), non-replicative vaccinia virus (Moss, *Proc. Natl. Acad. Sci. USA* 93:11341-11348, 1996), replicative vaccinia virus (Moss, *Dev. Biol. Stand.* 82:55-63, 1994), Venzuelan equine encephalitis virus (Davis et al., *J. Virol.* 70:3781-3787, 1996), Sindbis virus (Pugachev et al., *Virology* 212:587-594, 1995), and Ty virus-like particle (Allsopp et al., *Eur. J. Immunol* 26:1951-1959, 1996). A preferred virus vector is an adenovirus.

Preferably the foregoing nucleic acid delivery vectors: (1) contain exogenous genetic material that can be transcribed and translated in a mammalian cell and that can induce an immune response in a host, and (2) contain on a surface a ligand that selectively binds to a receptor on the surface of a target cell, such as a mammalian cell, and thereby gains entry to the target cell.

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection or infection with the foregoing viruses including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. Preferred antibodies include antibodies which selectively bind a colon cancer-associated antigen, alone or as a complex with a MHC molecule. Especially preferred are monoclonal antibodies. Where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

According to a further aspect of the invention, compositions containing the nucleic acid molecules, proteins, and binding polypeptides of the invention are provided. The compositions contain any of the foregoing therapeutic agents in an optional pharmaceutically acceptable carrier. Thus, in a related aspect, the invention provides a method for forming a medicament that involves placing a therapeutically effective amount of the therapeutic agent in the pharmaceutically acceptable carrier to form one or more doses. The effectiveness of treatment or prevention methods of the invention can be determined using standard diagnostic methods described herein.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term "carrier" denotes an organic or inorganic ingredient, natural or synthetic, with which the active ingredient is combined to facilitate the application. The components of the pharmaceutical compositions also are capable of being comingled with the molecules of the present invention, and with each other, in a manner such that there is no interaction which would substantially impair the desired pharmaceutical efficacy.

The therapeutics of the invention can be administered by any conventional route, including injection or by gradual infusion over time. The administration may, for example, be oral, intravenous, intratumoral, intraperitoneal, intramuscular, intracavity, subcutaneous, or transdermal.

The compositions of the invention are administered in effective amounts. An "effective amount" is that amount of a colon cancer-associated polypeptide composition that alone, or together with further doses, produces the desired response, e.g. increases an immune response to the colon cancer-associated polypeptide. In the case of treating a particular disease or condition characterized by expression of one or more colon cancer-associated polypeptides (e.g. colon cancer), the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of an NY-CO-58 polypeptide or nucleic acid encoding an NY-CO-58 polypeptide for producing the desired response in a unit of weight or volume suitable for administration to a patient. The response can, for example, be measured by determining the immune response following administration of the colon cancer-associated polypeptide composition (e.g. an NY-CO-59 composition) via a reporter system by measuring downstream effects such as gene expression, or by measuring the physiological effects of the colon cancer-associated polypeptide composition, such as regression of a tumor or decrease of disease symptoms. Other assays will be known to one of ordinary skill in the art and can be employed for measuring the level of the response.

The doses of cancer-associated molecule (e.g. NY-CO-58 molecule) compositions (e.g., polypeptide, peptide, antibody, cell or nucleic acid) administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, for treatments for eliciting or increasing an immune response, doses of colon cancer-associated antigen (e.g. NY-CO-58 antigen) are formulated and administered in doses between 1 ng and 1 µg, and preferably between 10 ng and 100 µg, according to any standard procedure in the art. Where nucleic acids encoding colon cancer-associated polypeptides or variants thereof are employed, doses of between 1 ng and 0.1 mg generally will be formulated and administered according to standard procedures. Other protocols for the administration of colon cancer-associated polypeptide compositions will be known to one of ordinary skill in the art, in which the dose amount, schedule of injections, sites of injections, mode of administration (e.g., intratumoral) and the like vary from the foregoing. Administration of colon cancer-associated polypeptide compositions to mammals other than humans, e.g. for testing purposes or veterinary therapeutic purposes, is carried out under substantially the same conditions as described above.

Where colon cancer-associated polypeptides (e.g. NY-CO-58 polypeptides, or fragments thereof) are used to induce an immune response and/or for vaccination, modes of administration which effectively deliver the polypeptide and adjuvant, such that an immune response to the polypeptide is increased, can be used. For administration of a polypeptide in adjuvant, preferred methods include intradermal, intravenous, intramuscular and subcutaneous administration. Although these are preferred embodiments, the invention is not limited by the particular modes of administration disclosed herein. Standard references in the art (e.g., Remington's Pharmaceutical Sciences, 18th edition, 1990) provide modes of administration and formulations for delivery of immunogens with adjuvant or in a non-adjuvant carrier.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, and lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases, and the like.

The pharmaceutical agents of the invention may be administered alone, in combination with each other, and/or in combination with other anti-cancer drug therapies and/or treatments. These therapies and/or treatments may include, but are not limited to: surgical intervention, chemotherapy, radiotherapy, and adjuvant systemic therapies.

The invention also provides a pharmaceutical kit comprising one or more containers comprising one or more of the pharmaceutical compounds or agents of the invention. Additional materials may be included in any or all kits of the invention, and such materials may include, but are not limited to buffers, water, enzymes, tubes, control molecules, etc. The kit may also include instructions for the use of the one or more pharmaceutical compounds or agents of the invention for the treatment of cancer.

The invention further includes nucleic acid or protein microarrays with colon cancer-associated peptides or nucleic acids encoding such polypeptides. In this aspect of the invention, standard techniques of microarray technology are utilized to assess expression of the colon cancer-associated polypeptides and/or identify biological constituents that bind such polypeptides. The constituents of biological samples include antibodies, lymphocytes (particularly T lymphocytes), and the like. Protein microarray technology, which is also known by other names including: protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," Science 289(5485):1760-1763, 2000. Nucleic acid arrays, particularly arrays that bind colon cancer-associated peptides, also can be used for diagnostic applications, such as for identifying subjects that have a condition characterized by colon cancer-associated polypeptide expression.

Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezo-electric delivery. Probes may be covalently linked to the substrate.

Targets are peptides or proteins and may be natural or synthetic. The tissue may be obtained from a subject or may be grown in culture (e.g. from a cell line).

In some embodiments of the invention, one or more control peptide or protein molecules are attached to the substrate. Preferably, control peptide or protein molecules allow determination of factors such as peptide or protein quality and binding characteristics, reagent quality and effectiveness, hybridization success, and analysis thresholds and success.

Nucleic acid microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol. 21, January 1999, the entire contents of which is incorporated by reference herein.

According to the present invention, nucleic acid microarray substrates may include but are not limited to glass, silica, aluminosilicates, borosilicates, metal oxides such as alumina and nickel oxide, various clays, nitrocellulose, or nylon. In all embodiments, a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of more than two of the colon cancer-associated polypeptide nucleic acid molecules set forth herein, or one of the novel colon cancer-associated polypeptide nucleic acid molecules as described herein. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or olignucleotide to the substrate. These agents or groups may include, for example, amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Chipping Forecast, 1999) or chromium. In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezoelectric delivery. Probes may be covalently linked to the substrate with methods that include, but are not limited to, UV-irradiation. In another embodiment probes are linked to the substrate with heat.

Targets for microarrays are nucleic acids selected from the group, including but not limited to: DNA, genomic DNA, cDNA, RNA, mRNA and may be natural or synthetic. In all embodiments, nucleic acid target molecules from human tissue are preferred. The tissue may be obtained from a subject or may be grown in culture (e.g. from a cell line).

In embodiments of the invention one or more control nucleic acid molecules are attached to the substrate. Preferably, control nucleic acid molecules allow determination of factors such as nucleic acid quality and binding characteristics, reagent quality and effectiveness, hybridization success, and analysis thresholds and success. Control nucleic acids may include but are not limited to expression products of genes such as housekeeping genes or fragments thereof.

In some embodiments, one or more control nucleic acid molecules are attached to the substrate. Preferably, control nucleic acid molecules allow determination of factors such as binding characteristics, reagent quality and effectiveness, hybridization success, and analysis thresholds and success.

EXAMPLES

Example 1

Method

Serum samples from patients with colon cancer were screened using a modification of the plaque assay, termed a spot assay. In this method, 80×120 mm nitrocellulose membranes were precoated with a film of NZY/0.7% Agarose/2.5 mM IPTG and placed on a reservoir layer of NZY/0.7% Agarose in a 86×128 mm Omni Tray (Nalge Nunc International Corp., Naperville, Ill.). Approximately $1.0 \times 10^5$ pfU of monoclonal phage encoding individual serologically defined colon cancer antigens, in a volume of 20 µl, were mixed with 20 µl of exponentially growing E. coli XL-1 Blue MRF and spotted (0.7-µl aliquots) on the precoated nitrocellulose membranes. Membranes were incubated for 15 hours at 37° C. A total of 75 different serologically defined colon cancer antigens were spotted in duplicate per nitrocellulose membrane. The agarose film was then removed from the membrane and the filters were processed for reactivity with individual serum samples (1:200 dilution), as described in Scanlan, et al., Int. J. Cancer 76:652-658 (1998) and Scanlan, et al., Int. J. Cancer 83:456-64, (1999).

Results

The results (see Table 1) indicate that 37/75 sera (49%) reacted with at least 1 antigen, 17/75 sera (23%) reacted with 2 or more antigens, 6/75 sera (8%) reacted with 3 or more antigens, and 2/75 sera (3%) reacted with 4 or more antigens. The reactivity of individual antigens is shown in Table 2.

TABLE 1

Colon Cancer Serology
Reactivity of 75 sera from colon cancer patients versus 15 antigens comprising, none of which react with normal sera (0/75, assayed by spot blot as described).

| Sera Number | Reactive NY-antigens |
| --- | --- |
| COF1 | Negative |
| COF2 | Negative |
| COF3 | Negative |
| COF4 | Negative |
| COF5 | Negative |
| COF6 | CO61 +++ |
| COF7 | CO26 ++++, ESO-1 ++++, CO61 ++++ |
| COF8 | Negative |
| COF9 | REN32 +++ |
| COF10 | p53 +++, CO58 ++ |
| COF11 | TNKL +, ESO-1 ++++ |
| COF12 | CO94 ++ |
| COF13 | Negative |
| COF14 | Negative |
| COF15 | SSX-2 ++ |
| COF16 | CO45 ++, CO42 ++ |
| COF17 | Negative |
| COF18 | Negative |
| COF19 | Negative |
| COF20 | Negative |
| COF21 | CO 58 + |
| COF22 | TNKL ++, CO45 ++, CO42 ++ |
| COF23 | CO41 ++ |
| CO24 | Negative |
| CO25 | Negative |
| CO26 | TNKL +++ |
| CO27 | CO45 ++++ |
| CO28 | CO9 ++++, ESO-1 ++++, CO58 ++++, CO61 ++ |
| CO29 | MAGE-3 +, ESO-1 + |
| CO30 | p53 +++ |
| CO31 | Negative |
| CO32 | Negative |
| CO33 | MAGE 3 +++ |

TABLE 1-continued

Colon Cancer Serology
Reactivity of 75 sera from colon cancer patients versus 15 antigens comprising, none of which react with normal sera (0/75, assayed by spot blot as described).

| Sera Number | Reactive NY-antigens |
|---|---|
| CO34 | Negative |
| CO35 | Negative |
| CO36 | CO41 +++ |
| CO37 | Negative |
| CO38 | Negative |
| CO39 | Negative |
| CO40 | CO42 +, CO95 + |
| CO41 | Negative |
| CO42 | p53 ++++ |
| CO43 | p53 ++++, CO94 ++++ |
| CO44 | Negative |
| CO45 | p53 +++ |
| CO46 | Negative |
| CO47 | CO61 + |
| CO48 | p53 ++++, MAGE 3 ++ |
| CO49 | Negative |
| CO50 | Negative |
| CO51 | CO9 + |
| COF52 | Negative |
| CO53 | TNKL +, p53 ++++ |
| CO54 | Negative |
| CO55 | ESO-1 ++++ |
| CO56 | Negative |
| CO57 | Negative |
| CO58 | Negative |
| CO59 | Negative |
| CO60 | SSX-1 +, MAGE-3 +, CO42 +, CO61 ++++ |
| CO61 | TNKL ++ |
| **CO62 | **same sera as CO28 |
| **CO63 | **same sera as CO29 |
| CO64 | TNKL + |
| CO65 | Negative |
| **CO66 | **same sera as CO30 |
| CO67 | p53 ++ |
| CO68 | MAGE-3 +, CO42 + |
| CO69 | Negative |
| CO70 | Negative |
| CO71 | REN32 +, MAGE-3 + |
| CO72 | Negative |
| CO73 | REN32 ++, p53 + |
| CO74 | Negative |
| CO75 | p53 +++ |
| CO76 | Negative |
| CO77 | CO94 ++++, CO95 +++, p53 ++ |
| CO78 | CO42 ++, CO94 ++++, CO95 ++ |

TABLE 2

Reactivity of individual antigens (includes autologous where applicable)

| | |
|---|---|
| CO13 (p53) | 13/76 |
| CO-26 (MNK 1): | 2/76 |
| ESO-1: | 5/75 |
| REN-32 (Lamin C): | 3/75 |
| TNKL (BC-203): | 6/75 |
| SSX-2: | 2/75 |
| CO-45 (Tudor like): | 4/76 |
| CO-41 (MBD2): | 3/76 |
| MAGE-3 | 6/75 |
| CO-9 (HDAC 5) | 3/76 |
| CO-42 (TRIP4): | 7/76 |
| CO-61 (HIP1R): | 5/75 |
| CO-58 (KNSL6): | 3/75 |
| CO-94 (seb4D): | 4/75 |
| CO-95 (KIAA1416) | 4/75 |

TABLE 3

| Sequence Name | Sequence Identification Numbers | |
|---|---|---|
| | Nucleotide SEQ ID NO | Protein SEQ ID NO. |
| CO-95 (KIAA1416) | 1 | 16 |
| CO-94 (seb4D) | 2 | 17 |
| CO-9 (HDAC 5) | 3 | 18 |
| CO-61 (HIP1R) | 4 | 19 |
| CO-58 (KNSL6) | 5 | 20 |
| CO-45 | 6 | 21 |
| CO-42 (TRIP4) | 7 | 22 |
| CO-41 (MBD2) | 8 | 23 |
| CO-13 (P53) | 9 | 24 |
| Ren-32 (Lamin C) | 10 | 25 |
| TNKL (BC-203) | 11 | 26 |
| CO-26 (MNK 1) | 12 | 27 |
| SSX-2 | 13 | 28 |
| MAGE-3 | 14 | 29 |
| ESO-1 | 15 | 30 |

Example 2

T Cell Immune Response to the NY-CO-58 Antigen

NY-CO-58 is a novel CT antigen identified from a SEREX analysis of serological responses in colon cancer patients (see Example 1). Colon cancer patients were analyzed for immune responses to antigen NY-CO-58/KNSL-6 at University Klinik Eppendorf in Hamburg. Initially, 15 patient sera were tested for the presence of NY-CO-58 specific autologous serum antibodies. Sera of two of the 15 patients, UKE-16 and UKE-1 were positive for antibodies to NY-CO-58 (+++ and +, respectively).

Given the correlation between humoral and cellular immunity observed with CT antigens such as NY-ESO-1 (Jager et al. *J Exp Med.* 1998 Jan. 19; 187(2):265-70) and SSX2 (Ayyoub et al. *J Immunol.* 2002 Feb. 15; 168(4):1717-22, Tureci et al. *Cancer Res.* 1996 Oct. 15; 56(20):4766-72.), these two patients were analyzed to look for the presence of T cell responses. Nine long peptides (30AA) were synthesized from the sequence of NY-CO-58 (SEQ ID NO:20) on the basis of the presence of anchor motifs for various class I molecules. Five prediction algorithms were used to map potential these potential anchor motifs which correspond to potential epitopes, resulting in the selection of the following polypeptides: 3-32 (SEQ ID NO:31), 51-80 (SEQ ID NO:35), 151-180 (SEQ ID NO:36), 271-300 (SEQ ID NO:37), 375-404 (SEQ ID NO:38), 403-432 (SEQ ID NO:33), 510-539 (SEQ ID NO:39), 633-662 (SEQ ID NO:40), and 692-721 (SEQ ID NO:34).

$CD8^+$ and $CD4^+$ T cells were then purified from peripheral blood lymphocytes (PBLs) from the two patients and were stimulated with these peptides either individually or in pools of 2-3 peptides (Gnjatic et al. *J Immunol.* 2003 Feb. 1; 170 (3):1191-6). The stimulated $CD8^+$ T cells were then tested for recognition of the same stimulator peptide(s), either individually or pools in standard ELISPOT assays (Jager *Proc Natl Acad Sci USA.* 2000 Apr. 25; 97(9):4760-5, Gnjatic et al. *Proc Natl Acad Sci USA.* 2000 Sep. 26; 97(20):10917-22). No specific response was observed for $CD8^+$ T cells from either patient.

In these same patients $CD4^+$ T cell responses were investigated. $CD4^+$ T cells were stimulated with the peptides individually or in pools of 2-3 peptides as done with $CD8^+$ T cells. The stimulated peptides were tested in ELISPOT assays using autologous targets presenting the stimulator peptide(s). NY- CO-58 specific CD4+ T cell responses were observed in both of the seropositive patients. Recognition of control autologous targets, either unpulsed cells or cells presenting irrelevant peptide.

Two peptides reacted very clearly with CD4+ T cells from patient UKE-16. These were NY-CO-58 peptides 3-32 (SEQ ID NO:31) and 692-721 (SEQ ID NO:34). The CD4+ T cells maintained clear and strong specificity for the relevant peptides over extended in vitro culture time. Responses were only seen with CD4+ T cell lines that had been pre-sensitized with the relevant peptide.

An additional sample of PBLs was obtained from patient UKE-16. The patient remained positive for serum NY-CO-58 specific antibody. Again, CD4+ T cells were stimulated with peptides derived from the NY-CO-58 sequence. This time additional "minimal" 12-mer epitopes selected from within the 30-mer polypeptides using the ProPred prediction algorithm (Singh, H. and Raghava, G. P. S. (2001) ProPred: Prediction of HLA-DR binding sites. *Bioinformatics*, 17(12), 1236-37, Propred server available online from Drs Raghava and Singh, Bioinformatics Center, Institute of Microbial Technology, Chandigarh, India). The 12-mer peptides corresponded to amino acid 15-26 (SEQ ID NO:32) and 699-710 (SEQ ID NO:41) of NY-CO-58 (SEQ ID NO:20). Analysis of the responses was carried out by ELISPOT assay as before. Peptide 15-26 was recognized by CD4+ T cells from patient UKE-16 and represents a minimal epitope within amino acid 3-32 (SEQ ID NO:31). This also confirmed that the T cell reactivity was specific to the peptides and not due to an irrelevant contaminant, which would be unlikely to be present within two separate batches of synthetic peptides.

CD4+ T cell responses in the second patient UKE-1, was also analyzed. The CD4+ T cells from this patient were again reactive with NY-CO-58 peptides 3-32 (SEQ ID NO:31) and 692-721 (SEQ ID NO:34). Additionally, this patient also responded to a third NY-CO-58 peptide 403-432 (SEQ ID NO:33).

The results indicate we have identified three CD4+ T cell epitopes from NY-CO-58: (1) 3-32 (SEQ ID NO:31), which can be further defined as a minimal peptide 15-26 (SEQ ID NO:32); (2) 403-432 (SEQ ID NO:33); and (3) 692-721 (SEQ ID NO:34).

An additional 30 colon cancer patients were analyzed and two more donors were found to have autologous serum antibody specific for NY-CO-58. The NY-CO-58 specific T cell response in these patients is evaluated using similar methods as described above.

HLA Typing of the Patients:

| UKE-16: | HLA-DR1, DR13; |
| UKE-1: | HLA-DR11, DR15 |

(genetic typings on DRB1 chain)

TABLE 4

Fragments of NY-CO-58 (SEQ ID NO:20)

| NY-CO-58 residue numbers | Amino acid sequence | SEQ ID NO |
|---|---|---|
| 3-32 | MDSSLQARLFPGLAIKIQRSNGLIHSANVR | 31 |
| 51-80 | TKGKEIDFDDVAAINPELLQLLPLHPKDNL | 35 |

TABLE 4-continued

Fragments of NY-CO-58 (SEQ ID NO:20)

| NY-CO-58 residue numbers | Amino acid sequence | SEQ ID NO |
|---|---|---|
| 151-180 | RPSCPAVAEIPLRMVSEEMEEQVHSIRGSS | 36 |
| 271-300 | QELAKKEIDVISIPSKCLLLVHEPKLKVDL | 37 |
| 375-404 | AMASRDVFLLKNQPCYRKLGLEVYVTFFEI | 38 |
| 403-432 | EIYNGKLFDLLNKKAKLRVLEDGKQQVQVV | 33 |
| 510-539 | RMEGAEINKSLLALKECIRALGQNKAHTPF | 39 |
| 633-662 | SFNEAMTQIRELEEKAMEELKEIIQQGPDW | 40 |
| 692-721 | KHFSALRDVIKALRLAMQLEEQASRQISSK | 34 |
| 15-26 | LAIKIQRSNGLI | 32 |
| 699-710 | DVIKALRLAMQL | 72 |

Example 3

Identification of HLA-A2 Binding Peptides of NY-CO-58

Methods

Mice

HHD mice were maintained at the John Radcliffe Hospital Biomedical Services and used at 6-10 weeks of age. HHD mice express a transgenic chimeric monochain class I molecule in which the C terminus of the human β2-microglobulin (β2-m) was covalently linked to the N terminus of chimeric A2 α1 and α2 domains fused with the Db α3 domain (Pascolo et al. *J Exp Med.* 1997 Jun. 16; 185(12):2043-51).

Immunization Protocols

Mice were primed with NY-CO-58 plasmid DNA and boosted with recombinant NY-CO-58 vaccinia virus. Control mice were immunized with mel3 DNA and mel3 vaccinia. Plasmid DNA for injection was diluted in PBS at 1 mg/ml. 50 μg DNA was injected into each musculus tibialis under general anesthesia. Ten days after DNA injection, mice were boosted with $10^6$ PFU of recombinant vaccinia virus which was injected i.v. into the lateral tail vein. Tail bleed was done from the lateral tail vein 7 days after vaccinia boost and 10-20 drops of blood was collected from each mouse. PBLs were isolated after depletion of RBCs with RBC lysis solution (Puregene; Gentra Systems, Minneapolis, Minn.). Mice were sacrificed 14 days after boost and spleens harvested.

Identification of Potential HLA A2 Binding Peptides

These peptides were identified using 2 computer based prediction algorithms, SYFPEITHI (developed in the University of Tubingen by Dr Hans-Georg Rammensee) and the HLA peptide binding prediction program developed by Dr K Parker and hosted on the BIMAS website (bimas.dcrt.nih.gov/molbio/hla_bind/). The top 20 peptides predicted by both algorithms were chosen.

Murine Elispot Assay

Elispot assays were done on Multiscreen-IP 96 well plates (Millipore, Billerica, Mass.) using MabTech mouse IFN-γElispot kit according to the manufacturer's recommendations, as described in Salio et al., *J. Exp. Med.* February 16; 199(4):

567-579, 2004. Response of peripheral blood lymphocytes from the tail bleed or splenocytes to stimulation with 2 μM or 10 μM peptide respectively was measured after an overnight incubation of 20 hours. In all experiments, stimulation with 1 μg/ml PHA served as positive control, and stimulation with 10 μM melan A peptide (ELAGIGILTV; SEQ ID NO:73) as negative control.

Culture of Murine Lymphocytes

Splenocytes were restimulated with one third of the splenocytes which were pulsed for 1 hour with 1 μM peptide. Restimulated splenocytes were maintained in complete RPMI supplemented with 10 U/ml IL2. Cells were restimulated every 14 days with HHD splenocytes pulsed with peptide. They were used in Elispot assays after at least 14 days.

NY-CO-58 Plasmid DNA

NY-CO-58 cDNA was obtained from Dr M Scanlan (Ludwig Institute of Cancer Research, New York Branch). This was cloned into the DNA vector pSG2.

Recombinant Vaccinia WR Containing NY-CO-58

A full length cDNA copy of NY-CO-58 was cloned into the vector pSC1130R.2 and the recombinant vaccinia made by homologous recombination into the thymidine kinase gene as previously described. Townsend, A., Bastin, J., Gould, K., Brownlee, G., Andrew, M., Coupar, B., Boyle, D., Chan, S, and Smith, G., Defective presentation to class I-restricted cytotoxic T lymphocytes in vaccinia-infected cells is overcome by enhanced degradation of antigen. *J. Exp. Med.* 1988. 168: 1211-1224.

Predicted HLA-A2 Binding NY-CO-58 Peptides

In the peptide number that follows each listed peptide the first number corresponds to the peptide pool; the second number shows the peptide number in that pool.

Predicted by both BIMAS and SYFPEITHI

| AINPELLQL | (SEQ ID NO:41) | 4-2 |
| LLLVHEPKL | (SEQ ID NO:42) | 4-5 |
| LVHEPKLKV | (SEQ ID NO:43) | 5-1 |
| AMASRDVFL | (SEQ ID NO:44) | 5-4 |
| VLEDGKQQV | (SEQ ID NO:45) | 6-1 |
| SLLALKECI | (SEQ ID NO:46) | 6-2 |
| NLSKEEEEL | (SEQ ID NO:47) | 6-3 |
| IIQQGPDWL | (SEQ ID NO:48) | 6-4 |
| ALRDVIKAL | (SEQ ID NO:49) | 6-5 |

BIMAS Alone

| LQARLFPGL | (SEQ ID NO:50) | 6-6 |
| TIFEGGKAT | (SEQ ID NO:51) | 2-5 |
| KLGLEVYVT | (SEQ ID NO:52) | 3-3 |
| KQQVQVVGL | (SEQ ID NO:53) | 3-4 |
| VVGLQEHLV | (SEQ ID NO:54) | 3-5 |
| KMIDMGSAC | (SEQ ID NO:55) | 4-1 |
| RMHGKFSLV | (SEQ ID NO:56) | 4-3 |
| ALGQNKAHT | (SEQ ID NO:57) | 4-4 |
| KAMEELKEI | (SEQ ID NO:58) | 5-2 |
| FVNKAESAL | (SEQ ID NO:59) | 5-3 |
| MASRDVFLL | (SEQ ID NO:60) | 5-5 |

SYFPEITHI Alone

| RLFPGLAIK | (SEQ ID NO:61) | 1-1 |
| SANVRTVNL | (SEQ ID NO:62) | 1-2 |
| NLEKSCVSV | (SEQ ID NO:63) | 1-3 |
| KIPAPKESL | (SEQ ID NO:64) | 1-4 |
| SSANPVNSV | (SEQ ID NO:65) | 1-5 |
| MIKEFRATL | (SEQ ID NO:66) | 2-1 |
| SIPSKCLLL | (SEQ ID NO:67) | 2-2 |
| DLLNKKAKL | (SEQ ID NO:68) | 2-3 |
| EINKSLLAL | (SEQ ID NO:69) | 2-4 |
| ALKECIRAL | (SEQ ID NO:70) | 3-1 |
| GISSCEYTL | (SEQ ID NO:71) | 3-2 |

Figure 4B:
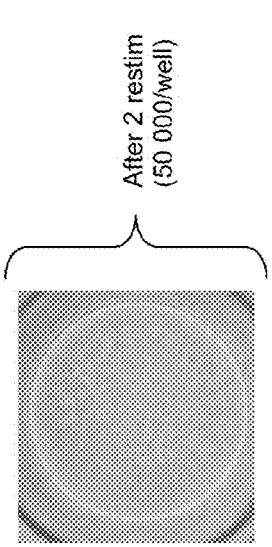
Figure 4C:
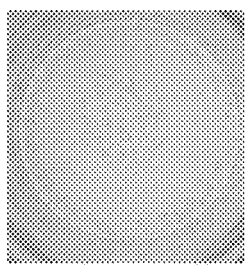
FIGS. 4C and 4D are the negative and positive controls, respectively, for the two-stimulation experiment.
Figure 4D:
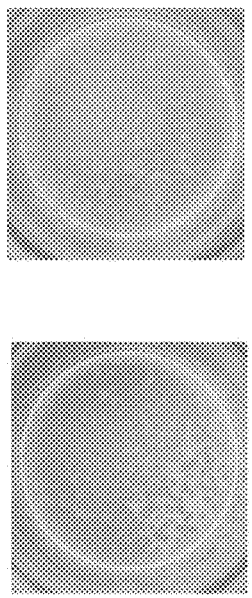
Figure 4E:
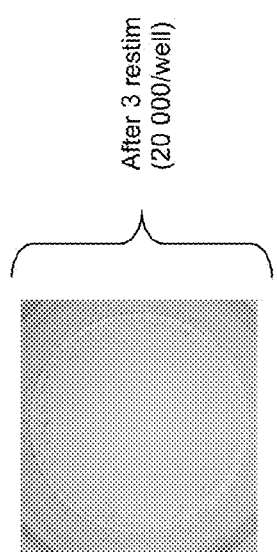
FIG. 4E shows results after three restimulations using Group 3 peptides.
Figure 4F:
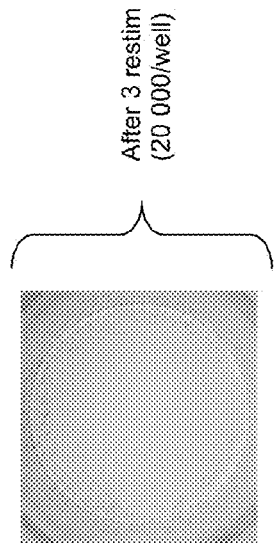
FIGS. 4F and G show results after three restimulations using peptide 3-3.
Figure 4G:
FIG. 4 shows the results of the assay of Group 3 peptide 3 (KLGLEVYVT; SEQ ID NO:52).
FIG. 4H is the negative control for the three-restimulation experiment. Group 3 peptides=pool of 5 peptides including KLGLEVYVT (SEQ ID NO:52). The number in parenthesis is the number of spots per well.
Figure 4H:
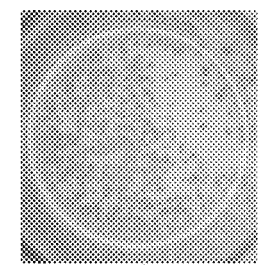

Experiments were performed in A2 transgenic mice using plasmid DNA and vaccinia virus encoding the full length NY-CO-58. Splenocytes and PBL were then tested in ex-vivo ELISPOT assays and after in vitro stimulation using a panel of 31 A2 binding NY-CO-58 peptides (SEQ ID NOs:41-71). The ex vivo ELISPOT from PBL showed a response against the peptide SLLALKECI (SEQ ID NO:46), which was subsequently confirmed using in vitro stimulated cultures (see FIG. 1). Three additional responses were detected after in vitro restimulation against the peptides: LQARLFPGL (SEQ ID NO:50), NLEKSCVSV (SEQ ID NO:63), and KLGLEVYVT (SEQ ID NO:52). Results obtained with SEQ ID NOs:50, 63, and 52 are shown in FIGS. 2, 3, and 4, respectively. Since these responses were not seen in the ex vivo analysis, it is possible that T cell responses specific to these peptides were competed out by vaccinia-specific responses. To address this, responses generated by boosting mice with vaccinia NY-CO-58 and NY-CO-58 cloned into adenovirus (Adeno-NY-CO-58) are compared.

TIL and PBL from colon carcinoma patients are monitored using the above-described methods. A tumor line has been established from an A2 positive patient and with a control B cell line, it was confirmed that the tumor line expresses NY-CO-58.

Other aspects of the invention will be clear to the skilled artisan and need not be repeated here. Each reference cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method of inducing or enhancing an immune response in a subject comprising:
administering to a subject diagnosed with or having cancer an isolated polypeptide comprising the amino acid sequence set forth as SEQ ID NO:20, in an amount effective to induce or enhance the immune response in the subject.

2. The method of claim 1, wherein the immune response is mediated by HLA class I molecules.

3. The method of claim 1, wherein the immune response is mediated by HLA class II molecules.

4. The method of claim 1, wherein the cancer is colon cancer.

* * * * *